(12) United States Patent
Aznar Benitah et al.

(10) Patent No.: US 12,286,484 B2
(45) Date of Patent: *Apr. 29, 2025

(54) TARGETING METASTASIS STEM CELLS THROUGH A FATTY ACID RECEPTOR (CD36)

(71) Applicants: FUNDACIÓ INSTITUT DE RECERCA BIOMÈDICA (IRB Barcelona), Barcelona (ES); INSTITUCIÓ CATALANA DE RECERCA I ESTUDIS AVANÇATS, Barcelona (ES)

(72) Inventors: Salvador Aznar Benitah, Barcelona (ES); Gloria Pascual Angulo, Barcelona (ES); Andres Castellanos Martin, Barcelona (ES); Merce Martin Peña, Barcelona (ES)

(73) Assignees: FUNDACIÓ INSTITUT DE RECERCA BIOMÈDICA (IRB BARCELONA), Barcelona (ES); INSTITUCIÓ CATALANA DE RECERCA I ESTUDIS AVANÇATS, Barcelona (ES)

(*) Notice: Subject to any disclaimer, the term of this patent is extended or adjusted under 35 U.S.C. 154(b) by 846 days.

This patent is subject to a terminal disclaimer.

(21) Appl. No.: 17/021,894

(22) Filed: Sep. 15, 2020

(65) Prior Publication Data

US 2021/0380712 A1    Dec. 9, 2021

Related U.S. Application Data

(63) Continuation of application No. 15/763,423, filed as application No. PCT/EP2016/073208 on Sep. 29, 2016, now Pat. No. 11,535,680.

(30) Foreign Application Priority Data

Sep. 29, 2015 (EP) ..................................... 15382474

(51) Int. Cl.
| | | |
|---|---|---|
| G01N 33/00 | (2006.01) | |
| A61P 35/04 | (2006.01) | |
| C07K 16/28 | (2006.01) | |
| C07K 16/30 | (2006.01) | |
| C12N 15/113 | (2010.01) | |
| G01N 33/50 | (2006.01) | |
| G01N 33/53 | (2006.01) | |
| G01N 33/574 | (2006.01) | |
| A61K 39/00 | (2006.01) | |

(52) U.S. Cl.
CPC .......... C07K 16/2896 (2013.01); A61P 35/04 (2018.01); C07K 16/30 (2013.01); C12N 15/1138 (2013.01); G01N 33/5011 (2013.01); G01N 33/57484 (2013.01); A61K 2039/505 (2013.01); C07K 2317/24 (2013.01); C07K 2317/76 (2013.01); C12N 2310/14 (2013.01); C12N 2310/531 (2013.01); G01N 2333/70596 (2013.01); G01N 2500/00 (2013.01)

(58) Field of Classification Search
None
See application file for complete search history.

(56) References Cited

U.S. PATENT DOCUMENTS

| 11,535,680 | B2* | 12/2022 | Aznar Benitah | ....... A61P 35/04 |
| 2004/0009171 | A1* | 1/2004 | Gerritsen | ............... C07K 14/82 |
| | | | | 530/388.25 |

FOREIGN PATENT DOCUMENTS

| WO | WO-03032813 A2 * | 4/2003 | ............. C07K 14/82 |
| WO | WO-2003032813 A2 | 4/2003 | |

OTHER PUBLICATIONS

Geloen et al. (PLOS One, May 2012, vol. 7, Issue 5, e37633). (Year: 2012).*
International Search Report and Written Opinion for Application No. PCT/EP2016/073208, mailed Nov. 11, 2016, European Patent Office, Netherlands, 10 pages.
Alghazeer, R., et al., "Cytotoxicity of oxidised lipids in cultured colonal human intestinal cancer cells (caco-2 cells)," *Toxicology Letters* 180(3):202-211, Elsevier BV, Netherlands (2008).

(Continued)

*Primary Examiner* — Lisa V Cook
(74) *Attorney, Agent, or Firm* — Sterne, Kessler, Goldstein & Fox P.L.L.C.

(57) ABSTRACT

Targeting metastasis stem cells through a fatty acid receptor. The disclosure provides the use of blockers or inhibitors of CD36 activity or expression for the treatment of oral squamous cell cancer (OSCC), particularly for the treatment of generated metastases and for diminish is generation from primary tumours. Apart from shRNAs, anti-CD36 antibodies are provided as blockers or inhibitors, especially those that block the binding of CD36 to oxidized LDL and fatty acids and their incorporation into cells, because the promotion of their transport is indicated as the mechanism by which CD36 promote metastases dissemination and growth. Also provided is a method for identifying candidates to anticancer agents, particularly for OSCC metastasis, among those that promote in CD36+ cells, in vivo or in vitro, effects associated to CD36 depletion or blocking such as decrease of growth accumulation of lipid droplets and decrease of size in the case of metastases.

22 Claims, 62 Drawing Sheets
Specification includes a Sequence Listing.

(56) References Cited

OTHER PUBLICATIONS

Balaban, S., et al., "Obesity and Cancer Progression: Is there a Role of Fatty Acid Metabolism?" *BioMed Research International* 2015:274585, Hindawi Publishing Corporation, United States (2015).

Coburn, C.T., et al., "Defective uptake and utilization of long chain fatty acids in muscle and adipose tissues of CD36 knockout mice," *J Biol Chem* 275(42):32523-9, American Society for Biochemistry and Molecular Biology Inc., United States (2000).

Defilippis, R.A., et al., "CD36 repression activates a multicellular stromal program shared by high mammographic density and tumor tissues," *Cancer Discov* 2(9):826-39, American Association for Cancer Research Inc., United States (2012).

Geloen, A., et al., "CD36 Inhibitors Reduce Postprandial Hypertriglyceridemia and Protect against Diabetic Dyslipidemia and Atherosclerosis," *PLoS One* 7(5):e37633, Public Library of Science, United States (2012).

Hale, J.S., et al., "Cancer stem cell-specific scavenger receptor 36 drives glioblastoma progression," *Stem Cells* 32(7):1756-58, Wiley-Blackwell, United States (2014).

Ibrahimi, A., et al., "Muscle-specific overexpression of FAT/CD36 enhances fatty acid oxidation by contracting muscle, reduces plasma triglycerides and fatty acids, and increases plasma glucose and insulin," *Journal of Biological Chemistry* 274(38):26761-26766, American Society for Biochemistry and Molecular Biology Inc., United States (1999).

Lai, K.C., et al., "Blocking TNF-α inhibits angiogenesis and growth of IFIT2-depleted metastatic oral squamous cell carcinoma cells," *Cancer Letters* 370(2):207-215, Elsevier BV, Netherlands (2015).

Nguyen, D.X., et al., "Genetic determinants of cancer metastasis," *Nat Rev Genet* 8(5):341-352, Nature Publishing Group, United Kingdom (2007).

Nguyen, D.X., et al., "Metastasis: from dissemination to organ-specific colonization," *Nature Rev. Cancer* 9(4):274-284, Nature Publishing Group, United Kingdom (2009).

Pascual, G., et al., "Targeting metastasis-initiating cells through the fatty acid receptor CD36," *Nature* 541(7635):41-45, Nature Publishing Group, United Kingdom (2016).

Pepino, M.Y., et al., "Structure-function of CD36 and importance of fatty acid signal transduction in fat metabolism," *Annual Review of Nutrition* 34:281-303, Annual Reviews Inc., United States (2014).

Miyazaki, H., et al., "Overexpression of nm23-H2/NDP Kinase B in a Human Oral Squamous Cell Carcinoma Cell Line Results in Reduced Metastasis, Differentiated Phenotype in the Metastatic Site, and Growth Factor-independent Proliferative Activity in Culture," Clin Cancer Res 5 (12):4301-4307, American Association for Cancer Research, United States (Dec. 1999).

Omura, K., "Current status of oral cancer treatment strategies: surgical treatments for oral squamous cell carcinoma," Int J Clin Oncol 19(3):423-30, Springer Nature, Switzerland (Apr. 2014).

Sato, S., et al., "Inhibition of CD44v9 upregulates the invasion ability of oral squamous cell carcinoma cells," Oral Oncology 39:27-30, Elsevier, Netherlands (Apr. 2014).

Nath, A. and Chan, C. "Genetic alterations in fatty acid transport and metabolism genes are associated with metaststic progression and poor prognosis of human cancers," Scientific Reports 6:18669, Springer Nature, Switzerland (Jan. 2016).

Kalikaki, A., et al., "Comparison of EGFR and K-RAS gene status between primary tumours and corresponding metastases in NSCLC," British Journal of Cancer 99(6):923-9, Springer Nature, Switzerland (Sep. 2008).

Ng, C., et al., "Prognostic signatures in breast cancer: correlation does not imply causation," Breast Cancer Research 14:313, Springer Nature, Switzerland (2012).

\* cited by examiner

PRIMARY TUMOR LN METASTASIS

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: DNA sequence for CD36 shRNA TRCN0000056998

<400> SEQUENCE: 1
gaagttacat attaggccat                                              20

<210> SEQ ID NO 2
<211> LENGTH: 20
<212> TYPE: DNA
<213> ORGANISM: Artificial Sequence
<220> FEATURE:
<223> OTHER INFORMATION: DNA sequence for CD36 shRNA TRCN0000056999

<400> SEQUENCE: 2
ccgacgttaa tctgaaagga                                              20

<210> SEQ ID NO 3
<211> LENGTH: 19
<212> TYPE: DNA
<213> ORGANISM: Artificial Sequence
<220> FEATURE:
<223> OTHER INFORMATION: DNA sequence for ACSL1 shRNA V3THS_313936

<400> SEQUENCE: 3
taaatatgtg cttttccg                                                19

<210> SEQ ID NO 4
<211> LENGTH: 56
<212> TYPE: DNA
<213> ORGANISM: Artificial Sequence
<220> FEATURE:
<223> OTHER INFORMATION: Forward primer K164AFw used for constructing
      the CD36Lys164mut mutant

<400> SEQUENCE: 4
ctgacttgga acatagaaga ttttgacgcg ttaataagtg aattgaggat catttg      56

<210> SEQ ID NO 5
<211> LENGTH: 56
<212> TYPE: DNA
<213> ORGANISM: Artificial Sequence
<220> FEATURE:
<223> OTHER INFORMATION: Reverse primer K164ARv used for constructing
      the CD36Lys164mut mutant

<400> SEQUENCE: 5
caaatgatcc tcaattcact tattaacgcg tcaaaatctt ctatgttcca agtcag      56
```

```
<210> SEQ ID NO 6
<211> LENGTH: 27
<212> TYPE: DNA
<213> ORGANISM: Artificial Sequence
<220> FEATURE:
<223> OTHER INFORMATION: cDNA sequence of the CD36 receptor at the level
      of the point mutation introduced to generate the fatty
      acid-binding site mutant CD36Lys164mut
<220> FEATURE:
<221> NAME/KEY: misc_feature
<222> LOCATION: (13)..(15)
<223> OTHER INFORMATION: Mutated codon

<400> SEQUENCE: 6
tcactcatta acaagtcaaa atcttct                                        27

<210> SEQ ID NO 7
<211> LENGTH: 9
<212> TYPE: PRT
<213> ORGANISM: Artificial Sequence
<220> FEATURE:
<223> OTHER INFORMATION: Amino acid sequence of the CD36 receptor at the
      level of the point mutation introduced to generate the fatty
      acid-binding site mutant CD36Lys164mut
<220> FEATURE:
<221> NAME/KEY: MISC_FEATURE
<222> LOCATION: (5)..(5)
<223> OTHER INFORMATION: Mutated Lys

<400> SEQUENCE: 7

Ser Leu Ile Asn Lys Ser Lys Ser Ser
1               5
```

TARGETING METASTASIS STEM CELLS THROUGH A FATTY ACID RECEPTOR (CD36)

CROSS-REFERENCE TO RELATED APPLICATIONS

This application is a continuation of U.S. application Ser. No. 15/763,423 ("the '423 application"), filed Mar. 26, 2018, which issued as U.S. Pat. No. 11,535,680 on Dec. 27, 2022. The '423 application is a 371 of International Application No. PCT/EP2016/073208, filed Sep. 29, 2016, which claims priority to European Patent Application No. 15382474.3, filed Sep. 29, 2015. The contents of all above-named applications are incorporated herein by reference.

REFERENCE TO SEQUENCE LISTING SUBMITTED ELECTRONICALLY

The content of the electronically submitted sequence listing in ASCII text file (Name: 2020-09-09_SeqListing_4427-0010002; Size: 2,370 bytes; and Date of Creation: Sep. 9, 2020) is incorporated herein by reference in its entirety.

TECHNICAL FIELD

The invention relates to the field of searching for and producing candidates and agents to treat cancer and the control of said disease. More specifically, the invention relates to the use of antibodies and other inhibitors of CD36 activity or expression for the treatment of oral squamous cell carcinoma (OSCC) as well as to the identification of candidates for treatments effective against said cancer and its metastases.

BACKGROUND OF THE INVENTION

Squamous cells are a kind of epithelial cell that line several organs of the body, among others: the epidermis, lips and oral cavity. Squamous cell carcinoma (SCC) is a general term for cancers in such cells. Although the terminology is the same, the SCC of different body sites is usually very different with regard to symptoms, prognosis and response to treatment. This is described in detail on the web site of the National Institute of Health (www.cancer.gov) or the professional version of the Merck Manual (www.merckmanuals.com), oral squamous cell carcinoma (OSCC) is a type of head and neck cancer that starts in squamous cells of lips and oral cavity and is the most common cancer of the lips and oral cavity. Smoking and drinking alcohol are important risk factors.

About 40% of intraoral SCCs begin on the floor of the mouth or the lateral and ventral surfaces of the tongue. About 38% of all oral carcinomas occur on the lower lip; these are usually cancers related to sun exposure on the external surface. Cancer cells may spread into deeper tissues as the cancer grows. Treatment is by surgery, radiation and/or conventional chemotherapy; although surgery plays a larger role in the treatment of most oral cavity cancer. The overall 5-year survival rate (all sites and stages combined) is >50%.

Early, curable lesions are rarely symptomatic, and preventing fatal disease requires early detection by screening. If carcinoma of the tongue is localized (no lymph node involvement), 5-year survival is >50%. For localized carcinoma of the floor of mouth, 5-year survival is more than 65%. Lymph node metastasis decreases survival rate by about 50%. Metastases reach the regional lymph nodes first and then later the lungs. Carcinoma of the upper lip tends to be more aggressive and metastatic.

The mechanisms whereby some tumour cells detach from the primary lesion to colonize distant sites are still largely unknown. Pro-metastatic events common to the majority of solid tumours might include the reversible transition of tumour cells from an epithelial to a mesenchymal state as well as their interactions with stromal components, such as periostin or tenascin-C, or with tumour-activated stromal cells, such as pericytes, fibroblasts, endothelial cells, adipocytes or immune cells. Some tumours also secrete metastasis-promoting exosomes that contain proteins, mRNA and micro RNAs to establish a distant pro-metastatic niche. However, it is not known whether the primary lesions already contain subpopulations of cells with the mutational repertoire to confer metastatic potential, or whether they require additional mutations or epigenetic changes to be able to colonize distant sites. Indeed, it remains to be elucidated whether metastasis-initiating cells are a subpopulation of tumour stem cells, or these are two independent populations.

Slow-cycling cancer cells with the highest primary tumour-initiating potential have been identified in breast cancer mammospheres, and cultured melanoma, prostate cancer, and OSCC cell lines (Pece et al., 2009; Roesch et al., 2010; Bragado et al., Qin et al., 2012). In vivo data indicates that slow-cycling tumour cells are responsible for post-chemotherapy relapse in colon cancer and glioblastoma (Kreso et al., 2013; Chen et al., 2012). Hale et al. (2014) reported that glioblastoma contains a self-renewing, tumourigenic cancer stem cell population that contributes to glioblastoma progression and resistance to therapy.

They state that CSCs selectively use the scavenger receptor CD36 to promote their maintenance using patient-derived CSCs and in vivo xenograft models. The assays provided confirmed that oxidized phospholipids, which are CD36 ligands, are present in glioblastoma cells and that the proliferation of CSC, but not of non-CSC, increased with the exposure to oxidized low-density lipoproteins. Glioblastoma is not a metastatic cancer, but tumour recurrence is frequently observed after resection, radiation and chemotherapy, so that median survival of patients suffering from glioblastoma remains between 12 and 18 months following diagnosis, primary lesions being the cause of death in most patients. Therefore, the understanding of the mechanism why CSCs respond to microenvironment signals is important.

CD36 (HGNC:1663, EntrezGene:948, Ensembl: ENSG00000135218, OMIM: 173510, UniProtKB: P16671) is a receptor protein with several different known functions, as it is indicated by the different alternative names that it receives: it is known, among others, as cluster determinant 36, thrombospondin receptor, collagen type I receptor, leukocyte differentiation antigen CD36, platelet glycoprotein 4 or fatty acid translocase. The Entrez Gene and UniProt/SwissProt Summaries for CD36 gene, as recapitulated by GeneCards (www.genecards.org) describe the protein as the fourth major glycoprotein of the platelet surface that serves as a receptor for thrombospondin in platelets and various cell lines.

Since thrombospondins are widely distributed proteins involved in a variety of adhesive processes, this protein may have important functions as a cell adhesion molecule. It binds to collagen and thrombospondin, mediating the anti-angiogenic effect of the latter, as well as to anionic phospholipids and oxidized LDL. It directly mediates cytoadherence of *Plasmodium falciparum* parasitized erythrocytes and it binds long chain fatty acids and may function in the transport and/or as a regulator of fatty acid transport. It is a co-receptor for TLR4-TLR6 heterodimer that promotes inflammation in monocytes/macrophages. Upon ligand binding, such as oxLDL or amyloid-beta 42, rapidly induces the formation of a heterodimer of TLR4 and TLR6, which is internalized and triggers inflammatory response, leading to NF-kappa-B-dependent production of CXCL1, CXCL2 and CCL9 cytokines, via MYD88 signalling pathway, and CCL5 cytokine, via TICAM1 signalling pathway, as well as IL1b secretion. CD36 is also at the top of the signalling cascade that uptakes lipids from the extracellular environment and triggers their beta-oxidation to obtain energy in the form of ATP (Coburn et al., 2000; Ibrahimi et al., 1999; Pepino et al., 2014).

CD36 has been previously involved in cancer, but its implication and mechanism of action is not clear.

WO 03/032813 discloses assays where it is shown that CD36 is one of the genes upregulated in renal cell carcinoma. Although no assays are presented for other types of cancer, CD36 is presented in said application as a useful target for the diagnosis and/or treatment, and even prevention, of certain cancers, being also considered as a predictor of the prognosis of the tumour treatment. SCC is mentioned as one of the possible cancer types where the treatment with CD36 antibodies, or antagonists such as antisense RNA, can be of use, but without providing any evidence of changes of CD36 expression in SCC or, particularly, of the efficacy of CD36 antibodies or other antagonists for preventing or treating either primary tumours or metastases. Spontaneous animal tumours are proposed for testing the efficacy of antibodies specifically binding the proteins that are overexpressed in renal cell carcinoma according to the assays shown in WO 03/032813, and, given that it is a highly invasive and malignant tumour, feline oral SCC is proposed as a suitable model. However, again, such proposal is done without providing examples of the actual utility of said approach and moreover, without showing any evidence that any of the genes overexpressed in renal cell carcinoma are also overexpressed in feline oral SCC and, particularly, not showing either any data about changes (increase or decrease) in the level of expression of CD36 in feline oral SCC or any evidence about a possible involvement of CD36 in the initiation, development or spread of metastasis in such type of cancer. Moreover, it is commented that feline oral SCC exhibits low incidence of metastasis, but also mentioning that this might be due to the short survival times of cats with this tumour.

For breast cancer, some authors (DeFillippis et al., 2012) have reported that CD36 repression activates a multicellular stromal program shared by high mammographic density and tumour tissues, so that the decrease/repression of CD36 makes tumours more aggressive. They show that increased expression of CD36 can restore stromal phenotypes associated with low risk tissues.

The available data indicate that the role of CD36 in different kinds of cancer, if any, might be different and opposed depending on the particular kind of cancer considered and, even, on the particular stage of said cancer. Some authors (Balaban et al., 2015) had suggested that the multifunctional character of CD36 might be associated with the different role of changes in CD36 expression depending on the cancer type. They mention that low CD36 gene expression correlates with a higher metastasis grade in colon and ovarian cancers and with low recurrence-free survival but, conversely, CD36 mRNA expression in breast cancer is inversely correlated with the metastatic potential of five breast cancer cell lines, where its expression is relatively higher in less aggressive cell lines and almost absent in highly aggressive lines (ZR-75 and MDA-MB-231). This inconsistency between cancer types may be explained by the multifunctionality of CD36. While it functions as a fatty acid transporter, CD36 is also involved in collagen adhesion and, therefore, lower expression of CD36 may lead to reduced cell adhesion, providing cancer cells with a higher metastatic potential. They suggest that the rate of fatty acid uptake mediated by CD36 in each particular case might also have an important implication in the effect on cancer progression, and that it might be influenced by an obese microenvironment.

Other groups have suggested a role of oxidized lipids in the metabolism and functionality of cancer cells. They are broadly regarded as compounds with a cytotoxic effect (Alghazeer et al., 2008), so that an excessive uptake of oxidized lipids may lead to a reduced viability of cancer cells and even to apoptosis.

The involvement of lipid uptake and metabolism in cancer progression has been discussed by other research groups. It is generally considered that cancer cells, that are usually cells with a high rate of division, have an altered energetic metabolism, so that glucose and lipids are metabolized differently than in normal cells. The specific modifications in lipid metabolism in cancer cells have not been clearly identified, and it has not been studied in developed metastasis.

The role of CD36 and/or lipid metabolism in the development and progression of different cancer types needs further clarification in order to use them as targets for modifications that may lead to effective cancer treatments. Meanwhile, preventing and inhibiting the metastatic spread of solid tumours remains to be a critical next step in cancer treatment.

The search for effective targets for OSCCs treatment, in turn, should be continued or improved, particularly for metastases originating in OSCC primary tumours, since approximately 50% of OSCC patients develop lymph node metastases alone or in combination with lung lesions. Patients often already present the metastasis at the time they are diagnosed of the primary tumour in the clinic. Survival rates of metastatic patients are very low: most of them succumb to the metastatic disease (Young et al., 2015; Gleber-Netto, et al., 2015), because the usual increase of intensity of radiation treatments seems not to be effective in most cases and resection therapies are rarely effective when lymph nodes are affected and, more importantly, they are not advisable or easy to perform when they have reached the lungs. Conventional chemotherapy, besides, does not abolish metastasis. Thus, an appropriate treatment for the control and, if possible, remission of metastases originating from OSCC primary tumours remains to be an unmet and long-lasting need.

The present invention provides a solution to said problem.

SUMMARY OF THE INVENTION

Metastasis is the leading cause of cancer-related deaths. For most human cancers, the identity of the cells that initiate and promote metastasis is still unknown, hampering our ability to develop therapies to prevent or inhibit the spread of tumour cells to distant sites. Using an orthotopic model of human oral squamous cell carcinoma (OSCC), the present inventors have now identified a subpopulation of CD44bright cells within the primary lesion with the highest potential to develop lymph node and lung metastasis. This population is slow-cycling, expresses high levels of the receptor CD36 at the cell membrane, and relies on fatty acid metabolism to thrive in lymph nodes and bronchoalveolar environments. When transplanted in the oral cavity of mouse models, CD36+/CD44bright cells are as capable as their CD36−/CD44bright counterparts of promoting primary tumour initiation and growth, but are exclusive in their ability to initiate and promote metastasis. Importantly, inhibition of CD36 by either shRNA or neutralizing antibodies severely impairs metastatic initiation and spread of primary OSCC patient samples and established cell lines. Further underscoring its importance, CD36 overexpression in cells derived from poorly disseminating tumours confers an aggressive metastatic behavior. Therefore, it is herein proposed that targeting CD36+ metastasis stem cells could provide a breakthrough therapeutic avenue required to successfully stop the metastatic spread of tumours, particularly in OSCC.

Thus, the present invention refers, in a first aspect, to a blocker of activity and/or expression of CD36 for use in the treatment of cancer in a mammal, wherein the cancer is oral squamous cell cancer (OSCC). More preferably, the OSCC is in a stage wherein at least one metastasis has developed for the primary tumour, which metastasis or metastases can be in the lymph node and/or in the lung. The metastases in lymph nodes to treat can also have other origins.

As it is mentioned below, the blocker is a molecule or compound, or a salt thereof. Thus, the first aspect of the invention can be also defined as referring to a compound which is a blocker of activity and/or expression of CD36, or a salt thereof, for use in the treatment of cancer in a mammal, wherein the cancer is oral squamous cell cancer (OSCC). Therefore, all the embodiments and/or preferences expressed above and below with regard to the first aspect of the invention also apply to the mentioned alternative way of defining the first aspect of the invention.

Thus, the molecule, compound or salt thereof that is provided for use in the treatment of OSCC according to the present invention can be a blocker of activity or a blocker of expression, or even both of them. Therefore, in a possible embodiment, the molecule or compound or salt thereof, that is considered a blocker of CD36 activity and/or expression, is a blocker of activity, that is, an antagonist of CD36. In another possible embodiment, the molecule, compound or salt thereof, that is considered a blocker of CD36 activity and/or expression, is a blocker of CD36 expression which is an inhibitor of CD36 expression.

When the blocker is a blocker of activity it can be an antibody, preferably monoclonal. It is particularly preferred that the antibody blocks both the binding of CD36 to oxidized LDL and fatty acids and their incorporation into cells.

The blocker can also be an inhibitor of CD36 expression, such as an shRNA or an iRNA, an small interference RNA, or an antisense RNA or DNA molecule, or an analogue thereof.

In a possible embodiment, compatible with all the previous ones, the mammal is a human being.

Additionally, it is also considered a part of this aspect of the invention, a blocker of activity and/or expression of CD36 for use according to any one of the preceding claims, wherein the cancer, instead being oral SCC, is a melanoma.

As can be seen, an additional aspect of the invention, strongly connected to the first one so that it can be considered an alternative way of defining the first aspect of the invention, is a method of treating OSCC in a subject which is in need thereof, comprising administering to the subject a therapeutically effective amount of a compound which is blocker of activity and/or expression of CD36. Again, the preferences and embodiments corresponding to the first aspect of the invention are also applicable to this additional aspect, particularly the one referring to the subject or mammal being a human being. Another particularly preferred embodiment, of course compatible with the embodiment of the subject being a human being, is that one where the method of treating OSCC is a method of treating or preventing OSCC metastases. The metastases will be lymph node metastases and/or lung metastases. The compound to be administered, that is, the blocker of activity and/or expression of CD36, can be preferably selected among an antibody directed to CD36 or a shRNA; in the latter case, the shRNA will be preferably administered via administration of an expression vector thereof. When the compound is an antibody, and especially when the subject is a human being, the compound to be administered can be a humanized antibody.

In a second aspect, the present invention also relates to a method for identifying a compound as a candidate for the treatment of OSCC metastases which comprises the steps of:
a. contacting the compound with CD36+ assay cells;
b. checking whether an effect related to CD36 blocking or depletion is produced;
c. identifying the compound as a candidate for the treatment of OSCC metastases if such effect is produced.

When the method is carried out in vivo, the CD36+ cells will be cells of a metastasis, the compound will be administered to the assay animal for enabling the contact with the cells and the assessed effect can be a diminish of metastases growth and/or an accumulation of cells with lipid droplets. Usually, at least one metastasis will be in the lymph nodes and/or the lung.

The method can be carried out in vitro, using SCC cultures wherein the number of CD36+ has been enriched by sorting or by previous incubation with an appropriate culture medium and the assessed effect is promotion of growth: if it is reduced by the compound, this will be identified as a candidate to drug against OSCC metastases.

An additional embodiment assesses if an accumulation of swollen lipid droplets is produced, with also identifies the compound as a candidate. The method can be carried out by detecting the signal of fluorescent lipids.

BRIEF DESCRIPTION OF THE FIGURES

FIG. 1A, Detection of LR-CSCs by flow cytometry in SCC-25 xenografts analysed between 4-6 weeks after SCC inoculation (n=6 animals). Numbers indicate CD44$^{bright}$dye+, CD44$^{bright}$dye− and CD44$^{dim}$ cells in the represented gate expressed as percentages of total GFP+ Lin− SCCs from the parental tumour. (n=3 independent experiments). FIG. 1B, Percentage of dividing cells in the GFP+CD44+DID+ and GFP+CD44+DID− populations analysed by BrdU incorporation and flow cytometry. FIG. 1C, Representation of the quantification of dividing cells in the different populations identified in B: DID+ versus DID−, P<0.05; CD44+ versus CD44−, P<0.05, two-tailed t-test (n=6 independent experiments, 3 mice per experiment). FIG. 1D, Global quantification of CD44$^{bright}$Dye$^+$, gD44$^{bright}$Dye$^-$ and CD44$^{dim}$ cells from SCC-pLucGFP xenografts detected with a FACS strategy where viable single cells were selected on the basis of being GFP+ and negative for lineage (Lin) cocktail of antibodies (H2KD, CD31 and CD45) to exclude mouse cells; GFP+Lin− cells were gated for CD44 and dye. FIG. 1E, Representative flow cytometry analysis of the SCC-25 cell line represented in D; percentages from the total GFP+Lin− SCC parental tumour are shown.

FIG. 3A, Detection of CD36+CD44$^{bright}$ cells by flow cytometry of SCC-25, VDH-00 and FaDu xenografts analysed at 4-6 weeks (n=8 animals per cell line). Numbers indicate CD44$^{bright}$C36$^{bright}$ C44$^{bright}$CD36$^{low}$ cells in the represented gate, expressed as percentages from the total GFP+ Lin− SCC parental tumour. Histograms show the correlation between CD36 expression and DID content for each xenograft. FIG. 3N, Bar charts representing the normalized photon flux observed in primary tumours (left chart) or metastasis (right chart) from SCC-25 or JHU-029 (as indicated over the bars) transformed with the PMSCV-EV empty vector (bars labelled "EV") or with the CD36-OE vector (bars labelled "CD36-OE") relative to the value observed when the SCC-25 cells have been transformed with the PMSCV-EV empty vector. PT, primary tumour; LN-Met, lymph node metastasis; Lung-Met, lung metastasis.

FIG. 5A, Left chart: Bioluminiscent quantification of FaDu PLKO and shRNACD36 (#98 and #99) metastasis 4 weeks after SCC injection. Data are given as mean and s.e.m. PLKO, n=9; shRNACD36 #98, n=10; shRNACD36 #99, n=10; P=0.05, two-tailed Mann-Whitney test. n.s., not significant. Right charts: Penetrance of metastasis in FaDU PLKO and shRNACD36 (#98 and #99) xenografts expressed in percentages. FIG. 5B. Flow cytometry analysis of primary tumours and metastasis from FaDu PLKO and shRNACD36 (#98 and #99) xenografts analysed 4 weeks after SCC injection. Numbers indicate CD44$^{bright}$CD36+, CD44$^{bright}$CD36− and CD44$^{dim}$ (differentiated) cells in the represented gate, expressed as percentages from the total GFP+Lin− SCC parental tumour, n=6 animals per group. FIG. 5C. Representative pictures of lungs from PLKO and shRNACD36 #99 FaDu xenografts showing the rounded nodules of metastatic SCC in PLKO absent in the shRNACD36. PLKO, n=5; shRNACD36 #99, n=5. FIG. 5D. Bioluminiscent imaging and quantification of FaDu PLKO and shRNACD36 #99 primary tumours, lymphatic metastasis (labelled as LN-Met or metastasis LN) or lung metastasis (labelled as Lung-Met or metastasis Lung); the frequency of developed primary tumours (left top chart), lymph node metastasis (intermediate top chart) or lung metastasis (right chart) is represented, as well as the normalized photon flux observed in primary tumours (left lower chart), lymph node metastasis (lower intermediate chart) or lung metastasis (right lower chart) calculated with relation to the value observed, in each case, in PLKO cases (PLKO, n=9; shRNACD36 #99, n=10), P=0.02, P=0.05, two-tailed Mann-Whitney U test. Data given as the mean and s.e.m.; PT, primary tumour; LN-Met, lymph node metastasis; Lung-Met, lung metastasis. FIG. 5E, Ratio primary tumour/lymph node metastasis bioluminescence signals in the intervals 1-3 weeks (T1-T3) and 3-4 weeks (T3-T4) for each group PLKO or shRNACD36 #99; data are given as the mean. FIG. 5F. Representative haematoxylin and eosin (H&E) staining of metastatic lymph nodes from PLKO and shRNACD36 #99. LDs, lipid-droplets. PLKO, n=5; shRNACD36 #99, n=5). FIG. 5G, Representative pictures of tumours collected 4 weeks after SCC injection. FIG. 5H, Immunostaining of lymphatic metastasis shRNACD36. Insert shows lipid droplets surrounding GFP+CD44+ SCC cells. FIG. 5I, Free fatty acid content in lipid droplets shown in i as determined by BODIPY-568 immunostaining.

FIG. 6A. Bioluminiscent imaging (BLI) and quantification of SCC-25 PLKO and shRNACD36 (#98 and #99) xenografts. Data are given as mean and s.e.m. PLKO, n=9; shRNACD36 #98, n=7; shRNACD36 #99, n=6; P=0.02, P=0.04, two-tailed t-test. FIG. 6B. Frequency of developed metastasis in each of the groups in FIG. 6A. P=0.003, Fisher exact test; n.s., not significant. FIG. 6C. Representative H&E staining of primary tumours from SCC-25 PLKO and shRNACD36 (#98 and #99) xenografts showing evidence of squamous differentiation with keratin pearls structures as compared to higher levels of undifferentiation in SCCs (in PKLO). PKLO, n=4; shRNACD36 #98, n=4; shRNACD36 #99, n=3. te, tongue epithelium; kp, keratin pearls; mt, muscle tissue. FIG. 6D. Flow cytometry analysis of primary tumours from SCC-25 PLKO and shRNACD36 (#98 and #99) xenografts. Numbers indicate $CD44^{bright}CD36+$, $CD44^{bright}CD36-$ and $CD44^{dim}$ (differentiated) cells in the represented gate, expressed as percentages from the total GFP+Lin– SCC parental tumour. The right panel shows the shift in the mean fluorescence intensity for each group. n=5 animals per group. FIG. 6E. Bioluminiscent imaging (BLI) of SCC-25 PLKO and shRNACD36 (#98 and #99) xenografts, accompanied by the representation of the quantification of the developed primary tumours or metastasis (upper charts), as well as the representation of the normalized photon flux observed in primary tumours or in metastasis, calculated in each case relative to the value observed in PLKO xenografts. FIG. 6F. Representative H&E staining of primary tumours from PLKO and shRNACD36 #98 xenografts showing evidence of the presence of large swollen cells in the sample depleted of CD36 by the expression of the shRNA, which cells were not present in the PKLO sample.

FIG. 7A. Bioluminiscent imaging (BLI) 4 weeks after SCC injection of Detroit-562 PLKO and double shRNACD36 (#98 and #99) xenografts from high fat diet (HFD) or control diet-fed mice (CTD). FIG. 7B. Frequency of developed primary tumours (upper left chart) and metastasis (upper right chart), together with the normalized photon flux observed in the primary tumours (bottom left chart) and metastasis (bottom right chart) in each of the groups in FIG. 7A, (n=5 animals per group). FIG. 7C. Average weight (upper chart) and glucose level in blood (lower chart) found in the mice fed with control diet (circles; PLKO and shRNACD36 animals) or high fat diet (squares; PLKO and shRNACD36 animals) at the days from injection indicated below the charts. FIG. 7D. Flow cytometry analysis of xenograft from Detroit-562 PKO and double shRNACD36 #98 #99 (high gat diet and control diet fed-mice) analysed 4 weeks after SCC injection. Numbers indicate $CD44^{bright}CD36+$, $CD44^{bright}CD36-$ and $CD44^{dim}$ (differentiated) cells in the represented gate, expressed as percentages from the total GFP+Lin– SCC parental tumour. n=5 animals per group.

FIG. 8A. Bioluminiscent imaging (BLI) and quantification of Detroit-562 scramble and shRNA-ACSL1 (#936) xenografts at 4 weeks after SCC injection. P=0.001, 0.002; two-tailed t-test. FIG. 8B. Frequency of developed metastasis to the lymph nodes in each of the groups in FIG. 8A. Scramble, n=5; shRNA-ACSL1, n=5. FIG. 8C. Representative haematoxylin and eosin (H&E) staining of metastatic lymph nodes from Detroit-562 scramble and shRNA-ACSL1 (#936 n=3 animals per group.

FIG. 9A. Bioluminiscent imaging (BLI) and quantification (normalized photon flux found in primary tumours and metastases, and frequency of developed primary tumour and metastases) of JHU-029 scramble and shRNA-ACSL1 (#936) xenografts at 2 and 4 weeks after SCC injection. P=0.001, 0.002; two-tailed t-test. The frequency of developed primary tumours and metastasis to the lymph nodes in each of the groups is also represented. Scramble, n=5; shRNA-ACSL1, n=5. FIG. 9B. Representation of shift in the mean fluorescence intensity for the groups of: primary tumours from JHU-029 control, overexpressing CD36 and treated with the scramble shRNA (group JHU-029 CD36OE/SCR), or overexpressing CD36 and treated with shRNA-ACSL1 (JHU-029 CD36OE/shRNA-ACSL1) FIG. 9C. Bar chart representing the CD36 RNA expression level, relative to the control, in the groups CD36OE/SCR y CD36OE/shRNA-ACSL1 of FIG. 9A and FIG. 9B.

FIG. 10A, Experimental set-up. FIG. 10B, Mice were injected with FACS-sorted (n=10) Detroit-562 $CD44^{bright}CD36+$ or $CD44^{bright}CD36-$ pLuc-GFP cells, and tumour growth was monitored. Data are given as mean and s.e.m. $CD44^{bright}CD36+$, n=7; $CD44^{bright}CD36-$, n=7, P<0.05, two-tailed t-test. The yellow arrow indicates a higher affinity of CD36+-injected cells for the metastatic site. FIG. 10C, Flow cytometry analysis of tumours from CD36+ and CD36– secondary transplants at 4 weeks showing the reestablishment of the original heterogeneity regarding CD36/CD44 expression. Numbers indicate $CD44^{bright}CD36+$, $CD44^{bright}CD36-$ and $CD44^{dim}$ cells in the represented gate, expressed as percentages from the total GFP+Lin– SCC parental tumour. $CD44^{bright}CD36+$, n=5; $CD44^{bright}CD36-$, n=5. FIG. 10D, Flow cytometry analysis and sorting strategy of in vitro 2-day co-cultured Detroit-562 and SCC-25 with OP9 (control) or OP9 induced to adipogenesis (adipogenic OP9), showing the increase in the percentage of positive cells in the adipogenic co-cultures. Numbers indicate $CD44^{bright}CD36+$ and $CD44^{bright}CD36-$ from the total GFP+CD29– SCC cells.

FIG. 12A, Flow cytometry analysis of OSCC cells co-cultured with adipogenic OP-9 or with 0.4 mM palmitic acid (PA). Histograms show the average normalized number of events as a function of CD36 and CD44 fluorescence intensity. FIG. 12B, Fatty acid uptake assay for SCC-25 cells not transduced (as control, CT) or transduced with CD36 wt (overexpressing wild-type CD36), shRNA CD36 or and CD36Lys164mut (expressing a K164A-mutated CD36). FIG. 12C, representative images and quantification of BLI (bioluminescent image) monitoring of transplants from SCC-25 cells overexpressing CD36 wt (wild-type, n=10) or CD36Lys164mut (n=10). In FIG. 12C, the frequency of developed tumours is expressed as percentage (P=0.02, Fisher exact test), and BLI signal quantification is expressed as the relative normalized photon flux (P=0.05, two-tailed t-test). Data are given as the mean and s.e.m. FIG. 12D, FACS analysis of OSCC cells overexpressing either CD36 wild-type (wt) or mutant (Lys164mut). Histograms show the average normalized number of events as a function of CD36 and CD44 fluorescence intensity. FIG. 12E, representative images and quantification of BLI monitoring of tumours generated from palmitic acid-treated cells transplants. FIG. 12F, representative images and quantification of BLI monitoring of tumours generated by primary OSCC cells transduced with CD36 wt (wild-type) (n=10) or CD36Lys164 mutant (n=10). BLI data are shown as mean and s.e.m. All graphs of FIG. 12C, FIG. 12E, and FIG. 12F show the frequency of developed tumours and BLI signal quantifications.

FIG. 13A, Representative haematoxylin and eosin (H&E) staining of metastatic lymph nodes from SCC-25-pLucGFP transplants with overexpressed CD36 wt (wild-type) or CD36Lys164mut (fatty acid-binding site mutant). Dashed line denotes the areas surrounded by lipid droplets in the Lys164mut. FIG. 13B shows Caspase-3 immunostaining of the metastases reported in FIG. 13A, and FIG. 13C shows shRNA-CD36 FaDu-pLucGFP metastatic lymph nodes, with both FIG. 13B and FIG. 13C showing activated casp-3-positive apoptotic cells in the vicinity of droplets FIG. 14. Relative expression levels expressed as percentages of four populations, CD36+CD44bright, CD36+CD44dim, CD36−CD44bright and CD36−CD44dim, as determined by FACS analysis of the primary tumour and metastasis of the OSCC cell lines SCC-25, JHU-029, Detroit-562 and FaDu and the patient-derived carcinoma lines (PDCs) VDH-00, VDH-01 and VDH-02. Experiments were repeated 4 times.

FIG. 16A, Experimental set-up of the assay of co-culture and injection of OSCC cells and adipogenic OP9, FACS-sorted and injected into the oral cavity of NSG mice. FIG. 16B, Bioluminescent image (BLI) monitoring of transplants of Detroit-562/OP-9 and SCC-25/OP-9 sorted-injected cells $CD44^{bright}CD36+$ and $CD44^{bright}CD36-$ from co-cultured OSCC. The arrows indicate the increased affinity of CD36+ SCC for the metastatic site. Detroit-562, $CD44^{bright}CD36+$, n=5; $CD44^{bright}CD36-$, n=6; SCC-25, $CD44^{bright}CD36+$, n=5, $CD44^{bright}CD36-$, n=3. FIG. 16C, FIG. 16D, Frequency of developed metastasis (FIG. 16C) and primary tumours (FIG. 16D) generated by Detroit-562 and SCC-25 $CD44^{bright}CD36+$ and $CD44^{bright}CD36-$ groups compared with parental cell lines. P=0.01, P=0.009, two-tailed Fisher exact test. Detroit-562, $CD44^{bright}CD36+$, n=5, $CD44^{bright}CD36-$, n=6; SCC-25, $CD44^{bright}CD36+$, n=5, $CD44^{bright}CD36-$, n=3. FIG. 16E. Signal quantifications (normalized photon flux) from primary tumours generated by $CD44^{bright}CD36+$ or $CD44^{bright}CD36-$ cells sorted from SCC25 OSCC cell line. FIG. 16F, FIG. 16G, Frequency of metastasis-initiating cells (MIC: FIG. 16F) and tumour-initiating cells (TIC: FIG. 16G) found after orthotopic inoculation of limiting dilutions (as indicated on the left) of CD36+CD44bright, CD36−CD44bright and CD44bright cells, as indicated below the X-axis.

FIG. 17A, FACS strategy to isolate $CD36+CD44^{bright}CD36-C44^{bright}$ and $CD44^{bright}$ from in vitro SCC-25 cells co-cultured with adipogenic OP-9 cells. Serial limiting dilutions of the different populations were injected immediately after FACS sorting. FIG. 17B, FIG. 17C, Metastasis-initiating cell (MIC) frequency (FIG. 17B), and tumour-initiating cell (TIC) (FIG. 17C) frequency of the three different populations in FIG. 17A, as determined by ELDA software statistical analysis.

FIG. 18A, Bioluminescent signal of FaDu SCC pre-treated in vitro with neutralizing anti-CD36 (JC63.1 and FA6.152) or the corresponding control isotype (IgA and IgG1) xenografts. Data are given as mean and s.e.m. Anti-CD36 JC63.1, n=10; IgA, n=10; anti-CD36 FA6.152, n=9; IgG1, n=10, results from two independent experiments, P<0.05 two-tailed t-test. FIG. 18B, Frequency of primary tumours developed versus tumour-free animals in each of the FIG. 18A groups. P=0.03, two-tailed Fisher's exact test. FIG. 18C, Frequency of developed LN metastases in animals that developed primary tumours in FIG. 18A. P=0.01, P=0.03, two-tailed Fisher's exact test. None of the anti-CD36 treated animals developed metastasis to the lungs. FIG. 18D, Mice were injected with FaDu cells and then injected with the anti-CD36 FA6.152 antibody intraperitoneally every 3 days. The graph shows the bioluminescent monitoring of tumours. None of the animals treated with the anti-CD36 FA6.152 developed metastasis. Anti-CD36 FA6.152, n=3; IgG1, n=3. FIG. 18E, Mice were inoculated with Detroit-562 cells and monitored every day for bioluminescence; once metastatic signal appeared, animals were treated intraperitoneally with neutralizing anti-CD36 JC63.1 or control isotype every day. Graphs show bioluminescence monitoring of tumours. Anti-CD36 JC63.1, n=7; IgA, n=8; primary tumour, P=0.009; metastasis P=0.005, two-tailed t-test. FIG. 18F, The graph shows the fold changes in the bioluminescence signal between T1 (start of treatment) and T3 (final time point) within each of the groups in FIG. 18E. P=0.002, two-tailed t-test. FIG. 18G, Dose-response and bioluminescent imaging (BLI) signals of tumours from mice treated daily with monoclonal JC63.1 or the corresponding IgA isotype control for 3 weeks. FIG. 18H, Bioluminescence image monitoring and frequency of developed primary tumours (upper right bar chart) or metastases (bottom right bar chart) of VDH-02 xenografts treated in the same way described in FIG. 18G. Anti-CD36 JC63.1, n=5; IgA, n=5, P=0.04, one-tailed t-test. FIG. 18I, Representative pictures of metastatic lymph nodes of animals treated daily with neutralizing anti-CD36 JC63.1 or an IgA control, taken 2.5 weeks after starting treatment. The dashed line shows the difference in size of metastatic lymph nodes between the groups. FIG. 18J, Representative H&E staining of tumours reported in FIG. 18H. Detroit-562, anti-CD36 JC63.1, n=4; IgA, n=4; VDH-02, anti-CD36 JC63.1, n=3; IgA, n=3. FIG. 18K, Activated caspase-3 immunostaining of metastatic lymph nodes of Detroit-562 transplants from mice treated with monoclonal anti-CD36 JC63.1 (10 mg 100 ml$^{1}$), or with the IgA isotype control. FIG. 18L, Weight of the animals after a three-week period of daily administration of JC63.1 or IgA. Doses (5, 10 or 20 mg 100 ml$^{1}$) are indicated in brackets.

FIG. 19A, FIG. 19B, BLI images (FIG. 19A) and monitoring (FIG. 19B) of immunocompetent C3H/HeJ mice treated daily with monoclonal JC63.1 or IgA. Graphs show BLI signals from tumours (P=0.05, two-tailed t-test). FIG. 19C, Fold change in metastasis BLI signal of the animals reported in c. 15% of the mice showed remission of metastatic events, as compared to control IgA treated mice. Data in FIGS. 19B and 19C are given as the mean and s.e.m.

FIG. 20A, BLI metastases signal from mice inoculated intravenously with plucGFP PLKO and shRNACD36 breast luminal-A MCF-7 and 501mel melanoma-transduced cell lines. Graphs show the relative proportion of developed metastases per group. FIG. 20B, BLI signals from metastases in FIG. 20A.

FIG. 21A. Correlation of CD36 associated signature expression and overall survival (left) and disease-free survival (right) in lung squamous cell carcinoma (LUSC) and bladder carcinoma (BLCA). FIG. 21B. Correlation of CD36 expression and overall survival in luminal A breast cancer (BRCA). In FIG. 21A and FIG. 21B, darker grey line (red line in the original), subjects whose tumour cells expressed signature (a) or CD36 (b) greater than the median; lighter grey line (green line in the original), those whose tumour cells expressed signature (a) or CD36 (b) less than the median.

DETAILED DESCRIPTION OF THE INVENTION

Figure 1A:
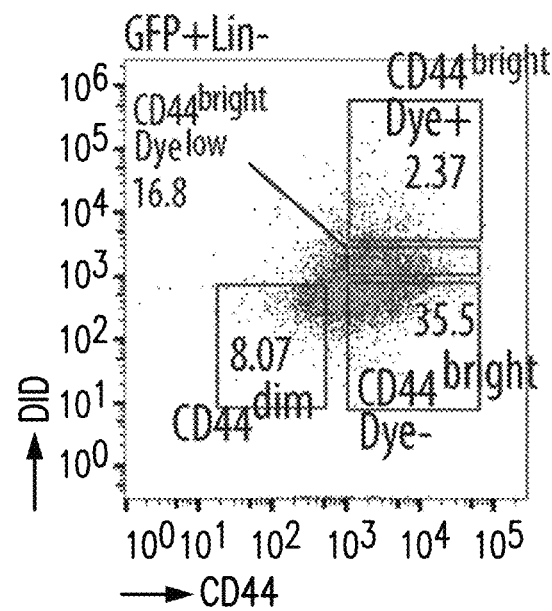
FIGS. 1A-1E. OSCCs contain a population of CD44$^{bright}$ label-retaining cells that express a transcriptome signature predominantly associated to lymphatic metastasis and lipid metabolism.

The present invention is based on the findings achieved by the present inventors by using an orthotopic model of OSCC to study the cell cycle heterogeneity of tumour cells in vivo, as described by Myers et al. (2002). With this model, the present inventors have identified a small population of CD36+ cells that contribute to the initiation and growth of OSCC tumours but that are highly predisposed to promote lymph node metastasis.

Assays described in the Examples of the present application show the effect of modulating the expression/activity of CD36 on primary tumour growth, which is included and quantified for several patient-derived tumour and established cell lines. It can be seen that some primary oral tumours respond better than others to CD36 inhibition, but the overall conclusion found by the present inventors is that depletion of endogenous CD36 in vivo by shRNA or blocking of activity by means of neutralizing antibodies slightly reduces primary tumour burden.

However, the present inventors have found that, in every single tumour tested, inhibition of CD36 (both by antibodies neutralizing its activity or by shRNAs) has a dramatic effect regarding metastasis initiation and progression, decreasing metastatic penetrance and growth of all cell lines and patient-derived tumours that they have tested. This is a very surprising effect because, as it has been discussed above, an inverse correlation had been previously reported for CD36 expression with regard to metastatic potential of different tumours and low CD36 gene expression has been found to correlate with a higher metastasis grade in other metastatic cancer such as colon and ovarian cancers and its expression is almost absent in highly aggressive breast cancer lines.

Very importantly, blocking CD36 prevents metastasis-promoting cells from surviving and thriving in the lymph nodes and lungs. This is a remarkable finding because metastases, and not primary tumour growth (with some few exceptions such as glioblastoma, which is not a metastatic cancer, with the patients' death occurring before metastases can appear), are the primary cause of death of the majority of patients that develop cancer. Specific treatments for metastases are often not known and, particularly, no specific treatment for OSCC-derived metastases is available. The present invention, however, provides a therapeutic option for the treatment of OSCC that can be a preventive treatment of metastases (a treatment of a subject having an OSCC primary tumour intended to prevent metastases), or an ameliorating treatment of already existing metastases, particularly in the lymph nodes and/or lungs.

Upon depletion of endogenous CD36, the remaining small metastases contain a large number of differentiated tumour cells, and accumulate large amounts of lipid droplets, probably resulting in lipid toxicity. Thus, the most likely cause of cell death is an excessive intracellular accumulation of lipids, resulting in lipid toxicity. Lipids are more concentrated in the lymphatic system and lymph nodes than in circulation (Dixon et al., 2010; Randolph et al., 2014), and lipid beta-oxidation is the most energetically efficient in terms of moles of ATP per molecule metabolized. Hence, CD36+ cells might take advantage of this specific nutrient environment to obtain the high amount of energy that is likely required to anchor and survive at these sites distant from the primary tumour.

Many tumour types metastasize to the lymph nodes or to areas rich in lipids, such as the bone marrow. Therefore, the present invention shows that targeting CD36 could provide a breakthrough therapeutic avenue required to successfully stop the metastatic spread in patients with oral SCC or, even, as the analysis of publicly available raw data performed by the inventors indicates, other types of tumours, including those of bladder, lung SCC, luminal mammary gland and even melanomas (see Example 5).

Thus, in a first aspect, the present invention provides blockers of activity and/or expression for use in the treatment of cancer in a mammal, particularly for the treatment of oral squamous cell cancer (OSCC), and very especially when it is in a metastasizing stage, so that metastases have appeared and least one metastasis exists.

This aspect of the invention is particularly addressed to the treatment of metastases of the lymph nodes, so that an embodiment of the invention is the treatment of one or more metastases in at least one lymph node, which metastasis can stem from an OSCC primary tumour or from other primary tumour. Treatment of lung metastases, particularly OSCC lung metastases, is also comprised within the scope of the present invention.

As it is used herein, the term "blocker" includes any compound, or salt thereof, that reduces or abolishes the activity of its target, in this case, CD36. The term blocker is often used as synonym of receptor antagonist (particularly in the case of alpha blockers, beta blockers and calcium channel blockers), as a reduction or complete inhibition of expression also gives rise to a reduction of the activity of the non-expressed protein, the term blocker, as it is used herein, also encompasses those compounds that inhibit, partially or completely, the expression of the corresponding gene. Thus, a compound that can be a blocker suitable for the purposes of the present invention can be a small organic molecule, that is, a molecule of a size comparable to those organic molecules generally used in pharmaceuticals, which organic molecules can be natural but that are often obtained by chemical synthesis or modification or natural molecules, and which usually exhibit a size of up to about 5000 Da, provided that such molecule is capable of blocking, reducing or inhibiting the activity and/or expression of CD36. But the term also encompasses biological molecules, fragments or analogues thereof of very different sizes, again with the provision that they are capable of blocking, reducing or inhibiting the activity and/or expression of CD36. Antibodies, for instance, which are formed by four polypeptide chains connected at some points by covalent bonds giving a single molecule and that often are capable of blocking or inhibiting the activity of those receptors they bind to, are included within the group of compounds wherefrom a blocker for use according to the present invention can be selected, as it is obvious for someone skilled in the art from the assays of some Examples of the present specification. Other biological compounds, such as those molecules formed by a number of units of nucleotides or analogues thereof, particularly oligonucleotides or analogues thereof such as shRNAs, siRNAs or antisense RNAs or DNAs, are also encompassed within the meaning of the term blocker.

Therefore, the blocker can be an inhibitor of expression of CD36. An "inhibitor of expression" refers to a natural or synthetic compound that has the effect of inhibiting or significantly reducing the expression of a gene, which gene, for the purposes of the present invention, will be the CD36 gene. One or more shRNA or siRNA can be used. Both kind of compounds are well known possible inhibitors of gene expression, in the case of shRNA, after the processing by Drosha, inclusion of the processing product in the RNA-induced silencing complex (RISC) by DICER and union of the antisense strand to the mRNA complementary sequence, with cleavage of the mRNA when complementary is perfect and repression of mRNA translation by RISC in other cases, leading to target gene silencing in any of the cases. Some assays shown in the Examples below have been carried out with shRNAs, which can be expressed from a multiplicity of vectors, such as retroviral/lentiviral vectors targeting the selected gene, CD36, such as it has been done in Examples of the present application. They can be also expressed from other suitable vectors, insertional or non-insertional, well known by those skilled in the art. A variety of shRNAs for human CD36 (and even for other species, such as mouse) are commercially available from different providers, such as Sigma-Aldrich, that also provides siRNAs. A siRNA (small interference RNA) is a double stranded small (20-25 nucleotides) RNA that operates within the RNA interference pathway and interferes with the expression of specific genes with complementary nucleotide sequences by degrading RNA after transcription, resulting in no translation. When siRNAs are used, they can be expressed from vectors administered to the subject or they can be administered as such, in compositions where suitable excipients can be also present, that will be selected depending on the intended administration via. Different shRNAs or siRNA can be designed with the aid of known algorithms and methodologies such as the one described, for instance, in the web site of the Broad Institute (www.broadinstitute.org).

As would be obvious to those skilled in the art, antisense therapy can be administered for that same purpose, by synthesizing a RNA or DNA molecule, usually an oligonucleotide, or an analogue thereof, whose base sequence is complementary to the gene's messenger RNA and that will bind to said messenger RNA and inactivate it, turning the gene "off" because the mRNAs molecules have to be single-stranded to be translated. When administering oligonucleotides in a composition, it is preferable to use analogues thereof, that is, oligonucleotides where the nucleotide units have some chemical modification to their structure. Such modifications are usually in the sugar moiety and/or in the phosphate bond, and include the addition of one or more non-nucleotide moieties. The interest of such modification is that they usually render the molecule more resistant to nucleases, such as: the commonly used phosphorothyoate bonds instead of the phosphate bonds; modifications at the 2' position of the sugar moiety such as 2'-O-methyl or 2'-O-methoxyethyl modifications; modifications where the ribose exhibits a link connecting the oxygen at 2' with the carbon at 4', thus blocking the ribose in the conformation 3'-endo (LNAs: locked nucleic acids); the replacement of the sugar backbone by an amide-containing backbone such as an aminoethylglycine backbone, as in peptide nucleic acids (PNAs); use of PMOs (nucleic acids where the ribose moiety is replaced by a morpholine group); and other modifications well known by those skilled in the art that can be found reviewed, for instance, by Kole et al. (2012).

Further modifications, such as the attachment of one or more cholesterol moieties at one or both ends of the molecules, can facilitate the entering of the molecule in the cells. The design of antisense molecules can be obvious for those skilled in the art from the sequence of CD36 mRNA molecule and reviews such as the one of Kole et al. previously mentioned.

It is preferred that the blocker is a compound or molecule that modulates the activity of CD36, antagonizing or blocking it. Any CD36 receptor antagonist, or even inverse agonists could be used. As used herein, a receptor antagonist is a receptor ligand or drug that blocks or hinders agonist-mediated responses; as agonists are the compounds that bind to a receptor and activate the receptor to produce a biological response, antagonists, by blocking the action of the agonists, also block, inhibit or diminish the activity of the receptor. An inverse agonist is a compound that binds to the same receptor as the agonist but exerts the opposite effect; inverse agonists have the ability to decrease the constitutive level of receptor activation in the absence of an agonist. The compound that blocks or inhibits CD36 activity can be an antibody, preferably a specific antibody. It is also possible to use analogues or fragments of antibodies, such as single chain antibodies, single chain variable domain fragments (scFv), F(ab')$_2$ fragments (which can be obtained by pepsin digestion of an antibody molecule), or Fab fragments (which can be obtained by reducing the disulphide bridges of the F(ab')$_2$ fragments. Humanized antibodies can be used when the subject is a human being.

As CD36 has several known functions, the antibody can be selected so that it inhibits all known functions of CD36, including its interaction with thrombospondin, collagens and fatty acids (as happens with the antibody FA6.152 used in assays shown in the present application) or only specific functions, as antibody JC3.1 also used in assays disclosed in the present application, which only blocks fatty acid and oxidised-LDL uptake. Both antibodies exerted the same anti-metastatic effect, as can be seen in Example 4 of the present application. When inoculated in vivo, they significantly inhibited LN metastases, reduced the penetrance of oral lesions by 25-30%, resulted in a significant reduction of the size of primary tumours and completely prevented any metastatic growth in the LN after having orally inoculated tumour cells. Very importantly, when treated mice had already developed LN metastases, the size of the metastases was reduced more than 80% (with some lesions showing complete remission) after daily peritoneal injections of neutralizing antibodies. Large cells swollen with lipids accumulated in the lymph node metastases of mice treated with CD36 neutralizing antibodies, similarly to the shRNA-mediated knockdown of CD36.

As the results indicate that the pro-metastatic effect of CD36 in OSCC relied on its ability to modulate lipid metabolism, rather than its other known functions, it is preferred that the selected antibody is at least capable of blocking or diminish fatty acid and oxLDL uptake.

In the Examples below, no mice developed any visible side effects from the continuous treatment with CD36-neutralizing antibodies, which indicates that mice or any other mammal subject suffering from cancer, such as a human being, will tolerate well a continuous therapy with CD36 blockers or inhibitors in clinical conditions, particularly a therapy with CD36-neutralizing antibodies. Even so, with the aim of avoiding possible secondary effects resulting from the interaction with CD36 in other organs affecting, for instance, CD36 interaction with thrombospondin, it is preferred that the selected antibody specifically blocks fatty acid and oxLDL uptake and does not affect other CD36 functions or interactions.

As it is shown in the mentioned assays, the antibodies can be administered systemically, for instance, intraperitoneally, and can be in the form of an appropriate suspension, for instance an aqueous suspension, in water or another appropriate liquid such as saline solution.

When the subject to be treated is a human being, which is a preferred embodiment of the present invention, some commercial anti-CD36 can be used or the antibody can be prepared for being administered to human beings. For antibodies that have been generated in a non-human immune system (as those used in the assays of the present application), such as in mice, humanization can be necessary to enable their administration to human beings, in order to avoid adverse reactions. Humanized antibodies are antibodies, usually monoclonal antibodies, initially generated in a non-human species and whose protein sequences have been modified to increase their similarity to antibody variants produced naturally in humans, so that minimal sequence derived from non-human immunoglobulins remain. Even after humanization, the amino acid sequence of humanized antibodies is partially distinct from antibodies occurring naturally in human beings. Several processes are known for those skilled in the art for antibody humanization, as it has been reviewed, for instance, by Almagro and Fransson (2008), including: humanizing through production of a mouse-human (mouse Fab spliced to human Fc) chimera, which chimera might be further humanized by selective alteration of the amino acid sequence of the Fab portion; insertion of one or more CDR segments of the "donor" (non-human antibody) by replacing the corresponding segments of a human antibody, which can be done using recombinant DNA techniques to create constructs capable of expression in mammalian cell culture, or even avoiding the use of non-human mammals by creating antibody gene libraries usually derived from human RNA isolated from peripheral blood and displayed by micro-organisms or viruses (as in phage display) or even cell free extracts (as in ribosome display), selection of the appropriate intermediate product (usually, antibody fragments such as Fab or scFv) and obtaining full antibodies for instance, again, recombinant DNA techniques. Several patent documents have been dedicated to humanization methods like, for instance U.S. Pat. No. 6,054,297, assigned to Genentech; U.S. Pat. Nos. 5,225,539 and 4,816,397 are also useful references.

The method for obtaining monoclonal antibodies is well known for those skilled in the art. In general, antibodies against CD36 receptor can be raised according to known methods, such as those mentioned in classic laboratory manuals as "Antibodies: A Laboratory Manual, Second edition", edited by E. A. Greenfield in 2014, by administering CD36 whole protein or a fragment or epitope thereof to a host animal which is a different from the mammal where a therapeutic effect is sought. Monoclonal antibodies in particular can be prepared and isolated by any technique that provides for the production of antibody molecules by continuous cell lines in culture, such as the hybridoma technique originally described by Kohler and Milstein (1975), the human B-cell hybridoma technique (Cote et al., 1983), or the EBV-hybridoma technique (Cole et al., 1985). Alternatively, as commented above, Fab and/or scFv expression libraries can be constructed to allow rapid identification of fragments having the desired specificity to the CD36 receptor.

For the design of antibodies with a particular specificity, it is advantageous to resource to annotated NCBI Reference Sequence (NC_000007.14, *Homo sapiens* annotation release: 107, which is the current release on 29 Sep. 2015) or UniProtKB P16671, in order to choose as immunogen, if wished, a particular domain or region of the antibody to be targeted or mutated before generating the antibodies.

For achieving a therapeutic effect, the compound, which is a blocker of activity and/or expression of CD36, will be administered preferably in therapeutically effective amounts. An "effective dose" or "therapeutically effective amount" is an amount sufficient to exert a beneficial or desired clinical result. The precise determination of what would be considered an effective dose may be based on factors individual to each patient, including their size, age, cancer stage, and nature of the blocker (e.g. expression construct, antisense oligonucleotide, antibody or fragment thereof, etc). Therefore, dosages can be readily ascertained by those of ordinary skill in the art from this disclosure and the knowledge in the art. Multiple doses can be also administered to the subject over a particular treatment period, for instance, daily, weekly, monthly, every two months, every three months, or every six months. In certain dose schedules, the subject receives an initial dose at a first time point that is higher than one or more subsequent or maintenance doses.

The findings discussed in the present application also open a pathway for the identification of candidates to anticancer drug, particularly for the treatment of metastases. Classical target validation and screens have been performed using cells in culture and assessing their inhibitory effect over proliferation and apoptosis in culture. So far, this classical approach has failed to significantly affect metastatic spread of tumours, so that many potent in vitro and in vivo antiproliferative/proapoptotic drugs have unfortunately failed in the clinic. Nowadays the field of cancer has managed to develop good models to study and characterize metastasis (including excellent examples in human melanoma, colon cancer, breast cancer and, in the present case, oral cancer), which are allowing the understanding of the process of metastasis in an unprecedented manner.

The present inventors have also put their efforts on developing systems to screen best antibody/small compound candidates, taking advantage of the fact that the mechanism whereby CD36 depletion/blocking/inhibition results in a very clear effect on reduction of metastasis growth and initiation relies on lipid metabolism. Without wishing to be bound by any theory, inhibition of CD36 seems to prevent the ability of metastatic cells to obtain the large amounts of energy they require to survive at a distant site through lipid metabolism, a source of energy that is favoured by the metastatic tumour cell when lymph nodes are colonized, a reason why it is expected that the similar mechanism may be involved in other metastases developed in lymph node.

Therefore, the present invention also provides a method for identifying a compound as a candidate for the treatment of OSCC metastases which comprises the steps of:
  a. contacting the compound with CD36+ assay cells;
  b. checking whether an effect related to CD36 blocking or depletion is produced;
  c. identifying the compound as a candidate for the treatment of OSCC metastases if such effect is produced.

A possible embodiment of the method of the invention is carrying out the method in vivo, as it has been carried out in Example 4 of the present application, so that the assay cells are cells of a metastasis, preferably a lymph node metastasis, which has been induced by oral inoculation of an animal model with OSCC tumour cells, the compound contacts the assayed cells because it is administered to the animal (for instance, intraperitoneally) and the expected effect is the reduction of the size of the metastasis previously produced in comparison to the size that it had before the administration of the candidate compound. An alternative CD36 effect to be determined is the accumulation of large cells swollen with lipids in the metastases with regard to a control, which has not received the candidate compound.

However, the present inventors have developed a variant wherein the method can be carried out in vitro, wherein the assayed cells are SCC cells that are cultured in a medium that has been previously used for culturing adipocytes and that increases the number of CD36+ cells (2-3 days of culture of the SCC cells are sufficient). With this method, the percentage of CD36+ cells becomes very similar to what can be detected in Lymph node metastases in vivo. The possible candidate compound is contacted with such culture and growth promotion is tested with regard to a control that has had no contact with the candidate compound. If growth promotion decreases, the compound is identified as a possible candidate to anticancer agent, particularly against metastases, especially OSCC metastases.

The present inventors have also developed an alternative version of the in vitro method, which relies on visualizing lipid accumulation in SCC cells that have been treated with neutralizing CD36 antibodies or other candidate compound. The method takes advantage of the use of lipid sensors such as the one used in the present application, which is based on derivatives of the fluorophore known as Bodipy. All cells take up Bodipy when it is in the culture medium, because it is just a fluorescent lipid, but those that have been treated with the candidate to anticancer agent should show a clear accumulation of swollen lipid droplets, just as it has been seen in vivo, that could be visualized thanks to the fluorescent lipid using the appropriate wavelength. A particularly preferred embodiment is one that uses a modified version of Bodipy that only becomes fluorescent when internalized in the cell (www.moleculardevices.com) and which makes the assay even cleaner.

In any of the embodiments, the compound that is tested can be an antibody that is used to treat the cells with it.

The invention will be now explained in detail by means of the following Examples and Figures.

EXAMPLES

The assays disclosed in the Examples below were carried out using the following materials and methodologies.

—Animal Studies.

NOD scid gamma (NSG) (NOD.Cg-Prkdc$^{scid}$ Il2rg$^{tm1Wjl}$/iSzJ) mice were purchased from Charles River and crossed in-house. All mice were housed under a regimen of 12 h light/12 h dark cycles and SPF conditions, and all procedures were evaluated and approved by the CEEA (Ethical Committee for Animal Experimentation) from the Government of Catalunya. For establishing patient-derived tumour cells, tumours were implanted subcutaneously into NOD scid gamma mice immediately after tumour resection from the patient. Once the tumours had grown, they were collected, disaggregated, and tumour cells were FACS sorted and cultured as described below. For 5-bromo-2-deoxyuridine (BrdU) labelling experiments, mice were injected intraperitoneally with a single dose of 100 µg g$^{-1}$ BrdU (Invitrogen) and then analysed at 24 h. SCC intra-tongue injection was performed as previously described (Oskarsson et al., 2014; Nieman et al., 2011). Briefly, mice were anesthetized by intraperitoneal injection with a mixture of 50 mg per kg of ketamine and 0.5 mg per kg of medetomidin, and SCC cells resuspended in 30 µl PBS were injected into each mouse tongue with a BD ultra-fine 6 mm needle. For intravenous cell injection, mice were anesthetized with continuous administration of isofluorane gas and were injected by retro-orbital injection with 100,000 cells in 100 µl PBS. Mice were monitored for the luciferase bioluminescent signal immediately after injection (T0) and once weekly thereafter with a Xenogen IVIS Imaging System-100 (Caliper Life Sciences). Briefly, animals were injected by retro-orbital injection with 50 µl of D-luciferin (Promega) diluted in 1× PBS at 5 mg ml$^{-1}$. Continuous administration of isofluorane gas was provided to ensure anesthetizing animals during imaging. Data was quantified with the Living Image software version 4.4 (Caliper Life Sciences). Quantifications were calculated with unsaturated pixels. Color scale minimum and maximum values are shown in pictures.

For MCF-7 breast cell line intravenous injections, a pellet of 17-beta-estradiol (0.18 mg per pellet, 60-day release; Innovative Research of America) was implanted subcutaneously into 8-week-old NSG females 3 days prior to intravenous injection. MCF-7- and 501mel-injected animals were analysed for BLI at 6- or 4-weeks post-inoculation, respectively.

To treat mice in vivo with neutralizing anti-CD36 antibodies, mice were injected intraperitoneally with 100 µl of physiological serum containing 2.5 µg of neutralizing monoclonal anti-CD36 FA6.152 (Abcam, ab17044) or with 2.5 µg of the corresponding IgG1 (mouse IgG1 monoclonal NCG01, Abcam, ab81032), 100 µl of physiological serum containing 5 µg, 10 µg or 20 µg of neutralizing monoclonal anti-CD36 JC63.1 (CAYMAN, CAY-10009893-500) or 5 µg, 10 µg or 20 µg of the corresponding IgA (mouse IgA, kappa [S107], Abcam, ab37322). All antibodies were azide-free with no added preservative compound.

High fat diet experiments were performed pre-feeding the mice during 7 days prior to inoculating the mice with the tumour cells, and thereafter with a 60/Fat Research diet (TD.06414, Harlan). Normal diet was used for control groups. For doxycycline treatment, mice were treated continuously with 50 µg ml$^{-1}$ of fresh doxycycline in the drinking water containing 5% sucrose and protected from light. Glucose levels were measured once a week at a controlled time using a glucometer (BAYER Contour® next).

For each experiment, mice were sacrificed at the same time, once an experimental group reached the humane endpoint according to the approved CEEA protocol (4-6 weeks after the orthotopic injection as soon as mice started to lose weight due to the growth of the oral lesion), and subsequent cell analysis was performed.

Animal tissue was collected and fixed with 4% paraformaldehyde (PFA) for 2 h at room temperature (RT) and then either embedded in OCT and frozen at −80° C. or dehydrated and embedded in paraffin. Toxicological study was performed at the Histopathology Facility according to standard procedures.

Total blood samples from mice were collected from the inferior vena cava and then processed in the Experimental Toxicology and Ecotoxicology Unit (PCB) following standard procedures.

—Clinical Material.

Biological samples were obtained from patients from the Hospital Vall d'Hebron (Barcelona, Spain) under informed consent and approval of the Bank of Tumour Committees of the hospital according to Spanish ethical regulations. The study followed the guidelines of the Declaration of Helsinki, and patient identity and pathological specimens remained anonymous in the context of the study.

—Plasmids.

MSCV-IRES-Luciferase-GFP retrovirus was kindly provided by Dr. Johannes Zuber (Research Institute of Molecular Pathology (IMP), Vienna Biocenter, Austria) (Kalluri et al., 2006). CD36 and ACSL1 knockdown experiments were conducted using lentiviral shRNA targeting the selected gene (Sigma Aldrich and Dharmacon, respectively) (see Table 1a below). A non-targeting shRNA sequence was used as a control (pLKO.1-TRC control; Addgene, plasmid #10879).

CD36-OE (over-expression) experiments were conducted by cloning CD36 cDNA into the lentiviral PMSCV vector. Empty vector was used as control.

The CD36Lys164mut (K164A) mutant construct was made using QuikChange II XL Site-Directed Mutagenesis Kit (Catalog #200521, Agilent Technologies), following the manufacturer's instructions, with the primer pair K164A Fwd and K164A Rvs (see Table 1b below) and the plasmid pMSVCD36OE as template. The sequence of the CD36Lys164mut plasmid was checked by Sanger sequencing. The cDNA and amino acid sequence of the CD36 receptor at the level of the point mutation introduced to generate the fatty acid-binding site mutant CD36Lys164mut are as follows:

```
......... TCA CTC ATT AAC AAG TCA AAA TCT TCT ......    (SEQ ID NO: 6)
           S   L   I   N   K   S   K   S   S            (SEQ ID NO: 7)
          480             490             500
```

TABLE 1

-shRNAs and primers used in connection with plasmids

1a.-shRNAs used to target CD36 or ACSL1

| shRNA | Sequence | SEQ ID NO: |
|---|---|---|
| shRNA CD36 | | |
| TRCN0000056998 | 5' GAAGTTACATATTAGGCCAT 3' | 1 |
| TRCN0000056999 | 5' CCGACGTTAATCTGAAAGGA 3' | 2 |
| shRNA ACSL1 | | |
| V3THS_313936 | 5' TAAATATGTGCTTTTTCCG 3' | 3 |

1b.-Primer used for constructing the CD36Lys164mut mutant

| Primer | Sequence | SEQ ID NO: |
|---|---|---|
| K164A Fw | 5'-CTGACTTGGAACATAGAAGATTTTGACGC GTTAATAAGTGAATTGAGGATCATTTG 3' | 4 |
| K164A Rv | 5'-CAAATGATCCTCAATTCACTTATTAACGC GTCAAAATCTTCTATGTTCCAAGTCAG 3' | 5 |

—Cell Culture.

All cells were cultured in a humidified incubator at 37° C. with 5% $CO_2$. SCC-25 (ATCC® CRL-168™) and patient-derived cells (VDH-00, VDH-01 and VDH-02) were grown in keratinocyte serum-free media (KSFM, GIBCO) supplemented with 5 μg ml$^{-1}$ penicillin/streptomycin, 0.025 mg ml$^{-1}$ bovine pituitary extract and 0.2 μg ml$^{-1}$ of hEGF. JHU-029 cells (The Johns Hopkins University) were grown in RPMI (GIBCO) supplemented with 5 μg ml$^{-1}$ penicillin/streptomycin and 10% foetal bovine serum (FBS; GIBCO). FaDu (ATCC® HTB-43™) and Detroit (ATCC® CCL-138™) cells were grown in EMEM (LONZA) supplemented with 5 μg ml$^{-1}$ penicillin/streptomycin and 10% FBS (GIBCO). MCF-7 cells (ATCC® HTB-22™) were grown in EMEM (LONZA) supplemented with 5 mg ml$^{-1}$ penicillin/streptomycin, 0.01 mg ml$^{-1}$ human recombinant insulin and 10% FBS (GIBCO). The 501mel human cell line (kindly provided by Dr. Claudia Wellbrock, Manchester Cancer Research Centre, The University of Manchester, UK) was grown in DMEM supplemented with 5 mg ml$^{-1}$ penicillin/streptomycin and 10% FBS (GIBCO). HNACFS (Head and Neck tumour associated fibroblasts) were grown in DMEM supplemented with 5 mg ml$^{-1}$ penicillin/streptomycin, 10% FBS (GIBCO) and 1× insulin transferrin selenium G supplement (Invitrogen). OP9 cells were cultured and differentiated to adipocytes as previously described (Wolins et al., 2006). Briefly, cells were cultured and amplified in MEM alpha medium+glutaMAX™ (MEM-α, GIBCO) supplemented with 20% FBS (GIBCO) and 5 mg ml$^{-1}$ penicillin/streptomycin. To differentiate them to adipocytes, OP-9 cells were grown to confluency and then cultured for 2 additional days in MEM-α supplemented with 15% of KnockOut™ Serum Replacement (GIBCO) and 5 mg ml$^{-1}$ penicillin/streptomycin. For co-culture experiments, SCC (OSCC) cells were seeded over confluent adipogenic OP9 for 12 to 48 h at 37° C. with 5% $CO_2$. PhoenixA and 293T cells grown in DMEM/10% FBS were used for retrovirus and lentivirus production, respectively, after transfection with the $CaCl_2$ method. To select, 2.5 mg ml$^{-1}$ puromycin or 0.3 mg ml$^{-1}$ G418 was added to the media. All cell lines tested negative for mycoplasma contamination. For label-retaining experiments, cells were trypsinized with trypsin-EDTA 0.25% (GIBCO), washed twice in 1× PBS and incubated with Vybrant® DID (Molecular Probes, V-22887) at a 1:200 dilution in 1×PBS for 20 min at 37° C. After incubation, cells were washed twice with 1× PBS to remove excessive dye. Note that the dye homogeneously coated all cells in culture and was undetectable by FACS after an average of eight cell divisions. For palmitic acid OSCC treatment, sodium palmitate (P9767, SIGMA) was prepared as a 2.5 mM stock solution by dissolving it in 1 ml of 0.1M NaOH and warming at 80° C. until clear. The fatty acid solution was complexed with fatty acid-free BSA (A7030, SIGMA) in a molar ratio fatty acid/BSA of 5:1; briefly, 0.325 g of BSA was dissolved in 8 ml 0.9% NaCl, and the mixture was warmed to 45° C. The clear solution of palmitate was added drop-by-drop by pipet with agitation. The final stock solution was filtered at 0.45 q, aliquoted and stored at −20° C. OSCC cells growing in serum-free media were treated in vitro with 0.4 mM of palmitate for 48 h. For antibody pre-treatment, cells were collected by trypsinization with trypsin-EDTA 0.25% (GIBCO), washed twice in 1× PBS and incubated with neutralizing anti-CD36 JC63.1 (CAYMAN, CAY-10009893-500) at 100 μg ml$^{-1}$, anti-CD36 FA6-152 at 50 μg ml$^{-1}$ (Abcam, ab17044) or the corresponding isotype controls mouse IgA, kappa [S107](Abcam, ab37322) at 100 μg ml$^{-1}$ or mouse IgG1 NCG01 (Abcam, ab81032) at 50 μg ml$^{-1}$, suspended in 1× PBS at 37° C. for 2 h. Cells were then washed twice with 1× PBS to remove excess of antibody. All antibodies were azide-free with no added preservative compound. For intra-tongue injection of SCC (OSCC) cells, cultured cells were trypsinized with trypsin-EDTA 0.25% (GIBCO) diluted in PBS/Trypan Blue, counted in a Neubauer chamber and resuspended in 1× PBS. For SCC-25 and JHU-029 cells, 100,000 cells per mouse were injected; for FaDu, Detroit-562 and patient-derived cells, 50,000 cells per mouse were injected. For limiting dilution assays, serial dilutions (50,000, 20,000, 10,000, 1000 or 100 cells) of sorted $CD44^{bright}$, $CD36+CD44^{bright}$ or $CD36-C44^{bright}$ OSCC cells were injected immediately after sorting into the tongue of NSG mice. For intravenous injection, 100,000 in 1× PBS cells were injected by retro-orbital injection. Mice were monitored by bioluminescence determination for positive response of primary tumour and/or metastasis growth. The active cell frequency of tumour-initiating cells or metastasis-initiating cells was estimated by statistical analysis at 60 days after injection (humane endpoint) using the ELDA software (Extreme Limiting Dilution Analysis, bioinf.wehi.edu.au) (Goel et al., 2013).

The fatty acid uptake assay was performed according using the QBT Fatty Acid Uptake Assay Explorer Kit (Molecular Devices), according to manufacture's instructions. Briefly, OSCC cells were grown in adipogenic-conditioned media for 72 h and collected, and seeded in a 96-well-plate, at a density of 50,000 cells per well, with 100 mB adipogenic-conditioned media. After 24 h, cells were deprived of serum and incubated for 1 h at 37° C. with 5% $CO_2$. Plates were read using a Biotek FL600 Fluorescence instrument, bottom reading, medium sensitivity (150), excitation 488/emission 515, and a filter cut-off of 495 nm —Tumour Disaggregation from Xenografted Mice.

Tumours were isolated from mice, and connective tissue was removed as much as possible. Tissue was chopped in 0.5% trypsin 1-300 (MP Biomedical) in KSFM media (GIBCO) in a McIlwain Tissue Chopper. After complete homogenization, samples were incubated at 37° C. for 90 min with shaking. Homogenates were filtered sequentially in 100 µm, 70 µm and 40 µm BD strainers and centrifuged at 1000 rpm for 10 min at 4° C. Supernatant was discarded, and each pellet was resuspended in 1× PBS/4% calcium chelated FBS (Calon et al., 2012) for antibody staining and subsequent FACS analysis.

—FACS-Sorting Analysis.

For xenografts (orthotopic transplants) analysis, samples were incubated for 45 min at RT with anti-CD36-PercP-EFluor 710 (ref. 46-0369-41, E Bioscience) and anti-CD44-PeCy7 (CD44 Clone GG-26, ref. 560533, BD Pharmigen) at 1:100 dilution, and, to exclude contaminant mouse cells, a lineage-negative cocktail conjugated to biotin composed of anti-CD31 clone MEC13.3 (ref. 553371, BD Pharmigen, 1:200 dilution), anti-CD45 clone 30-F11 (ref. 13-045-81, eBioscience, 1:200 dilution), anti-H2Kd (ref. 553564, eBioscience, 1:200 dilution) and the mouse Lin Cocktail (ref. 120-003-582, MACS Miltinyi Biotech, 1:20 dilution). After the first incubation, samples were washed in 1× PBS/calcium chelated FBS (Nowak and Fuchs, 2009) and spun for the second incubation with Brilliant Violet (BV) 605 Streptavidin (ref. 405229, Biolegend, 1:50 dilution) for 30 min RT and then resuspended in 1× PBS/4% calcium chelated FBS (Calon et al., 2012) with DAPI at a 1:1000 dilution for FACS analysis. To analyse the co-culture experiments of SCC (OSCC) cells with adipocytes or tumour-associated fibroblasts, samples were incubated for 45 min at RT with anti-CD36-PercP-EFluor 710 (ref. 46-0369-41, E Bioscience) as well as with a mouse/rat anti-CD29-APC, clone HMb1-1 (ref. 1002216) to exclude adipocytes. Unstained and single-color controls were used in each case.

Samples were analysed in a BD FACS ARIA FUSION instrument. For FACS sorting, cells were selected on the basis of their Forward and Side scatter excluding cellular debris. Doublets and dead cells were eliminated by DAPI or propidium iodide (PI). GFP-positive cells were gated excluding the Lineage-BV positive cells. This population was selected for further analysis or directly for injection in the tongue of the mice.

Fatty acid-oxidation enzymes were measured by flow cytometry with the Fatty Acid Oxidation Human Flow Cytometry Kit (Abcam, ab118183), according to the manufacturer's specifications.

—Immunofluorescence and Histological Analysis.

Cryo- or de-paraffinized antigen retrieved sections (10 min in boiling 0.01M citric acid, pH 6.0) of 8 µm were permeabilized for 25 min in 0.25% TRITON™ X-100/PBS and blocked for 90 min in 0.25% gelatin/PBS. Primary antibodies were incubated overnight at 4° C. and secondary antibodies were incubated 2 h at room temperature in 0.25% gelatin/PBS. Nuclei were stained with DAPI (1:5000, Roche), and slides were mounted in Mowiol. The primary antibodies used were rat anti-CD44 at 1:100 (eBioscience), rabbit anti-caspase3 (abcam, ab13847) and rabbit anti-GFP at 1:1000 (Life Technologies). DID (D-7757, Molecular Probes) and DIL (D-3911, Molecular Probes) dyes were analysed by direct immunofluorescence. The secondary antibodies used were Alexa Fluor conjugated (R37118, A-11006, A-10042, A-11077, Molecular Probes). For neutral lipid droplets visualization, frozen cryosections were stained with bodipy 558/568 $C_{12}$ (Molecular Probes, D-3835) as previously described (Spangenburg et al., 2011). Hematoxilin and eosin (H&E) staining was done according to the standard protocol. Images were acquired using a Nikon E600+Olympus DP72, Leica SPE and a Leica TCS SP5 confocal microscope. Representative pictures were selected in each case.

—Gene Expression Analysis.

RNA isolation and cDNA amplification was performed as described by Gonzalez-Roca et al. (Gonzalez-Roca et al., 2010). In brief, cells were sorted into lysis buffer and RNA was purified using magnetic beads (RNAClean XP beads, Agencourt). RNA was reverse transcribed and cDNA was amplified using Whole Transcriptome Amplification chemistry (WTA2, Sigma Aldrich). For monitoring amplification, SYBR Green was added to the reaction; it was stopped when SYBR Green signal reached a plateau. cDNA was purified using Purelink Quick PCR purification kit (Invitrogen). cDNA was labeled using GeneChip Mapping 250K Nsp Assay Kit (Affymetrix; catalog #900766), according to manufacturer's instructions. Affymetrix PrimeView arrays were hybridized with 8 mg of labeled cDNA, washed, stained and scanned according to the protocol described in GeneChip® 3' IVT Express Kit User Manual. Arrays were scanned with GeneChip scanner 3000 (Affymetrix, Santa Clara, CA). Normalized expression signals were calculated from Affymetrix CEL files using RMA algorithm (Irizarry et al., 2003). Log2 RMA expression was estimated.

For Agilent microarrays, total RNA was extracted from FACS sorted cells with RNAClean XP kit-Agentcourt A63987 following the manufacturer's instructions and immediately amplified using the TransPlex Complete Whole Transcriptome Amplification Kit (Sigma WTA2) to generate the cDNA. Cyanine-3 (Cy3) labeled cDNA was prepared from 500 ng of ds cDNA using the DNA Enzymatic Labeling kit (Agilent 5190-0449) according to manufacturer's instructions followed by column purification (Amicon 30 kDa). Dye incorporation and cDNA yield were checked with the NanoDrop ND-1000 Spectophotometer. Arrays were scanned with an Agilent G2539A scanner at 3 um resolution and 100% PMT. The intensity data of the individual hybridizations was extracted and the quality was assessed with the Feature Extraction software 10.7 (Agilent). Raw data was corrected for background noise using the normexp method. Quantile normalization was applied to assure comparability across samples. Normalized log 2 intensity values were estimated. The relative −log2 ratios of DiD−/DiD+, DiD−/CD44$^{dim}$ and DiD+/CD44$^{dim}$ were calculated respectively, and genes were filtered based on the −log2 ratio DiD−/DiD+ equal to or greater than 1.5; $P \leq 0.005$.

For the gene expression analysis comparing the transcriptome of CD36+ and CD36− cells, all analyses were performed using R (Dean and Nielsen, 2007) and Bioconductor (Gentleman et al., 2004). Affymetrix microarrays were processed using RMA normalization as implemented in the Bioconductor R package affy (Gentleman et al., 2004). Annotation was performed using probeset information provided by Affymetrix in its product support web (www.affymetrix.com downloaded in 19/09/2014). Differential expression analysis between CD36+ and CD36− samples was carried out at the probeset level using moderated t-statistics by empirical Bayes shrinkage as implemented in the limma R package (Smyth G, 2005). For doing so, paired differences within biological replicates were computed and a linear model was fitted to them using replicate as covariate (functions duplicate Correlation and lmFit) (Smyth G, 2005). Benjamini and Hochberg correction (Benjamini Y, 1995) was applied for multiple contrast adjustment. Geneset Enrichment Analysis (GSEA) (Subramanian et al., 2005) was used to assess the enrichment of a fatty acid metabolism geneset from the Hallmark geneset collection provided by the Broad Institute Molecular Signature Database (MsigDB-H; KEGG FATTY ACID METABOLISM; downloaded in 15/07/2015) (Chen et al., 2011). In these analyses, data (probesets) were collapsed to the gene level by selecting the probeset showing the highest standard deviation within each gene. Genes were ranked according to the absolute value of their limma t-statistic and, thus, according to the fold changes between conditions.

Genomatix software suite v3.4 (www.genomatix.de) (Berriz et al., 2003) was also used for gene ontology and pathways analysis. Using the Genomatix Software, pathways analysis is based on data mining of PubMed, referring to Biocarta, STKE or KEG. The complete dataset was deposited to the National Center for Biotechnology Information Gene Expression Omnibus Database (GEO) (Barrett et al., 2006) and are accessible through accession number GSE72939.

—Real-Time PCR.

Real-time PCR using TaqMan gene expression probes (Applied Biosystems, see Table 2 for the assay identification corresponding to each probe) was performed and analysed using a 7900-HT Fast Real-Time PCR Instrument (Applied Biosystems). Relative expression levels were determined by normalization to beta-2-microglobulin (b2m) using the $\Delta\Delta C_t$ method.

TABLE 2

Assay identification of Taqman probes used in the RT-PCR

| Gene | Assay ID |
| --- | --- |
| ATF3 | Hs00231069_m1 |
| ATP6V0A4 | Hs00220986_m1 |

TABLE 2-continued

Assay identification of Taqman probes used in the RT-PCR

| Gene | Assay ID |
| --- | --- |
| B2M | Hs00187842_m1 |
| CARD18 | Hs01043258_m1 |
| CCNA2 | Hs00996786_m1 |
| CCNB | Hs01030099_m1 |
| CCL5 | Hs00982282_m1 |
| CD36 | Hs01567185_m1 |
|  | Hs01567195_m1 |
| CDKN1A | Hs99999142_m1 |
| CFLAR | Hs00153439_m1 |
| FBXO32 | Hs01041408_m1 |
| HMOX1 | Hs01110250_m1 |
| ID1 | Hs03676575_s1 |
| IGFBP3 | Hs00426289_m1 |
| JUNB | Hs00357891_s1 |
| KLK6 | Hs00160519_m1 |
| MMP9 | Hs00234579_m1 |
| MYEOV | Hs00993153_g1 |
| POSTN | Hs01566734_m1 |
| PTGES | Hs01115610_m1 |
| S100A7 | Hs00161488_m1 |
| S100A8 | Hs00374264_g1 |
| S100A9 | Hs00610058_m1 |
| SH3BP2 | Hs00610068_m1 |
| SPRR1B | Hs00234164_m1 |
| Sox9 | Hs01001343_g1 |
| SPARC | Hs01076127_m1 |
| AQP3 | Hs01105469_g1 |
| EPHA2 | Hs00171656_m1 |
| LIPH | Hs00975890_m1 |
| ACSL1 | Hs00960561_m1 |
| CPT1A | Hs00912671_m1 |
| CPT2 | Hs04188816_m1 |
| HADHA | Hs00426191_m1 |
| HADHB | Hs01027271_m1 |

—Bioinformatics Analysis.

The Data from the TCGA project was downloaded from the cbioportal (Gao et al., 2013; Cerami et al., 2012). Expression data computed as mRNA z-Scores (RNA Seq V2 RSEM, Agilent) were compared to the expression distribution of each gene tumours that are diploid for this queried gene. For luminal A breast cancer was used the staging information mapped to the 7th edition as reported in [doi: 10.1038/nature11412]. Stage subclassifications were collapsed to stages I, II, III and IV. Expression of the gene signature was computed by averaging all genes in signature for each patient. Both the C36 and signature expressions were scaled before fitting the model. A Cox model was fitted to overall survival and disease free survival data with stage, gender, age and histological subtype as covariates. Significance of the association between expression and survival was assessed with a Likelihood Ratio Test as implemented in the R function "drop1".

—Statistical Analysis.

For all the experiments, adequate sample size was determined based on results of pilot studies. No statistical method was used to determine sample size. All the animals that fulfilled proper experimental conditions during the experimental procedures were included in the analysis. Based on results of pilot studies, homogeneous groups of males and females between 8 and 10 weeks and their control littermates were used for the experimental studies. No statistically differences were found regarding the gender of mice and no randomization method previously described was used. Data are generally shown as the mean±s.e.m. Statistical significance was analyzed using Prism 6 software (GraphPad) by using a two-tailed t-test, Mann-Whitney U test, Fisher exact test or hypergeometric test. Significance was considered at P<or equal 0.05.

Example 1.—Identification of a Low Proliferative Subpopulation in OSCCs

An orthotopic model of human OSCC was used to study the cell cycle heterogeneity of tumour cells in vivo (Myers et al., 2002).

To determine whether OSCCs harbour a low proliferative subpopulation of cancer cells in vivo, the inventors first implanted human OSCC cells from established cell lines (SCC-25, FaDu, Detroit-562 and JHU-029) or from primary tumour samples (VDH-00, VDH-01 and VDH-02), transduced with a retroviral vector expressing luciferase and the green fluorescent protein (Luc-GFP), into the tongue of immunosuppressed NOD-SCIDγ mice (NSG). All cell lines and patient-derived cells (PDCs) generated primary tumours with 100% penetrance, albeit with different growth kinetics. Table 3 shows the relevant data.

TABLE 3

Generation of primary tumours from implanted cell lines or tumour samples

| SCC cell line | % developed Primary tumours | % developed Metastasis (LN) | Time until develop metastasis | Site of metastasis |
| --- | --- | --- | --- | --- |
| FaDu | 100 | 91 | 1 week | Lymph node, Lung |
| Detroit-562 | 100 | 81 | 1 week | Lymph node |
| SCC-25 | 100 | 25 | 1.5 weeks | Lymph node |
| JHU-029 | 100 | 15 | 1.5 weeks | Lymph node |
| VDH-00 | 100 | 10 | >2.5 weeks | Lymph node |
| VDH-01 | 100 | 45 | >2.5 weeks | Lymph node |
| VDH-02 | 100 | 60 | 1.5 weeks | Lymph node |

Interestingly, this orthotopic model of OSCC recapitulated the metastatic spread to the lymph nodes (LNs) that occurs in patients. However, the penetrance of LN colonization between different tumour cells was much more variable than the primary tumour growth, with some tumour cells displaying very high (FaDU, Detroit-562, VDH-02), intermediate (VDH-01, SCC-25), or low (JHU-029, VDH-00) metastatic potential. Only FaDU cells generated lung metastasis. Note that the comparative ability of these cell lines and PDCs to promote metastasis was independent of the size of the primary tumours they developed.

Figure 1B:
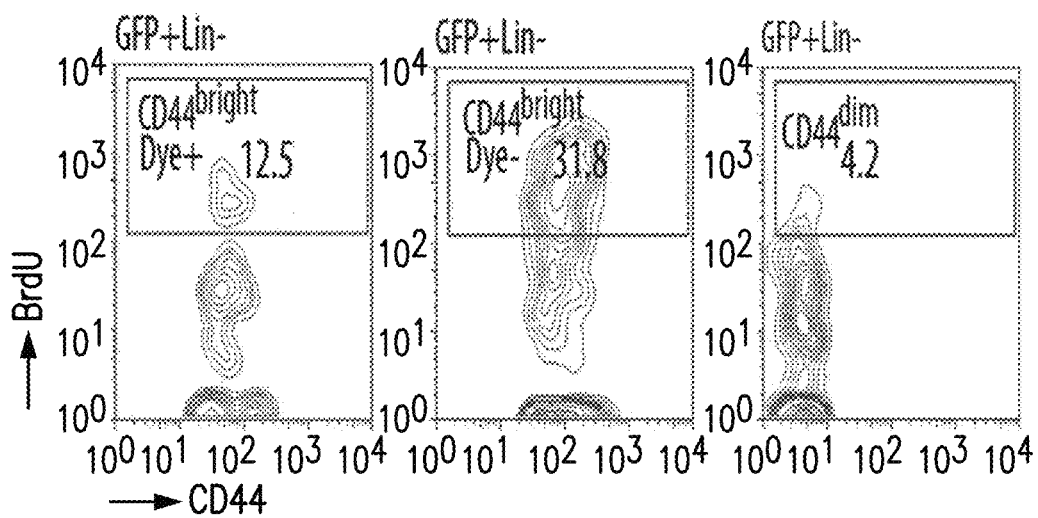

To study cell cycle heterogeneity in vivo, the inventors pulsed each Luc-GFP transduced cell line and PDCs in culture with a highly stable, non-toxic, lipophilic fluorescent dye (DID) that non-specifically binds to membranes and is diluted upon cell division (Yumoto et al., 2014). The dye homogeneously coated all the cells in culture, and was undetectable by FACS after an average of eight cell divisions. When pulsed tumour cell lines or PDCs were injected orthotopically in the oral cavity of NSG mice, the authors observed a small percentage of $CD44^{bright}$ long-term label-retaining cells (LRCs) within the generated oral lesions (FIG. 1A). LRCs were also visualized by direct fluorescence within the tumour cells expressing the highest levels of CD44. Pulses of BrdU 24 h prior to collecting the oral tumours confirmed that the $CD44^{bright}$/dye+ population was less proliferative in vivo than its $CD44^{bright}$/dye− counterpart (FIG. 1B). Thus, the $CD44^{bright}$ population, previously known to have the strongest tumour-initiating potential in OSCC, displays cell cycle heterogeneity in vivo.

Figure 1C:
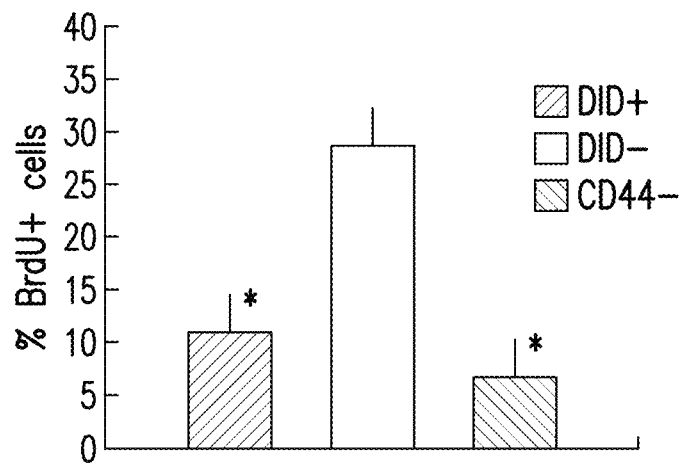
Figure 1D:
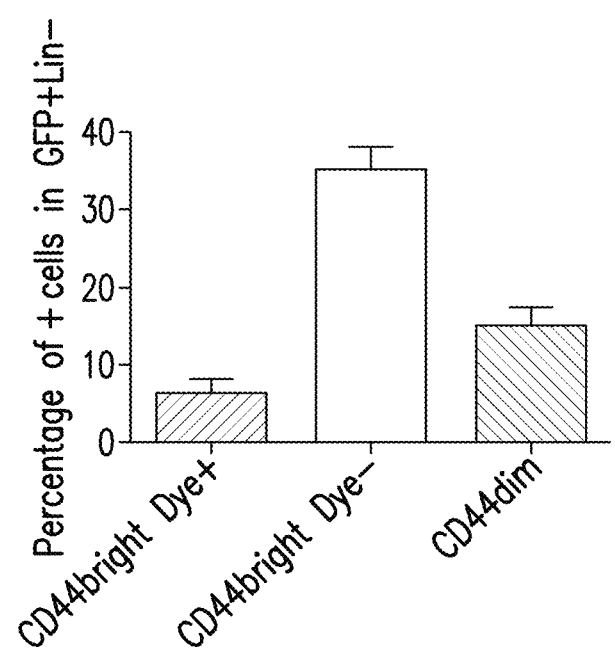
Figure 1E:
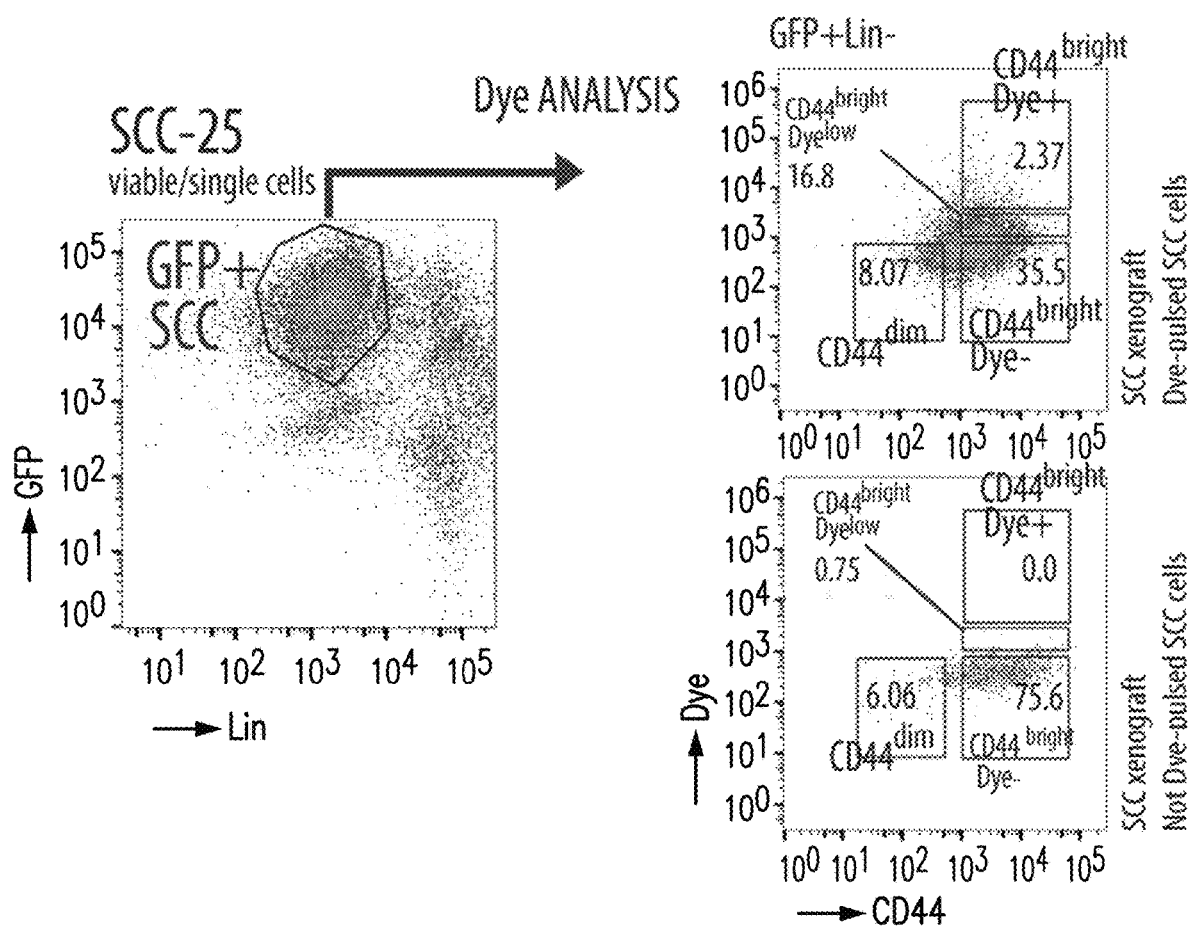

Then, the molecular signatures that define each tumour population were investigated on the basis of their dye retention and CD44 expression. The inventors FACS sorted $CD44^{bright}$/dye+(LRCs), $CD44^{bright}$/dye− (non-LRCs), and $CD44^{dim}$ cells (differentiated tumour mass) from SCC-25-derived orthotopic tongue tumours, and obtained their transcriptome by human specific microarrays. The transcriptome of LRCs and dye− cells was more similar between them than to the one defining the differentiated $CD44^{dim}$ population (FIG. 1C). However, a significant number of genes were differentially expressed between LRCs and dye− cells. Gene Ontology (GO) analysis indicated that the dye− signature is characterized by chromosomal instability, cell transformation, and neoplasm, and contained genes involved in cell cycle and cell division, as expected of a highly proliferative tumour population. However, while the signature of LRCs was also indicative of carcinoma cells, it included an over-representation of genes associated to lymphatic metastasis and neoplasm metastasis, which were not present in the dye− counterparts. This signature included SPARC, TNFSF10, POSTN, PTGES, S100A8 and S100A9, all of which have been reported to promote metastasis in other types of tumours. Interestingly, LRCs were characterized by a large number of genes related to response to lipids, and lipid metabolic process, as well as pathways involved in Interleukin-1, CD36 molecule, PPARgamma, MMPs, TGFbeta, and Ras GTPases signaling.

Figure 2:
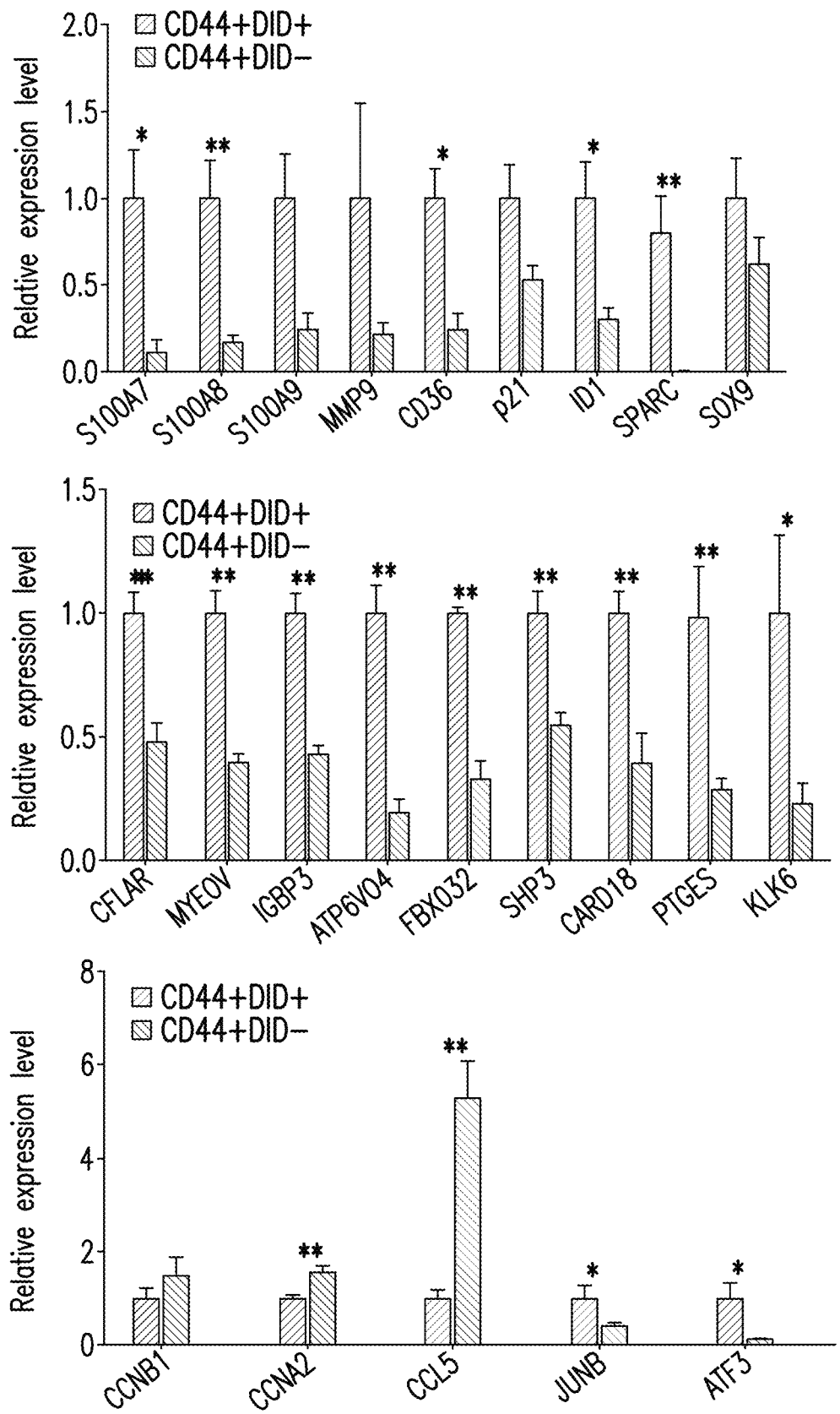
FIG. 2. RT-qPCR validation by human specific TaqMan gene expression assays of differentially expressed genes in the CD44+DID+ and CD44+DID− populations. Data are given as relative expression levels. n=5, P*<0.05, P**<0.005, two-tailed t-test.

The differential expression of several of these genes was validated by RT-qPCR in five biological replicates (FIG. 2). Altogether, these results suggested that LRCs might constitute a pro-metastatic population of tumour cells present in the primary oral lesion.

Figure 3A:
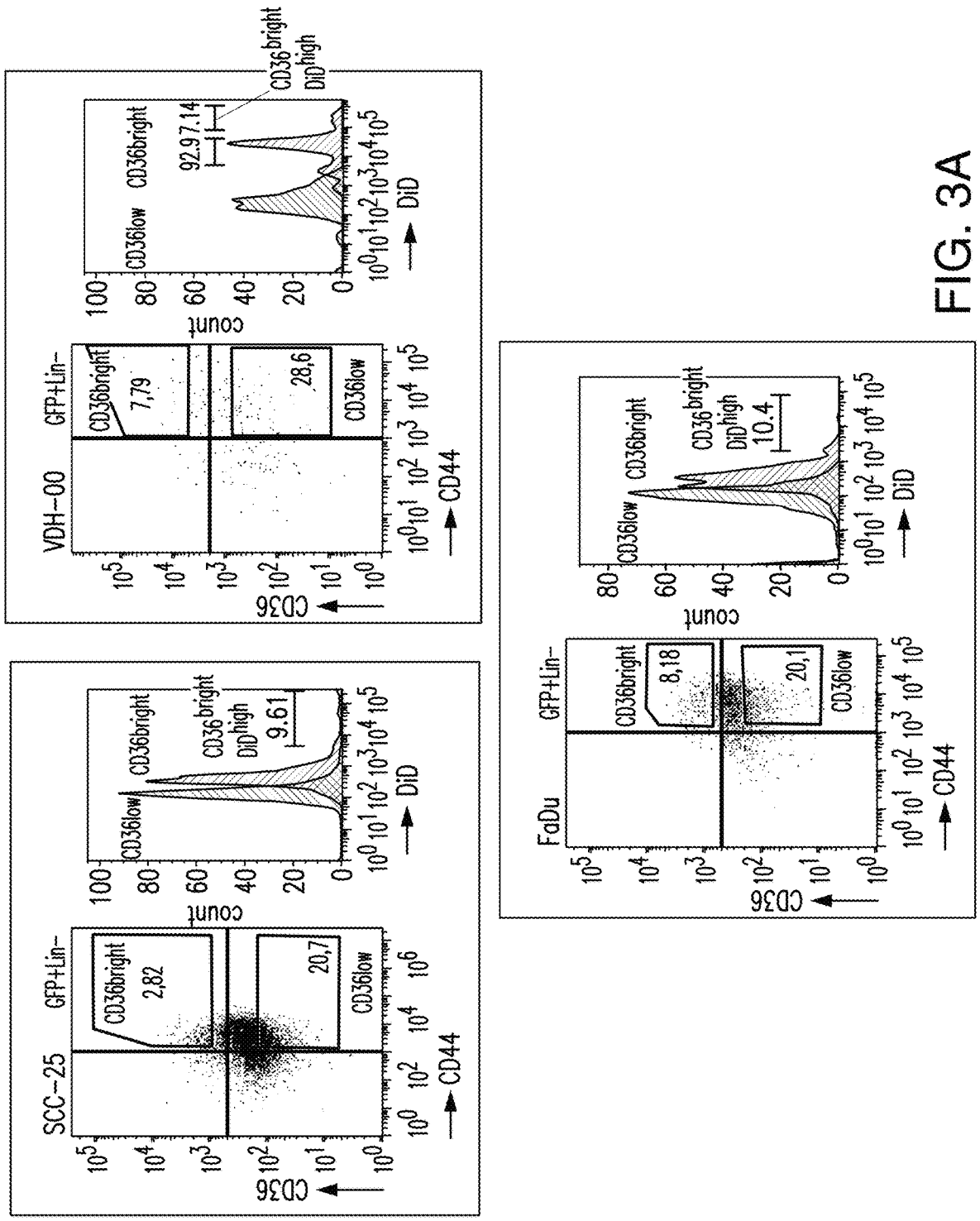
FIGS. 3A-3N. OSCC LRCs express high levels of CD36, and modulating CD36 expression strongly affects the penetrance and growth of lymph node metastases.
Figure 3B:
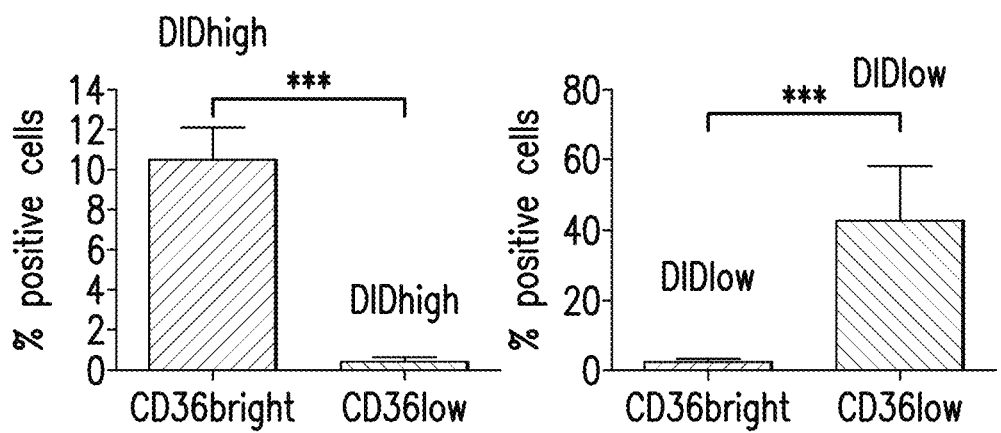
FIG. 3B, Quantification of the correlation between CD36 expression and DID content for SCC-25, JHU-029, Detroit-562, FaDu, VDH-00, VDH-01 and VDH-02 xenografts (n=8 animals per cell line). Numbers indicate percentages from the total GFP+Lin− SCC parental tumour. Results are representative of 3 independent experiments (n=3), P=0.0008, P=0.03, two-tailed t-test.
Figure 3C:
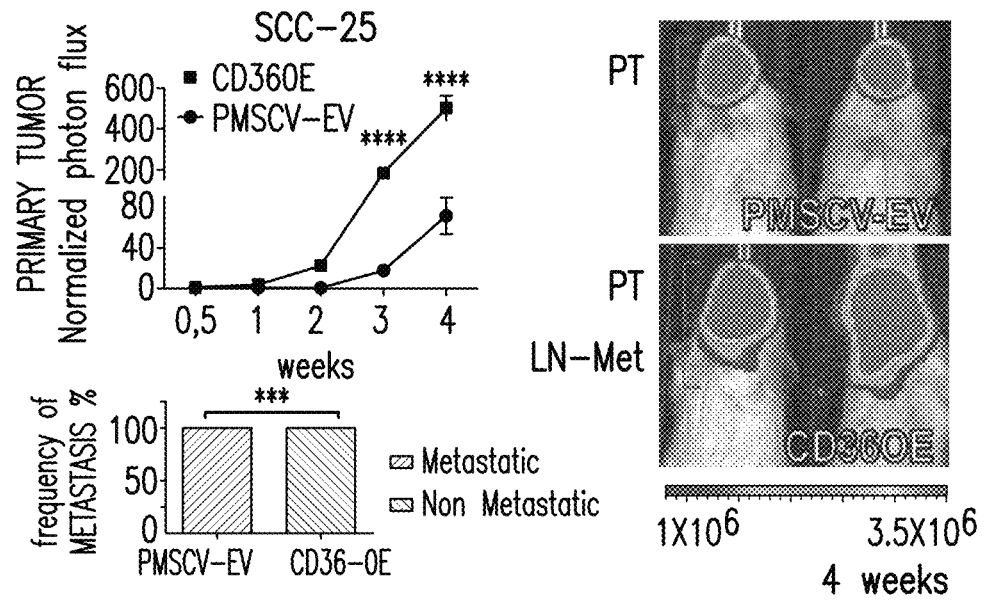
FIG. 3C, FIG. 3D, Bioluminescent monitoring of PMSCV-EV (empty vector) and CD36-OE (over-expression) tumours of SCC-25 (FIG. 3D) (PMSCV-EV, n=7; CD36-OE, n=17) and VDH-00 (FIG. 3D) (PMSCV-EV, n=7; CD36-OE, n=8) xenografts, P<0.0001, two-tailed t-test. Lower graphs show the frequency of developed metastasis in mice expressed as percentages, P=0.0003; P=0.04 two-tailed Fisher exact test.
Figure 3D:
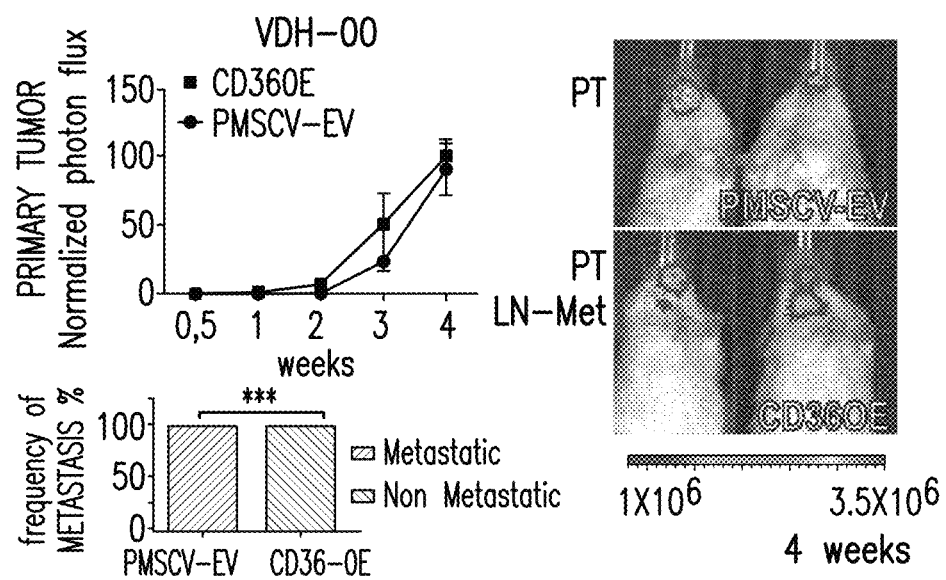
Figure 3E:
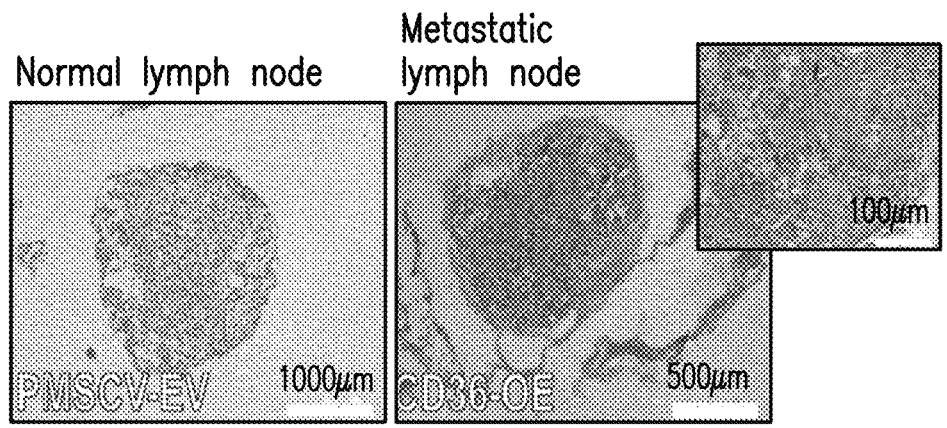
FIG. 3E, Representative haematoxylin and eosin (H&E) staining of lymph nodes from SCC-25 PMSCV-EV and CD36-OE xenografts in FIG. 3C.
Figure 3F:
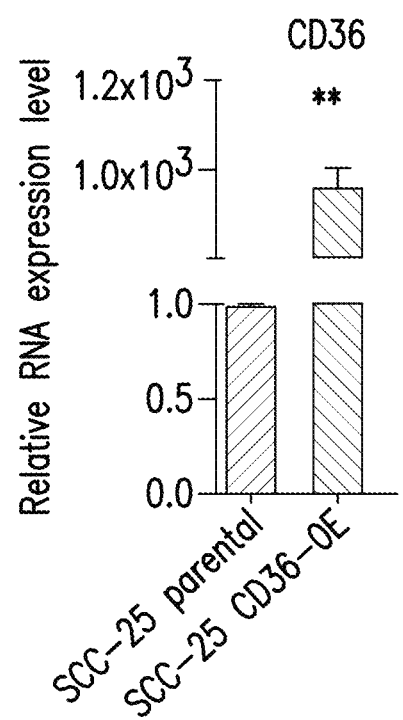
FIG. 3F, Representation of the CD36 RNA expression level found in cells of xenografts generated from SCC-25 overexpressing CD36, relative to the level found in cells from SCC-25 parental tumours.
Figure 3G:
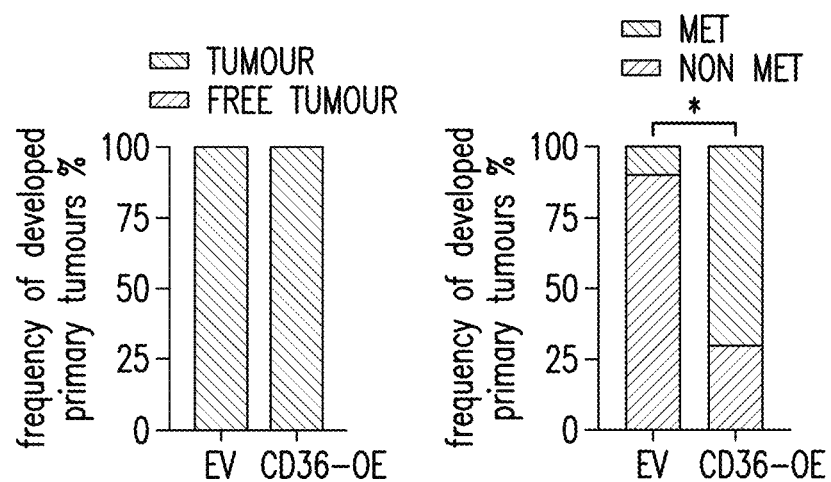
FIG. 3G, Frequency of developed primary tumours (left chart) or developed metastasis (right chart) from VDH-00 transformed with the PMSCV-EV empty vector (bars labelled "EV") or with the CD36-OE vector (bars labelled "CD36-OE".
Figure 3H:
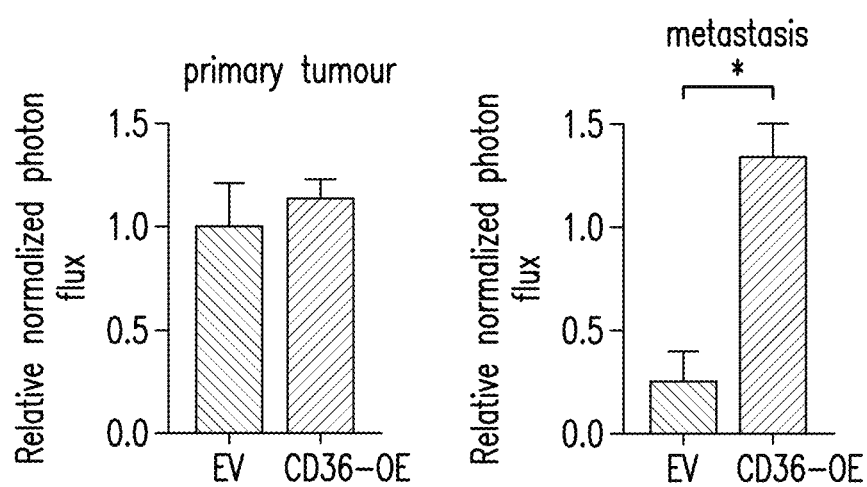
FIG. 3H, Bar charts representing the normalized photon flux observed in primary tumours (left chart) or metastasis (right chart) from VDH-00 transformed with the CD36-OE vector (bars labelled "CD36-OE"), relative to the value observed when the VDH-00 cells have been transformed with the PMSCV-EV empty vector (bars labelled "EV").
Figure 3I:
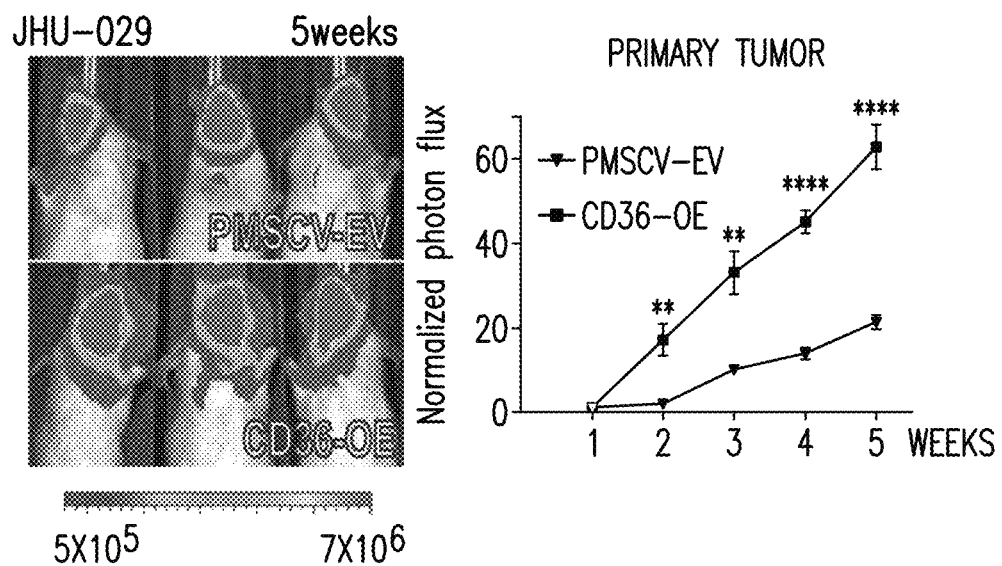
FIG. 3I, Bioluminiscent imaging (BLI) and quantification (normalized photon flux) of JHU-029 PMSCV-EV (empty vector) and CD36-OE xenografts, P=0.002; P=0.001; <0.001; <0.0001, two-tailed t-test.
Figure 3J:
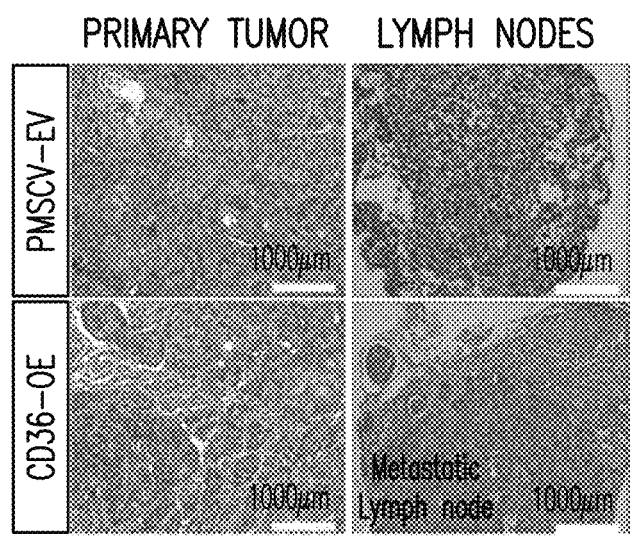
FIG. 3J, Representative haematoxylin and eosin (H&E) staining of primary tumours and metastasis from JHU-029 PMSCV-EV and CD36-OE xenografts. The inset shows a magnification of the SCC invading entirely the lymph node in the CD36-OE xenografts (n=5 animals per group).
Figure 3K:
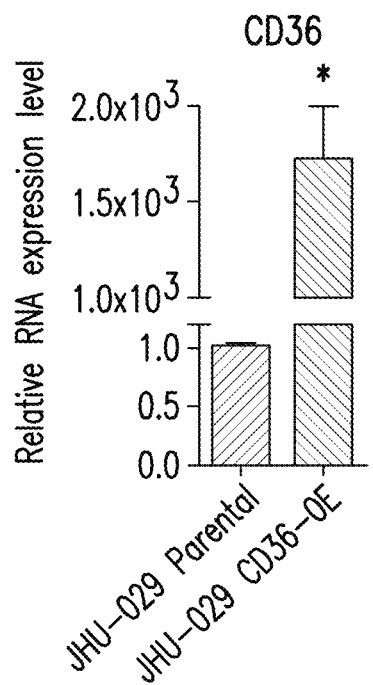
FIG. 3K, Representation of the CD36 RNA expression level found in cells of xenografts generated from SCC-25 overexpressing CD36, relative to the level found in cells from SCC-25 parental tumours.
Figure 3L:
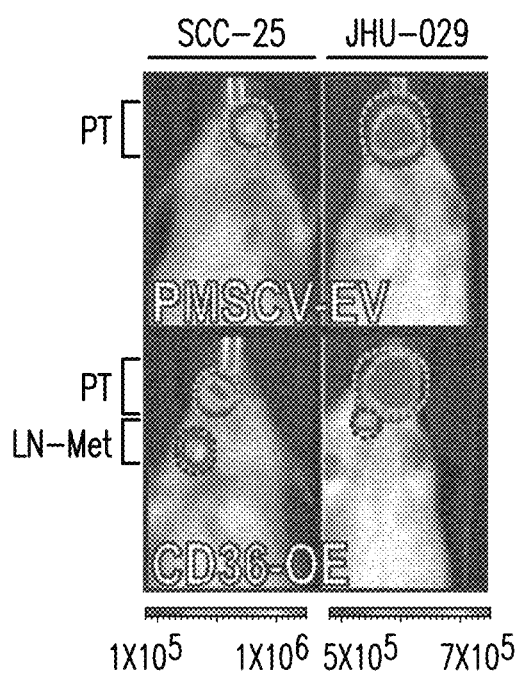
FIG. 3L, Bioluminiscent imaging (BLI) of SCC-25 (left column) and JHU-029 (right column) PMSCV-EV (empty vector) and CD36-OE (overexpression) xenografts, FIG. 3M, Frequency of developed primary tumours (left chart) or developed metastasis (right chart) from SCC-25 or JHU-029 (as indicated over the bars) transformed with the PMSCV-EV empty vector (bars labelled "EV") or with the CD36-OE vector (bars labelled "CD36-OE").
Figure 3M:
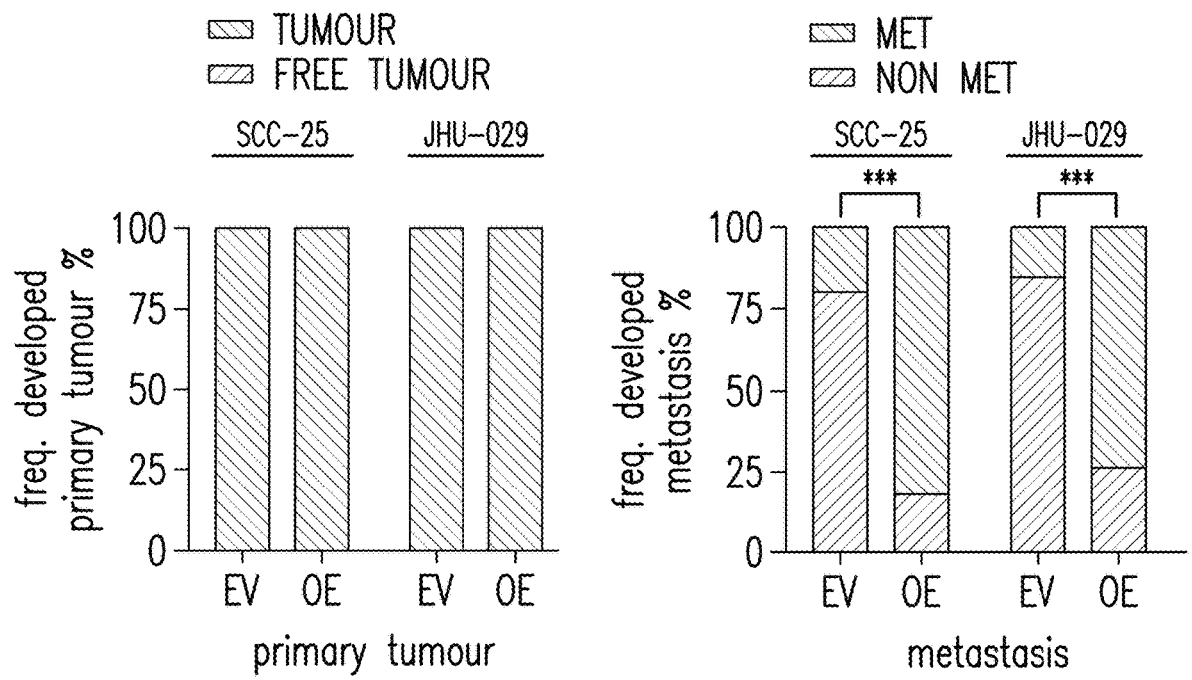
Figure 3N:
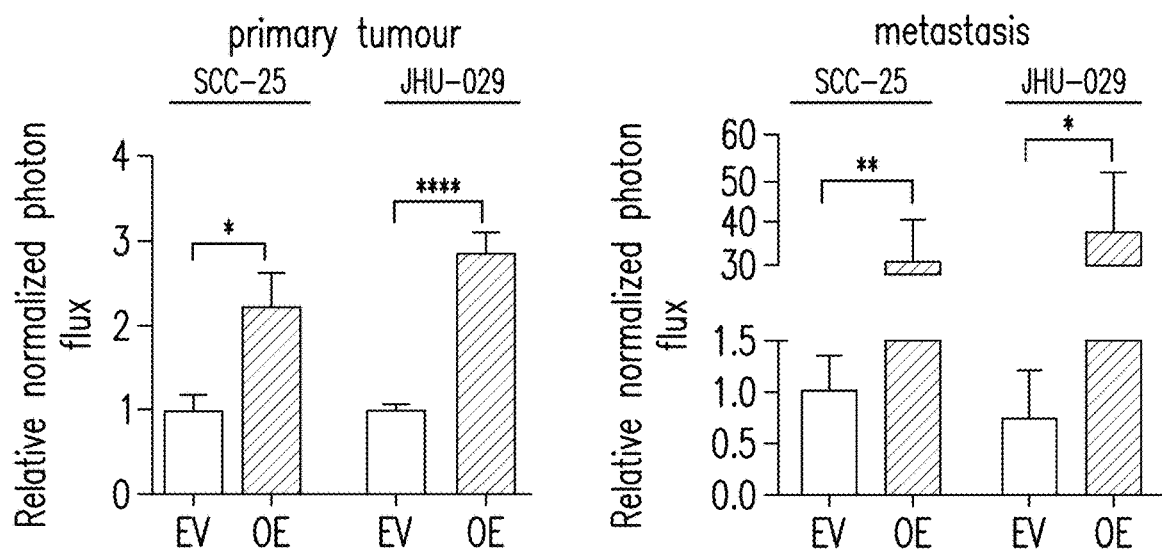
Figure 4:
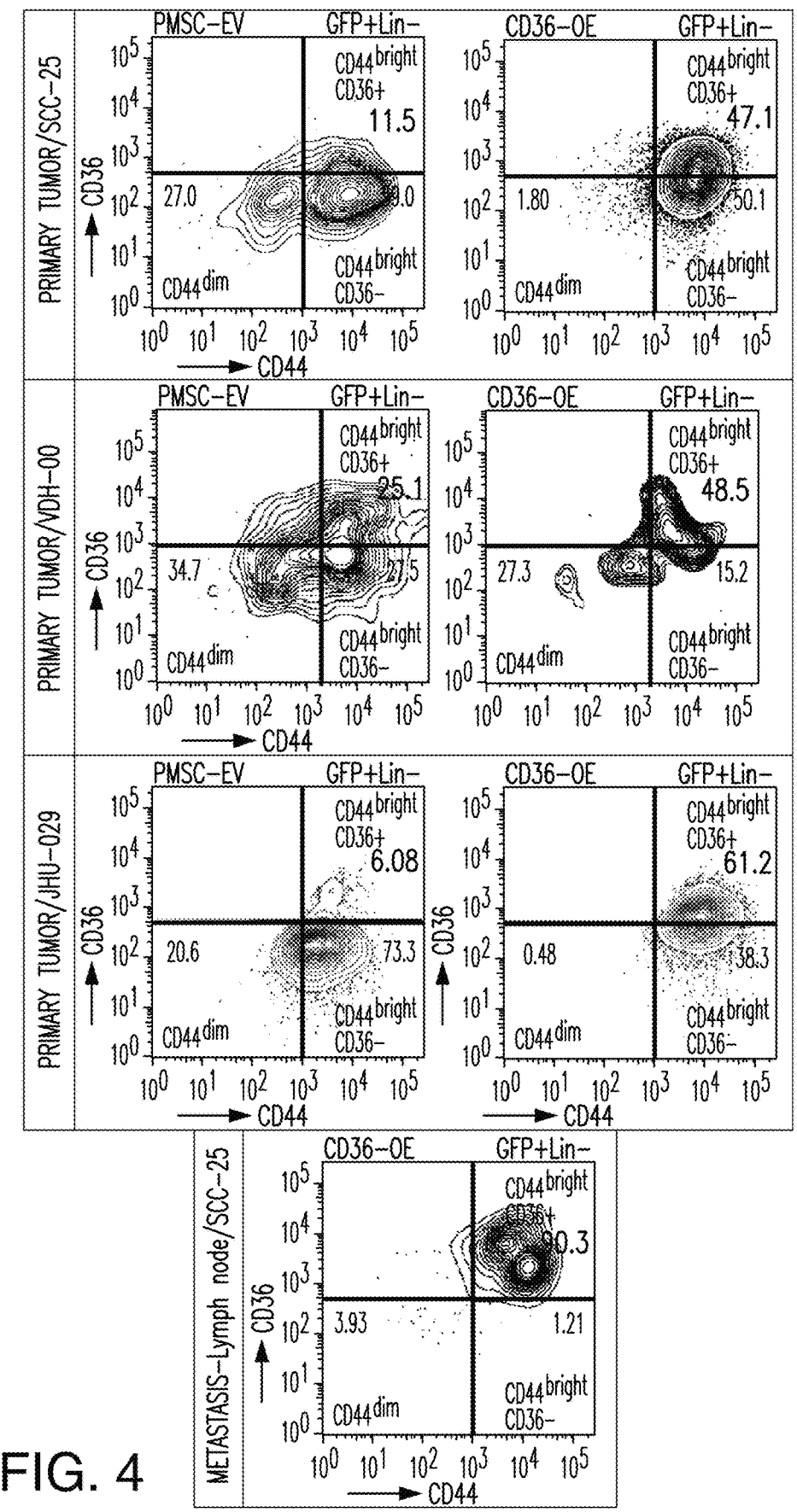
FIG. 4. Flow cytometry analysis of primary tumours from SCC-25 (top row), VDH-00 (intermediate row) or JHU-029 (lower row) PMSCV-EV (empty vector) and CD36-OE (overexpression) xenografts analysed 4 weeks after SCC injection (n=6 animals per group). For SCC-25, the analysis corresponding to lymph node metastasis is also shown (top row, on the right). Numbers indicate CD44$^{bright}$CD36+, CD44$^{bright}$CD36− and CD44$^{dim}$ (differentiated) cells in the represented gate, expressed as percentages from the total GFP+Lin− SCC parental tumour.

LRCs expressed more than 30 genes involved in fatty acid metabolism, including those in lipid uptake and transport (CD36, SCL10A1 and ABCA1), fatty acid beta- and alpha-oxidation (ACSL1, ACSBG1, PPARγ, LIPH, PLA2G4E, PNLIPRP3, PNPLA2, HSD17B2 and FA2H), lipid biosynthesis (ACSL1, ACSBG1, FA2H, HSD17B2 and CYP4F3), and intracellular lipid storage (DGAT2 and SEC14L2). The scavenger receptor CD36 was chosen for further functional and mechanistic analyses, since it is at the top of the signalling cascade that uptakes lipids from the extracellular environment and triggers their beta-oxidation to obtain energy in the form of ATP (Coburn et al., 2000; Ibrahimi et al., 1999; Pepino et al., 2014). Additionally, CD36 is a cell surface receptor that translocates fatty acids into the cell, so it could be used as a surrogate marker to detect and isolate LRCs from tumours, circumventing using fluorescent dyes. Indeed, the LRCs corresponded to the $CD36^{bright}$/$CD44^{bright}$ cells within the primary oral lesions in all cell lines and PDCs tested (Detroit-562, JHU-029, SCC-25, FaDu, VDH-00, VDH-01, VDH-02) (FIG. 3A, where the results obtained with SCC-25, VDH-00 and FaDu are shown, and FIG. 3B).

Example 2.—Metastatic Potential Associated to CD36 Expression

It was next tested whether modulating the expression of CD36 would affect the in vivo metastatic potential of OSCC tumours. CD36 overexpression in cell lines and in PDCs with low metastatic potential (SCC-25, VDH-00 and JHU-029) induced a dramatic increase in their metastatic potential to the LNs, from less than 20% to 75-80% penetrance. In addition, the LN metastases generated by OSCC tumours overexpressing CD36 were much larger (>40 fold) than in the parental cells (FIGS. 3C, 3D, 3G, 3H, 3J, 3K, 3M, 3N).

Figure 5A:
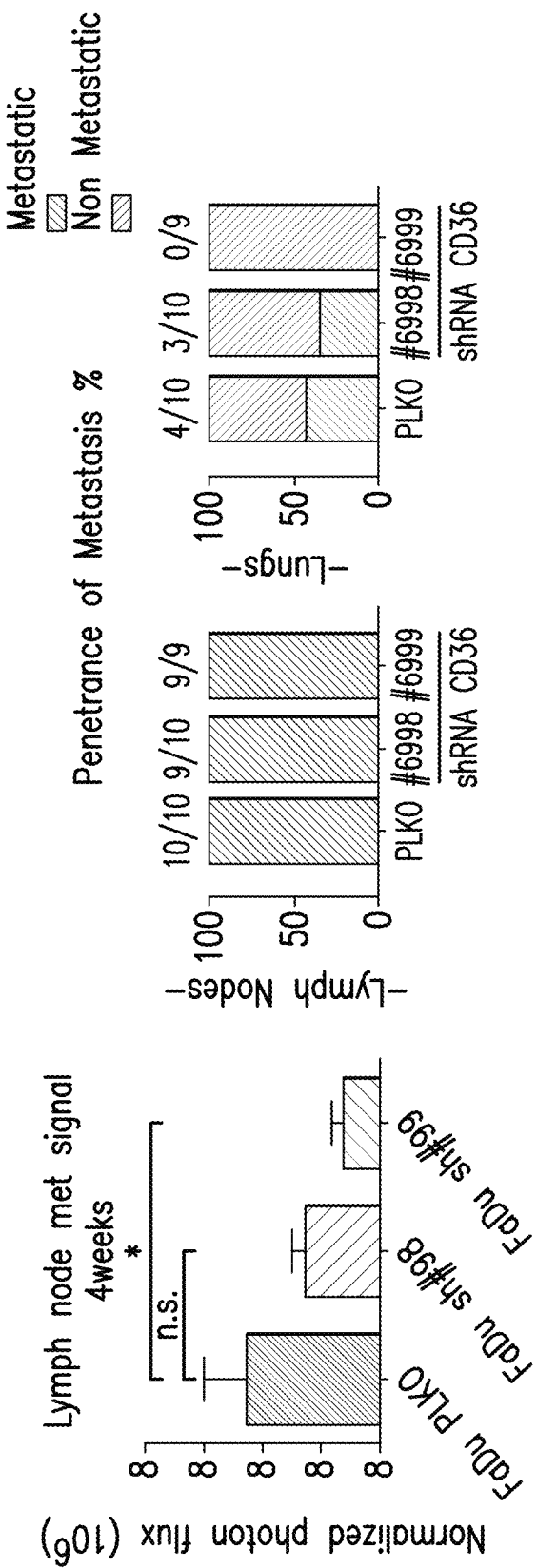
FIGS. 5A-5I.
Figure 5B:
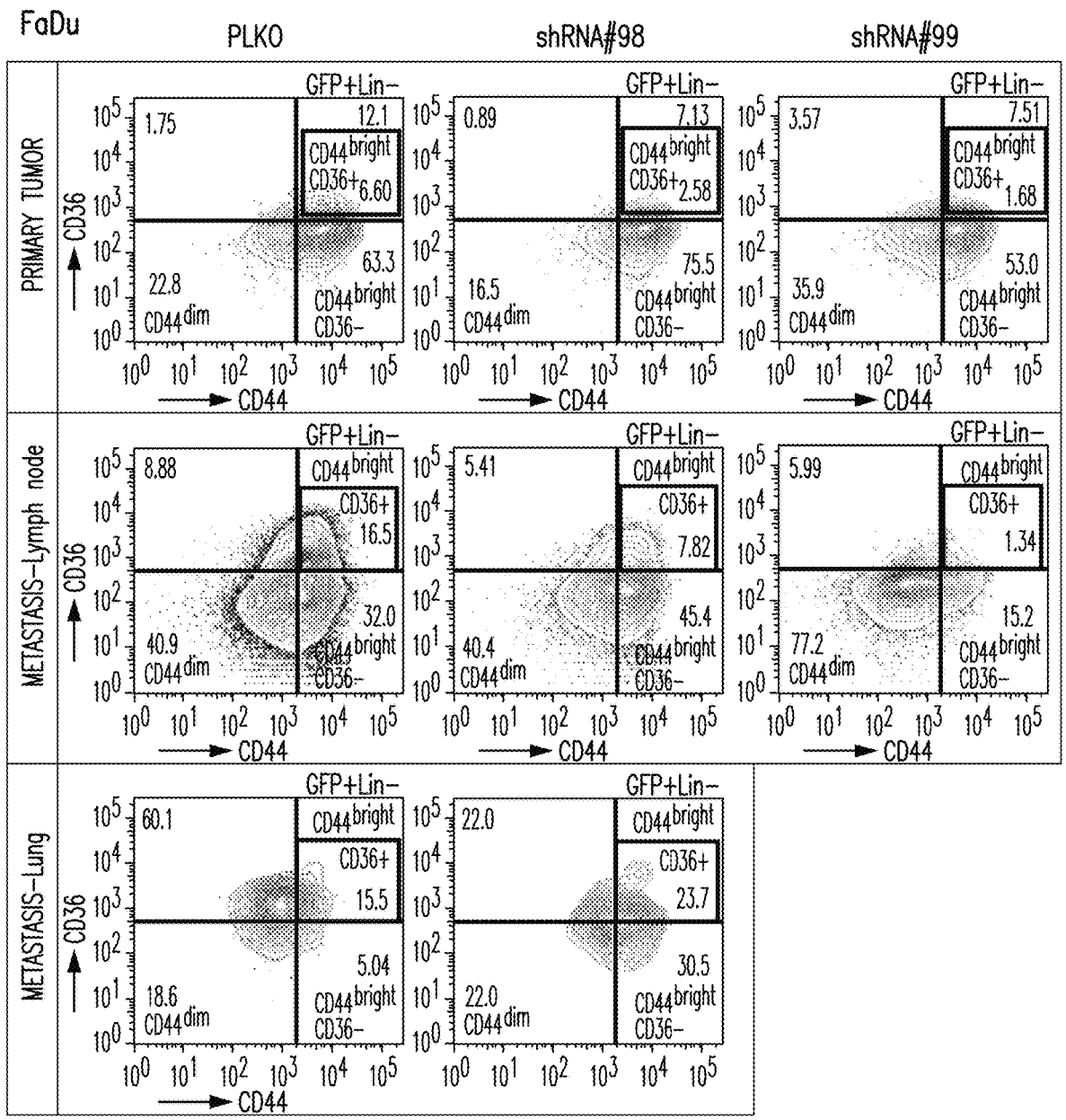
Figure 5C:
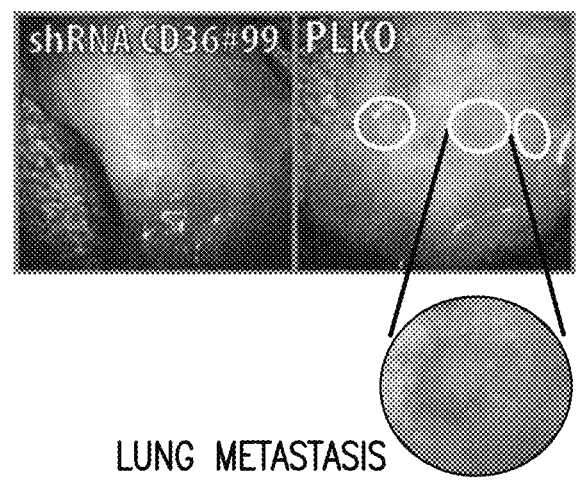
Figure 5D:
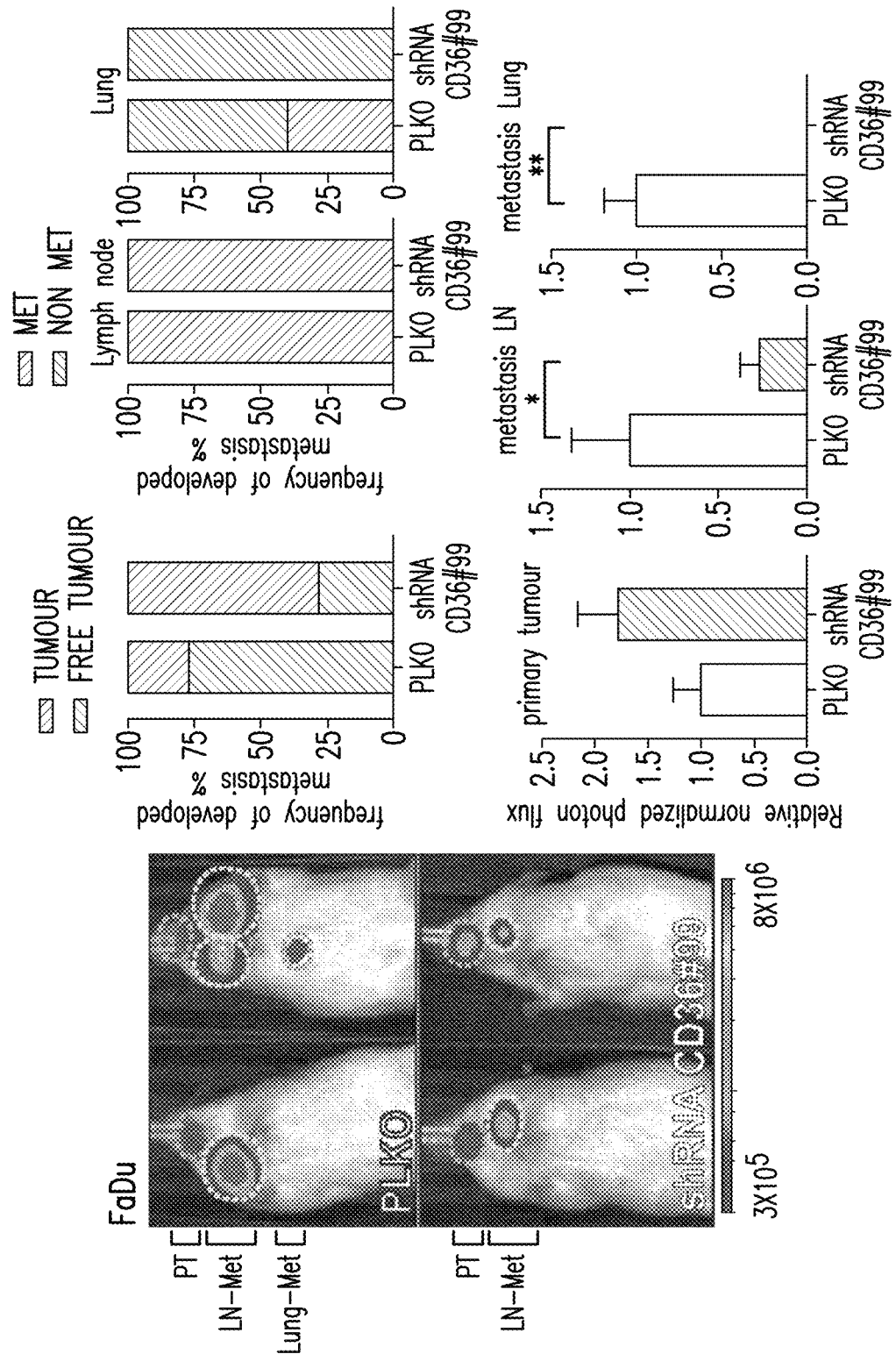
Figure 5E:
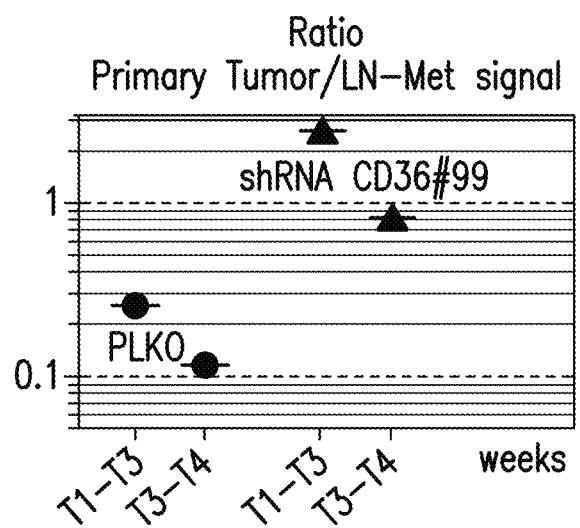
Figure 6A:
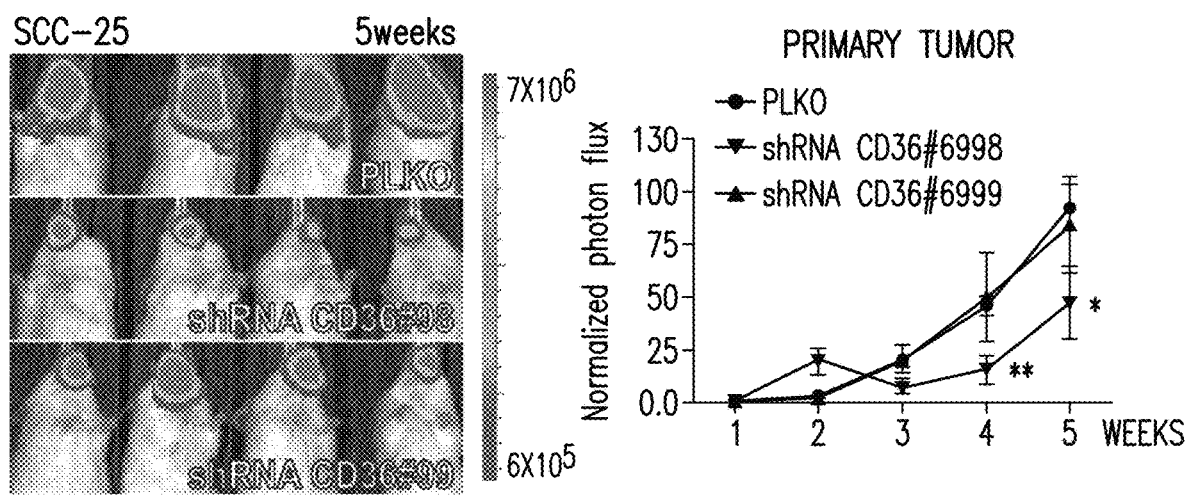
FIGS. 6A-6F.
Figure 6B:
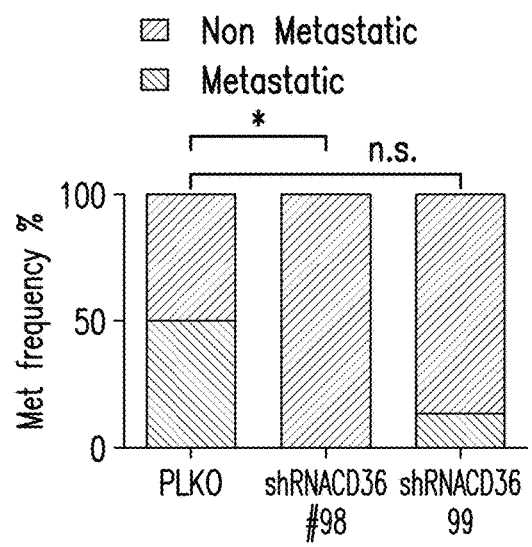
Figure 6C:
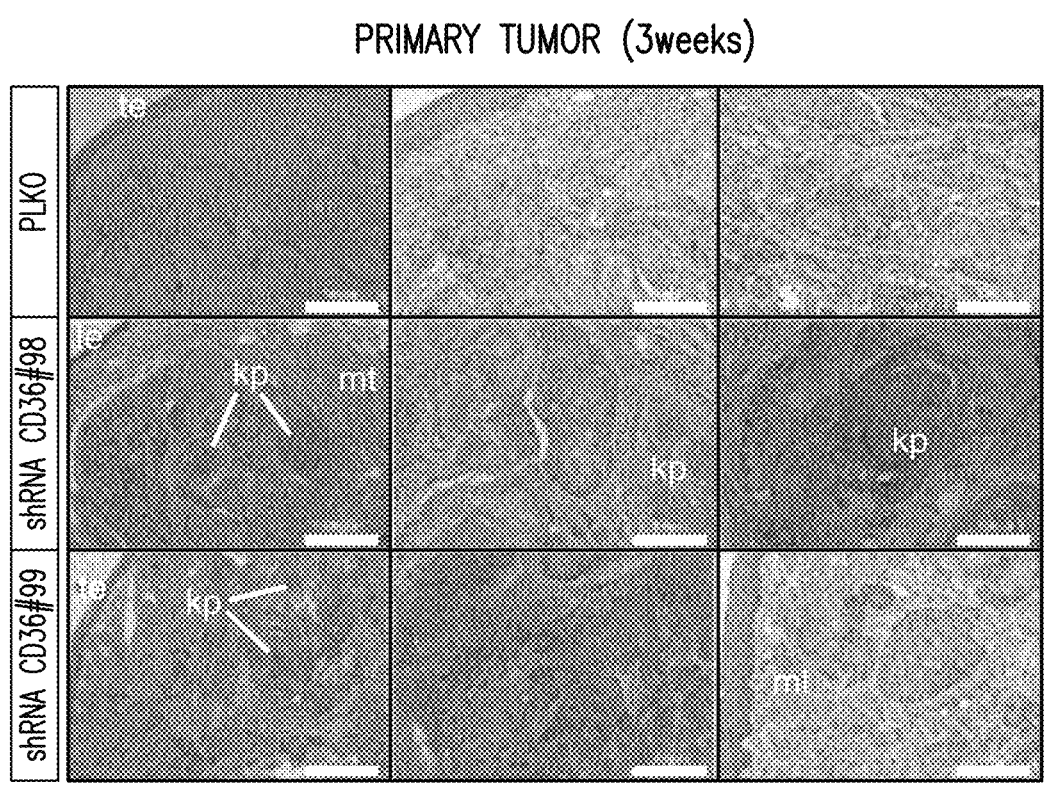
Figure 6D:
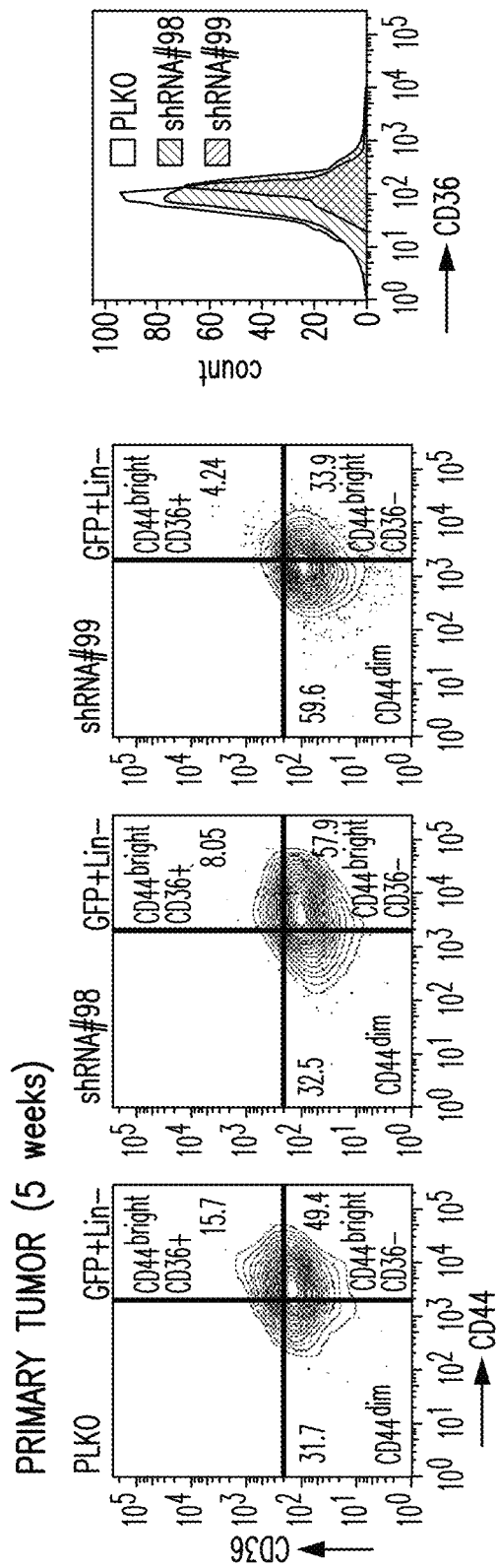
Figure 6E:
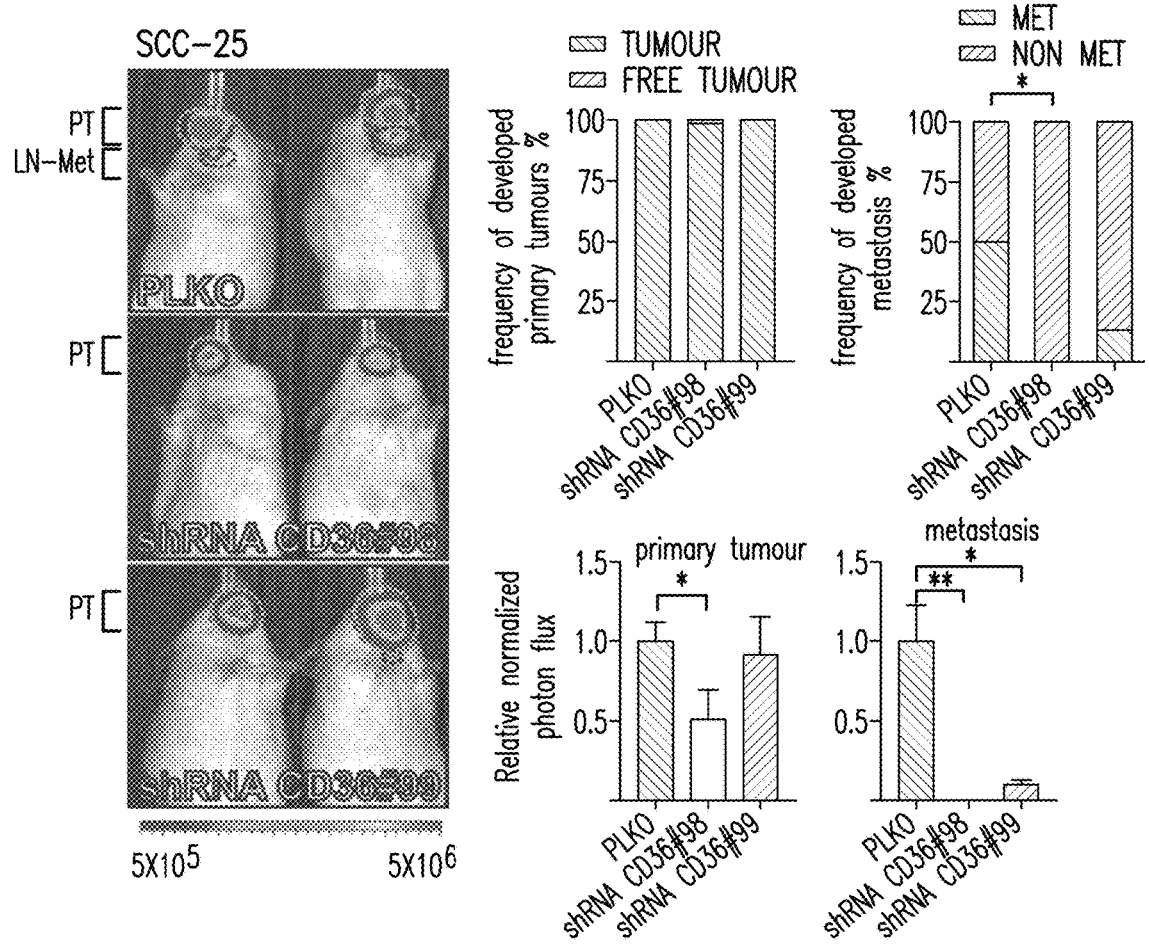
Figure 7A:
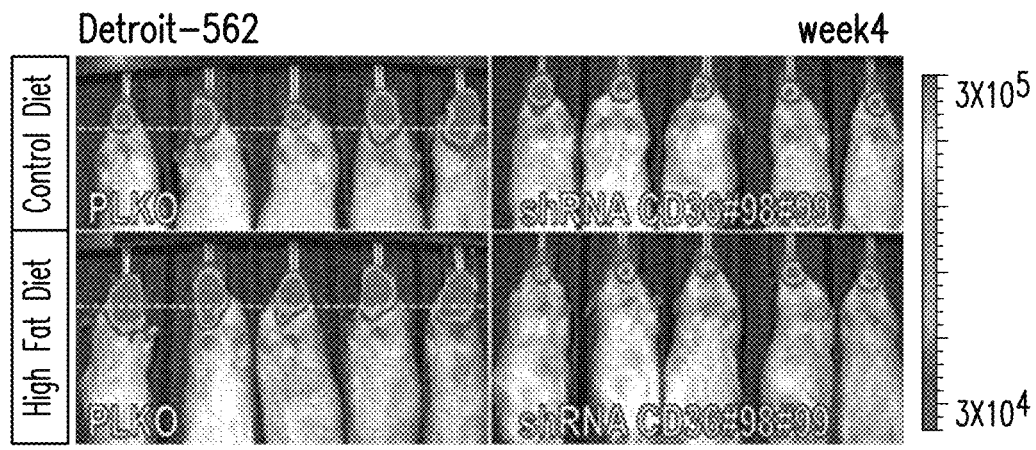
FIGS. 7A-7D.
Figure 7B:
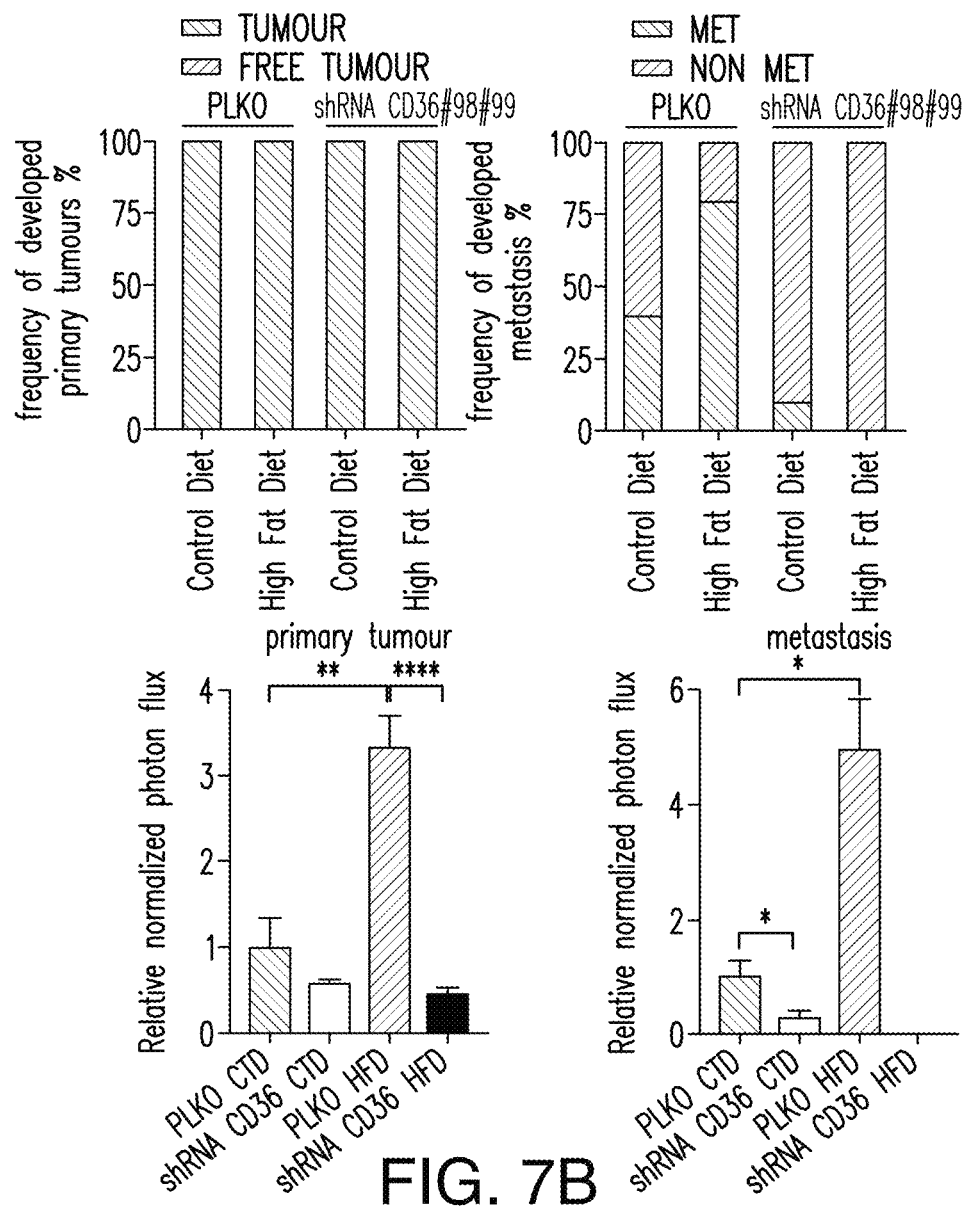
Figure 7C:
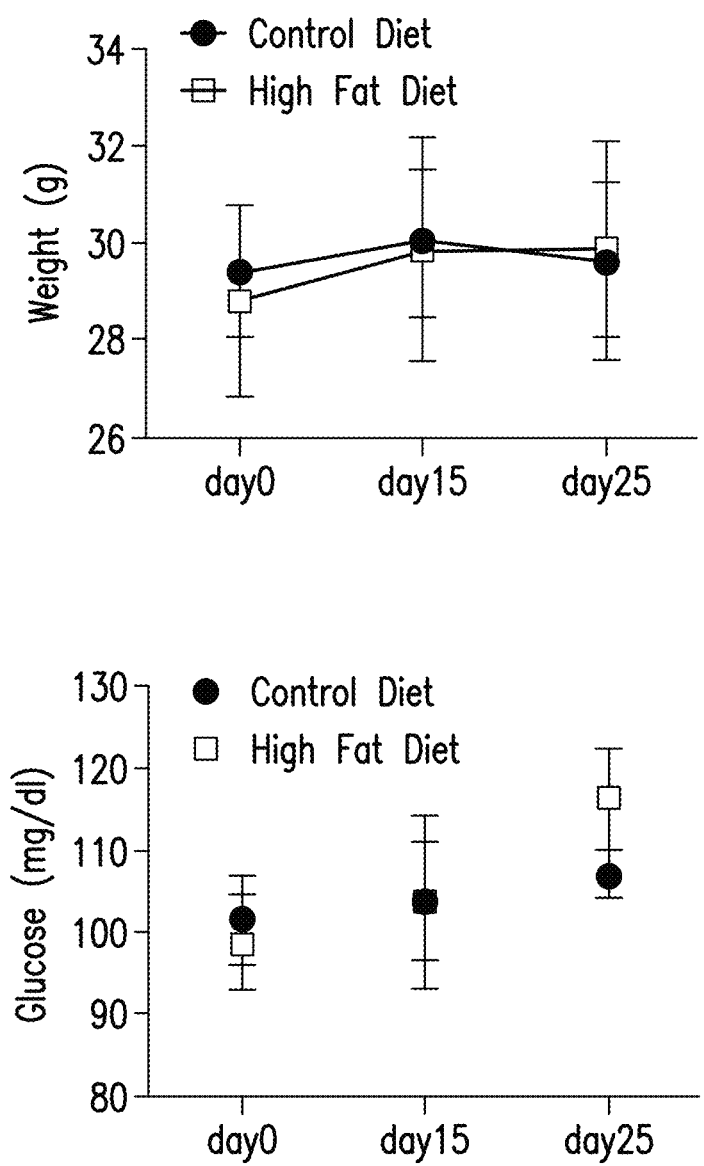
Figure 7D:
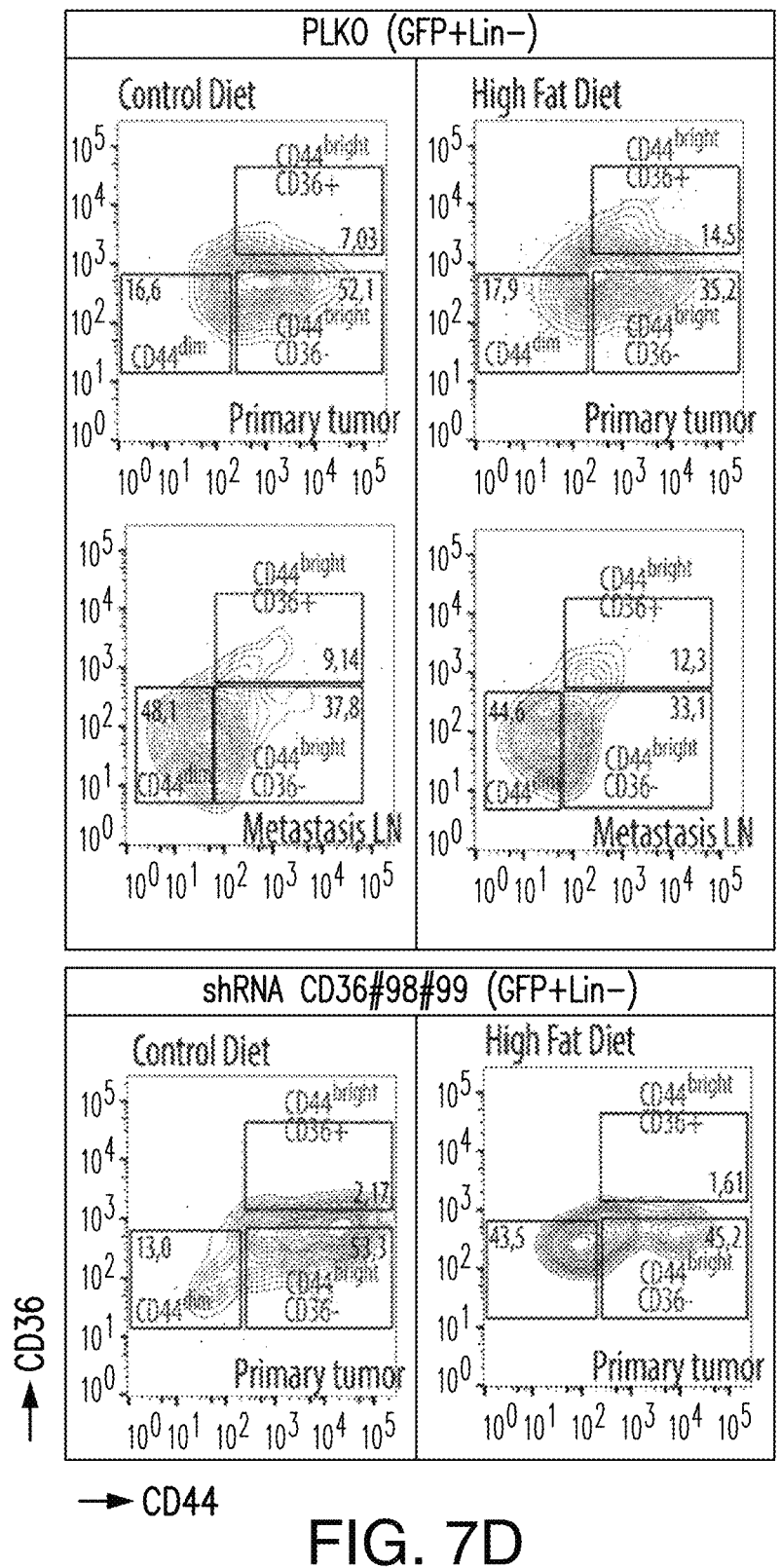
Figure 8A:
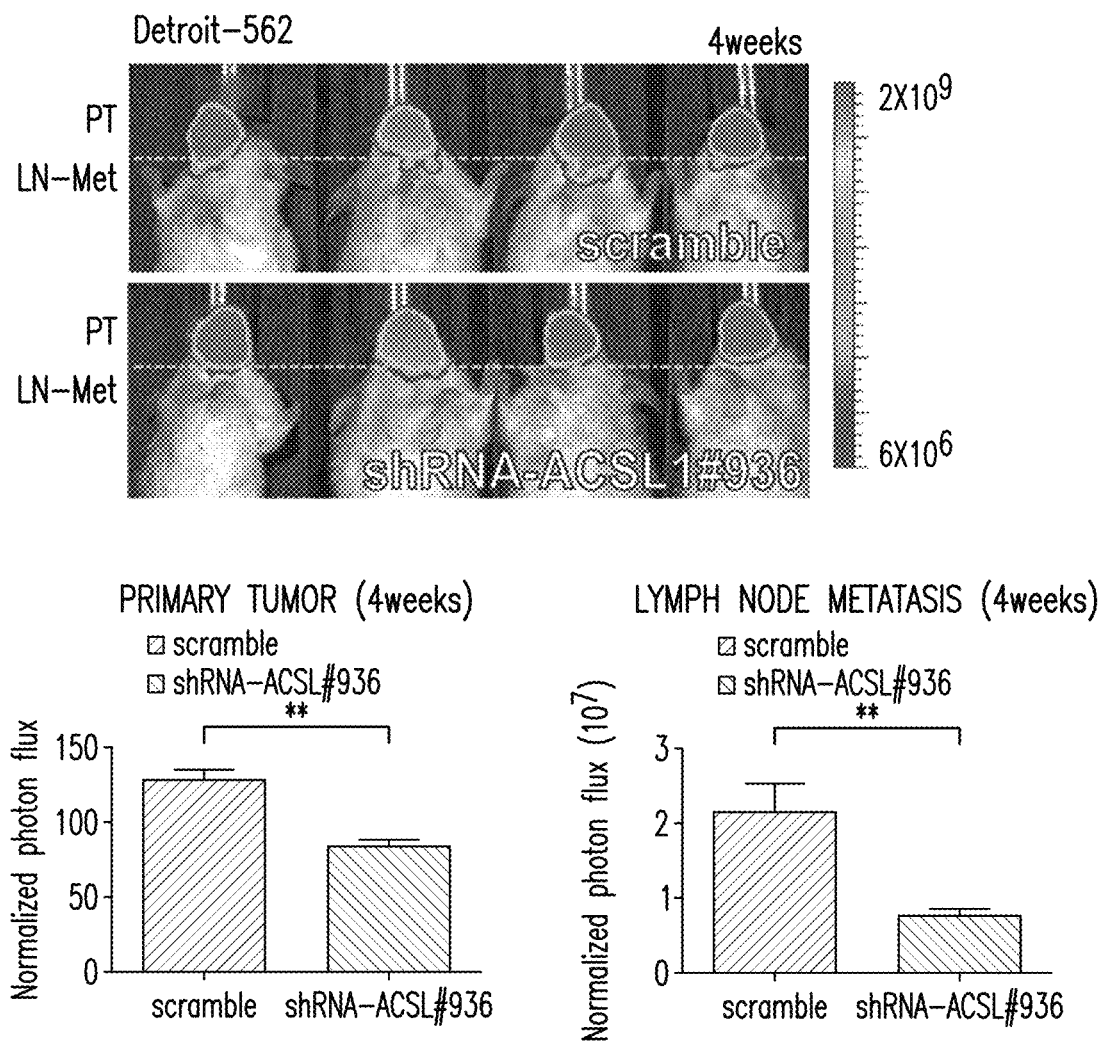
FIGS. 8A-8C.
Figure 8B:
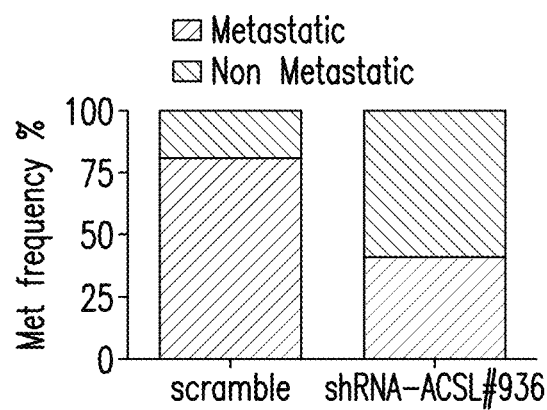
Figure 8C:
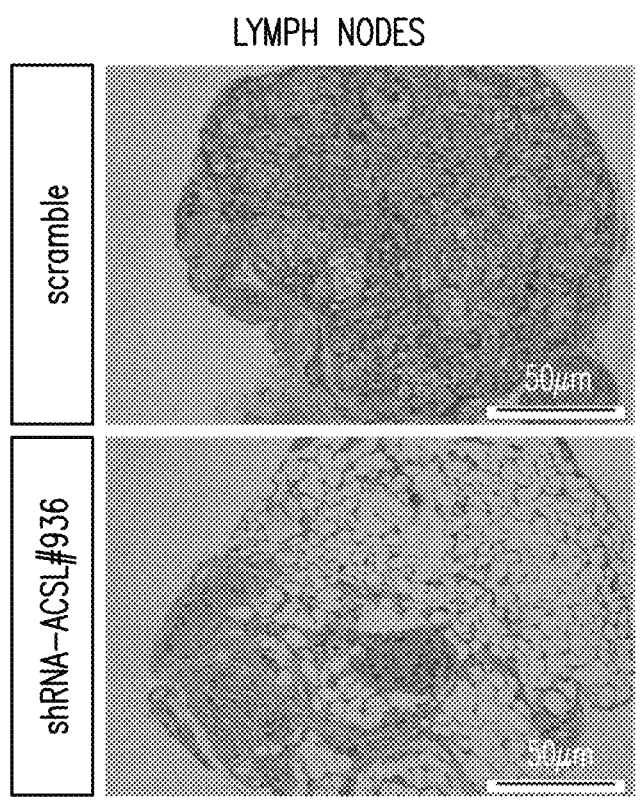

Primary tumour growth was also enhanced upon CD36 overexpression but to a much lesser extent than that observed over metastatic growth (<2 fold) (FIGS. 3C, 3D, 3G, 3H, 3I, 3L, 3M, 3N). In contrast, shRNA-mediated CD36 depletion (FIGS. 5A, 5B, 5D, 5E) slightly affected primary tumour growth in highly metastatic OSCC cell lines, but strongly reduced the metastases size in LNs (FIGS. 5D, 5E, 5F, 5G, 6A, 6B, 6E, 7A, 7B). Most importantly, shRNA-mediated CD36 depletion significantly reduced the penetrance of metastasis to the LNs in some cell lines by 80-100% without affecting the ability of tumour cells to initiate primary lesion (FIGS. 6A, 6E, 7A, 7B). Furthermore, CD36 depletion strongly inhibited the ability of FaDu cells to colonize the lungs (FIGS. 5C, 5D). The size of the LN metastases was also severely reduced upon depletion of D36 in all tumour lines, whereas primary tumour growth was only slightly affected in one cell line, but not in all other tested cell lines of patient-derived OSCC cells (FIGS. 5D, 6E, 7B). Interestingly, depletion of endogenous CD36 elevated the percentage of $CD44^{dim}$ cells in vivo in all tumours studied, suggesting that CD36 expression is required to maintain an undifferentiated state (FIGS. 5B, 6D, 7D).

Figure 5F:
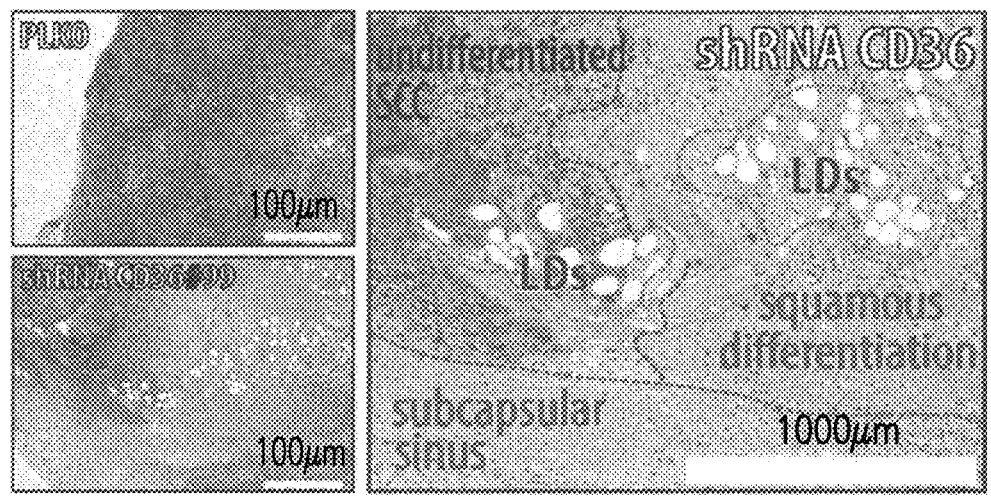
Figure 5G:
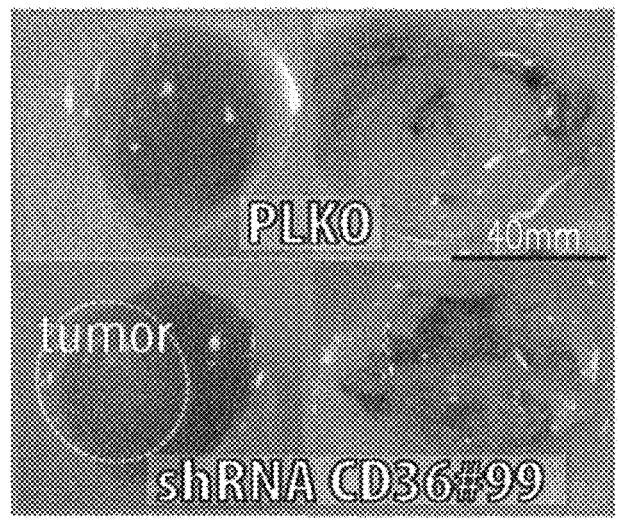
Figure 5H:
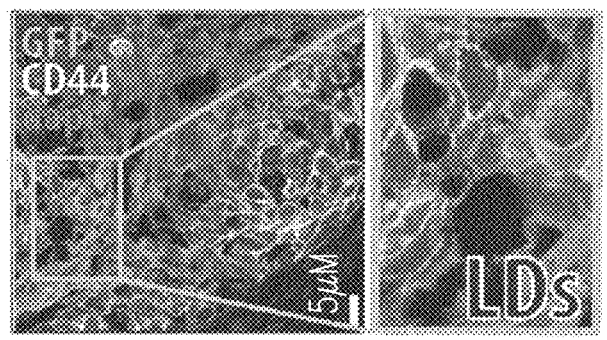
Figure 5I:
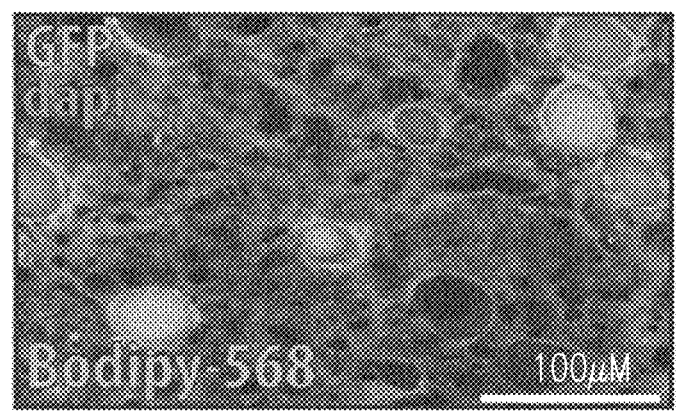
Figure 6F:
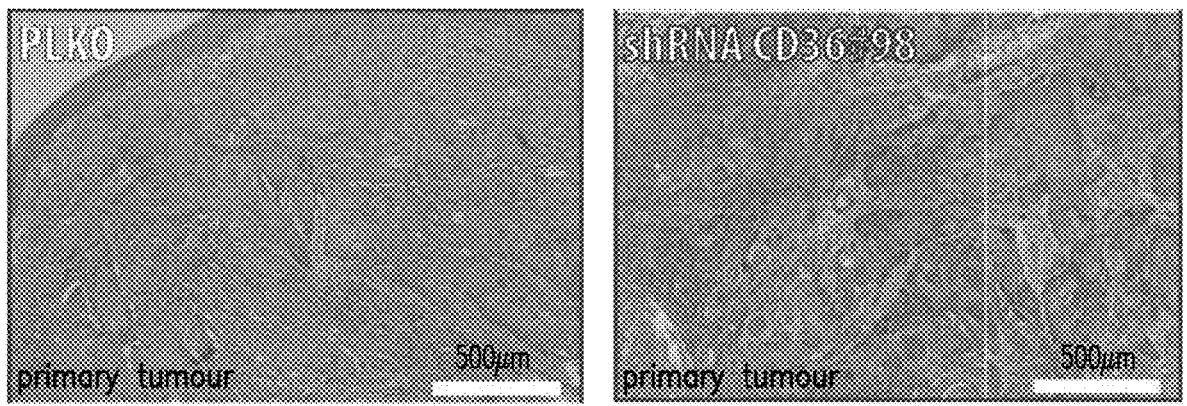

The histological analysis of the few LN metastases that grew from CD36-depleted cells presented an intriguing pattern of large swollen cells (FIG. 5F). These structures were specific to metastases, since they were not present in oral tumours generated by OSCC cell depleted of CD36 (FIG. 6F). CD36 not only internalizes fatty acids but also is necessary to trigger fatty acid beta-oxidation in some cell types, and indeed these structures comprised large lipid droplets with non-metabolized lipids, as shown by staining with the fluorescent lipid sensor BODIPY (FIG. 5I). Based on this, and also in the gene expression signature defining the tumour LRs which contained many genes involved in lipid metabolism, including lipogenesis, the inventors hypothesized that CD36+ cells might rely on fatty acid metabolism/oxidation to obtain the necessary energy for colonizing LNs and exert their metastatic potential. Measuring intermediate metabolites of lipid oxidation requires a very rapid purification of a large number of cells that was unfeasible with the low yield of FACS-isolated CD36+ cells acquired from tumours in our in vivo method. Several alternative approaches were taken to test said hypothesis.

First, it was confirmed by global transcriptome analysis that $CD36+/CD44^{bright}$ cells, but not their $CD36-/CD44^{bright}$ counterparts, isolated from primary oral orthotopic tumours expressed many genes involved in lymphatic metastasis and lipid metabolism, overlapping with the dye+ (DID+) signature that had been previously obtained.

Figure 9A:
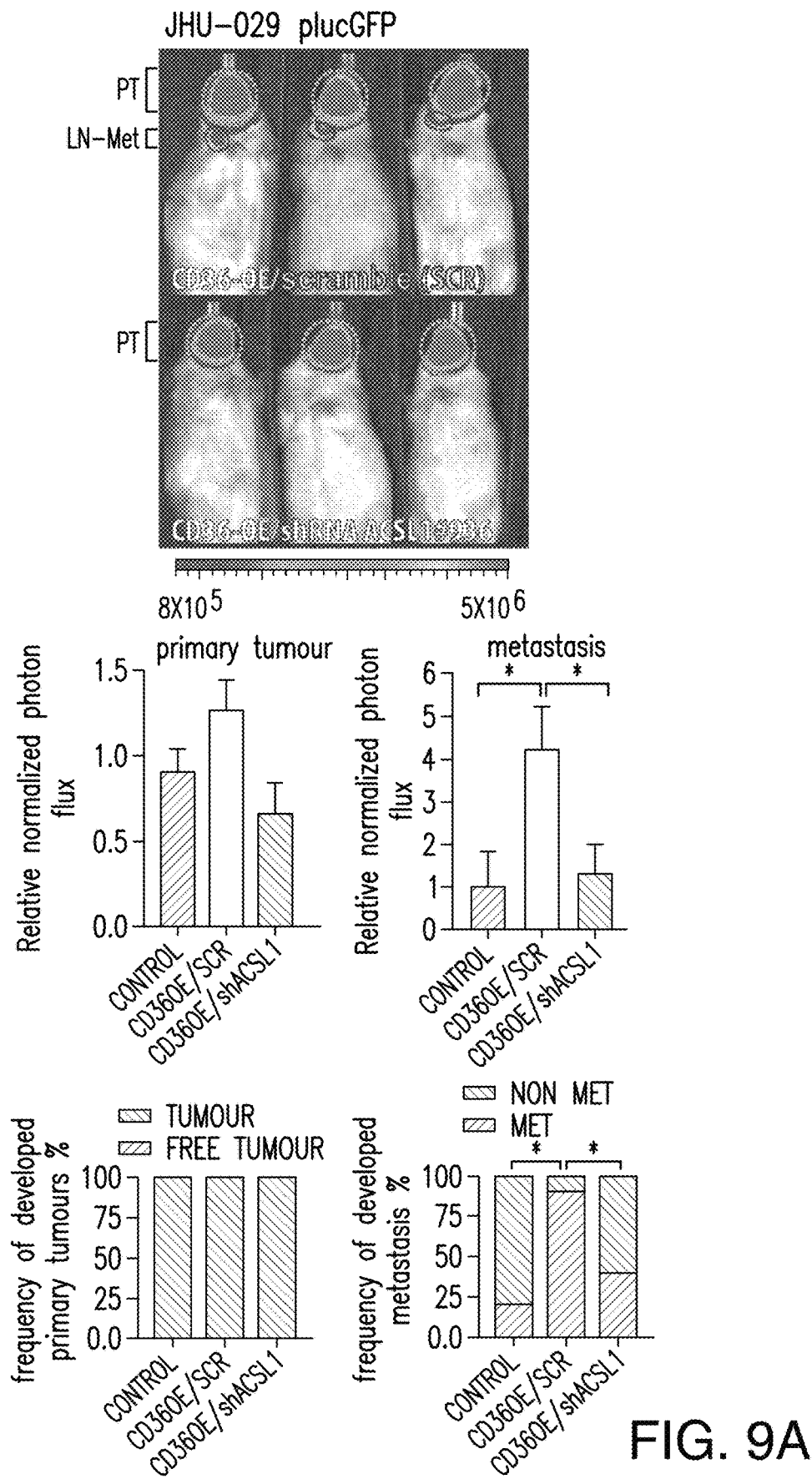
FIGS. 9A-9C.
Figure 9B:
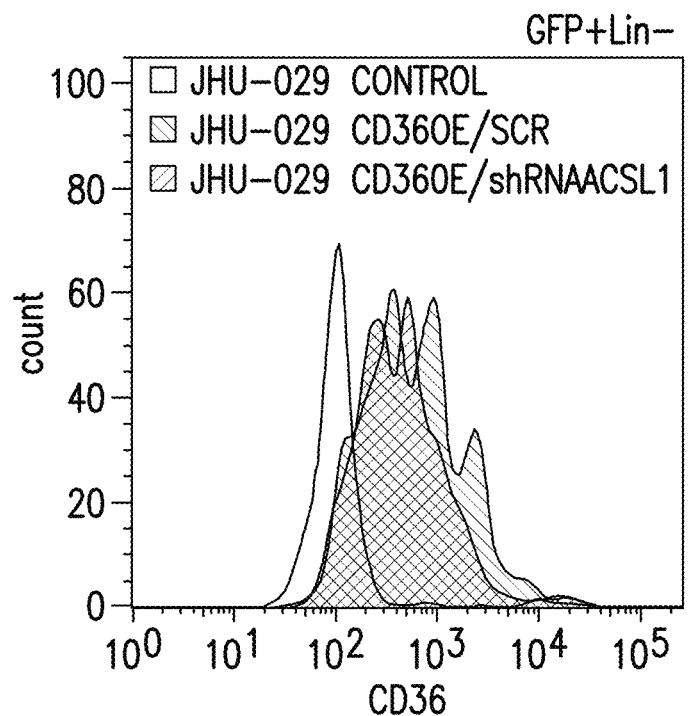
Figure 9C:
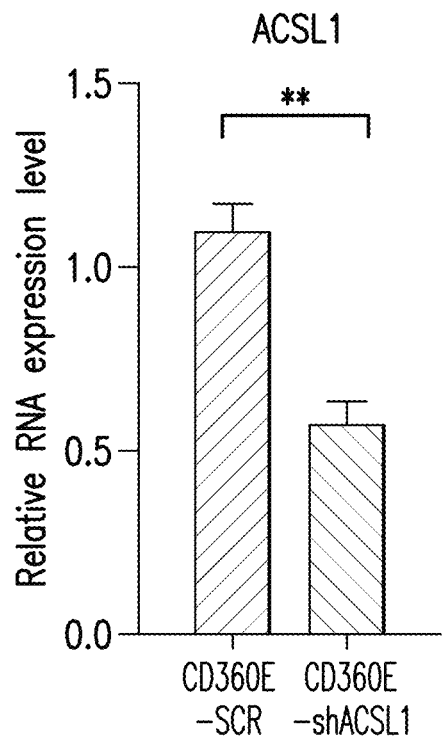

Second, depletion of ACSL1 (acyl-CoA synthetase long-chain family member1), which adds an acyl-CoA moiety to fatty acids to activate their breakdown at the mitochondria (Pepino et al., 2014; Ellis et al., 2010), significantly reduced the LN metastatic potential of OSCC cells, almost to the same extent as depletion of CD36 (FIGS. 9A-9C). Interestingly, and similar to the results obtained upon depletion of endogenous CD36, knockdown of ACSL1 did not affect primary tumour uptake and only slightly reduced the size of the oral lesions, but strongly reduced the penetrance of LN metastases and their size (FIGS. 9A-9C). Importantly, depletion of ACSL1 specifically reduced the increase in the penetrance of metastasis induced by overexpressing CD36 in poorly metastatic OSCC tumour cells, indicating that it acted downstream of CD36 (FIGS. 9A, 9B, 9C).

Additionally, it was found that $CD36+/CD44^{bright}$ cell expressed higher protein levels of three key enzymes involved in fatty acid beta oxidation, ACADVL, ACADM and HADHA, compared to their $CD36-/CD44^{bright}$ counterparts, as determined by FACS analysis.

Figure 12A:
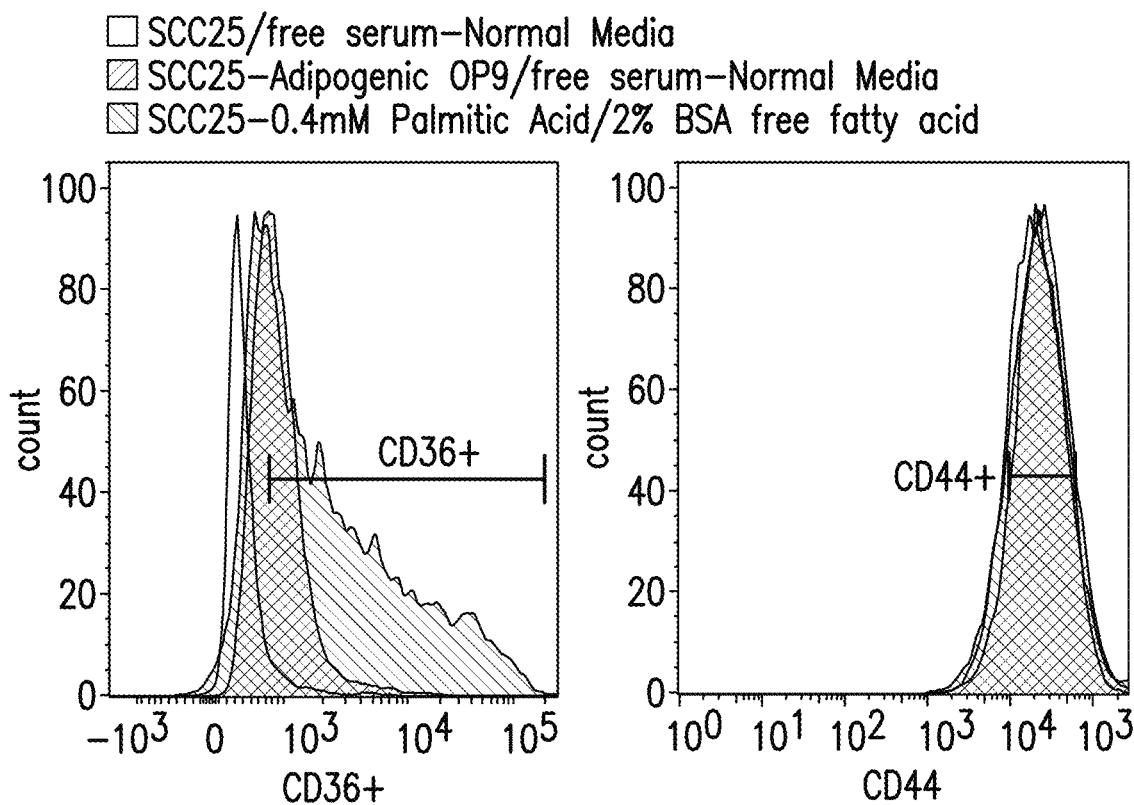
FIGS. 12A-12F.
Figure 12B:
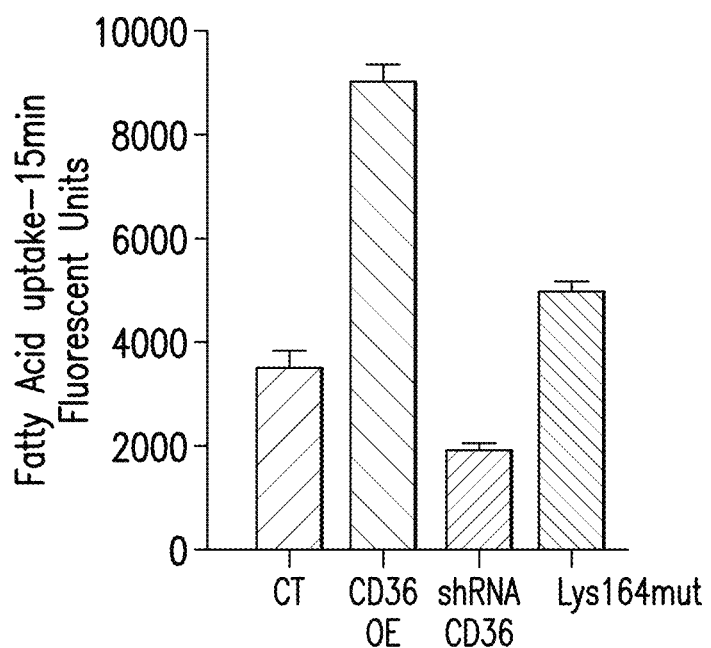
Figure 12C:
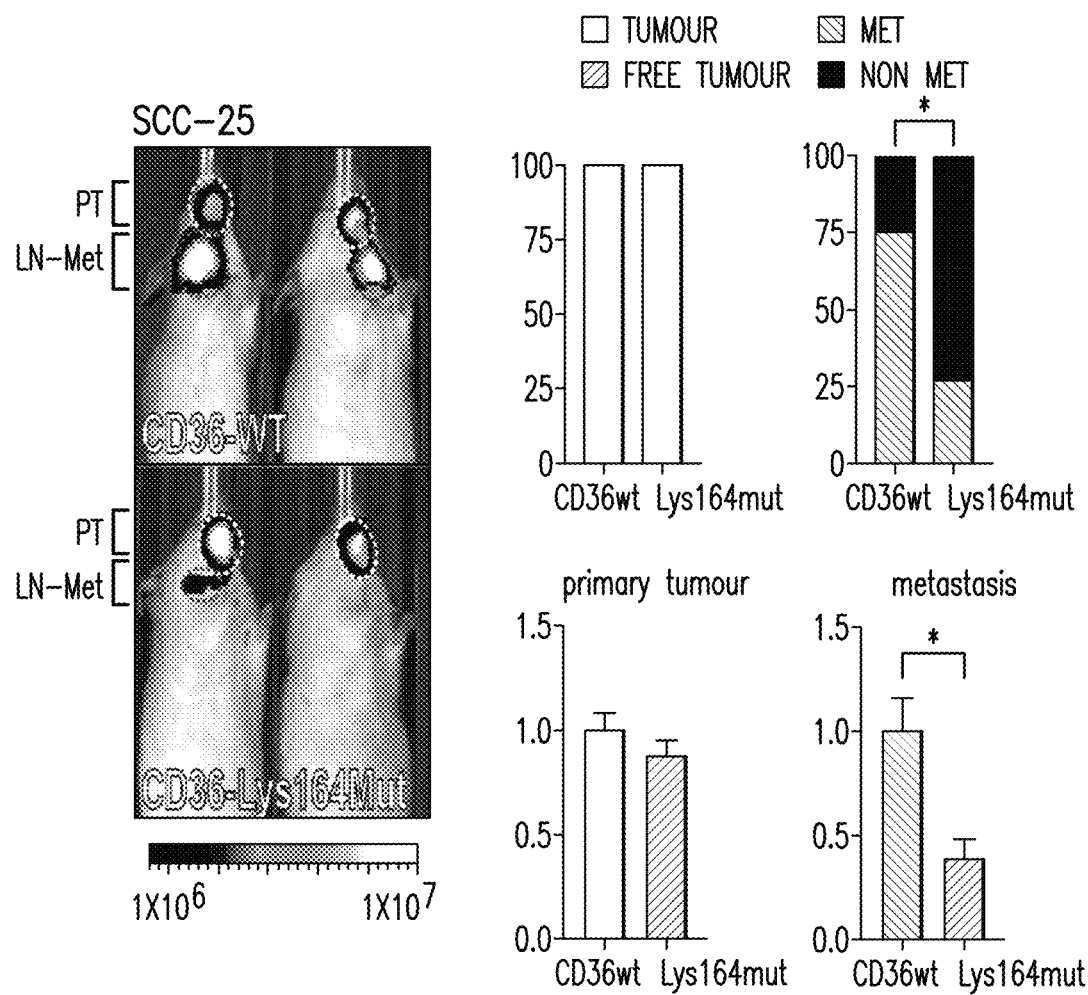

It was also tested whether increasing the levels of lipids in circulation would enhance the LN metastatic potential of OSCC cells in a CD36-dependent manner. Interestingly, NSG mice fed with a high fat diet developed only slightly larger oral tumours but an increased number and larger LN metastases, in a manner dependent on the expression of endogenous CD36 (FIGS. 7A, 7B). These mice did not significantly gain any weight or increase their blood glucose levels during the experiment (FIG. 7C). In fact, the boost in the metastatic potential of OSCC in high-fat-diet mice correlated with a significant increase in the percentage of CD36+ cells in the oral and metastatic lesions (FIG. 7D). Interestingly, the percentage of CD36+ cells was also strongly elevated when OSCC cells were co-cultured with mature OP9-derived adipocytes, but not with non-adipogenic OP9 parental cells or with SCC tumour associated fibroblasts, suggesting that the expression of endogenous CD36 in OSCC was responsive to lipids (FIGS. 12A, 12B). To directly test this, the present inventors exposed OSCC cells in culture for 2 days with palmitic acid (PA), a fatty acid recognized by CD36. Stimulation of OCCs with PA robustly induced the percentage of CD36+ cells in culture (FIG. 12A). Importantly, PA significantly boosted the size and the frequency of the LN metastasis in a manner completely dependent on CD36, without any effect over primary tumour growth. PA even promoted lung metastasis in 10% of inoculated mice, something that the inventors have never observed in more than 100 mice inoculated with control SCC25 tumour cells (FIG. 12E).

Figure 12D:
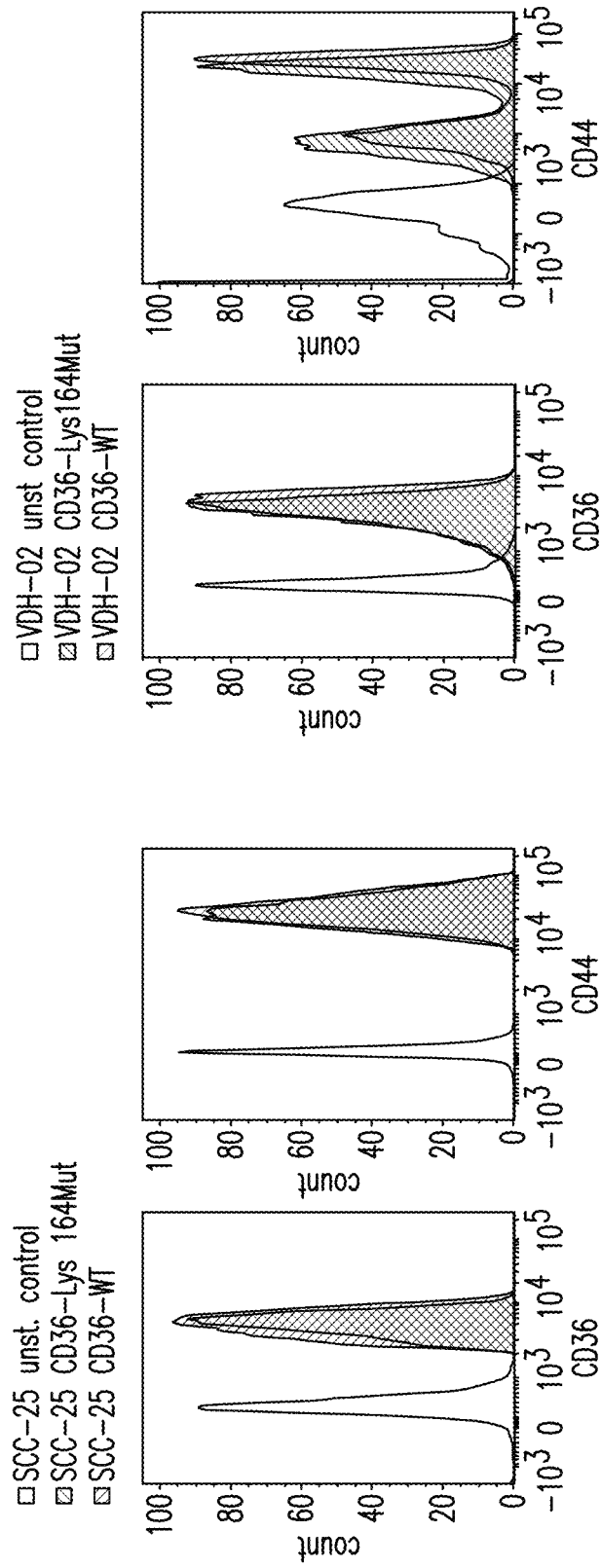
Figure 12E:
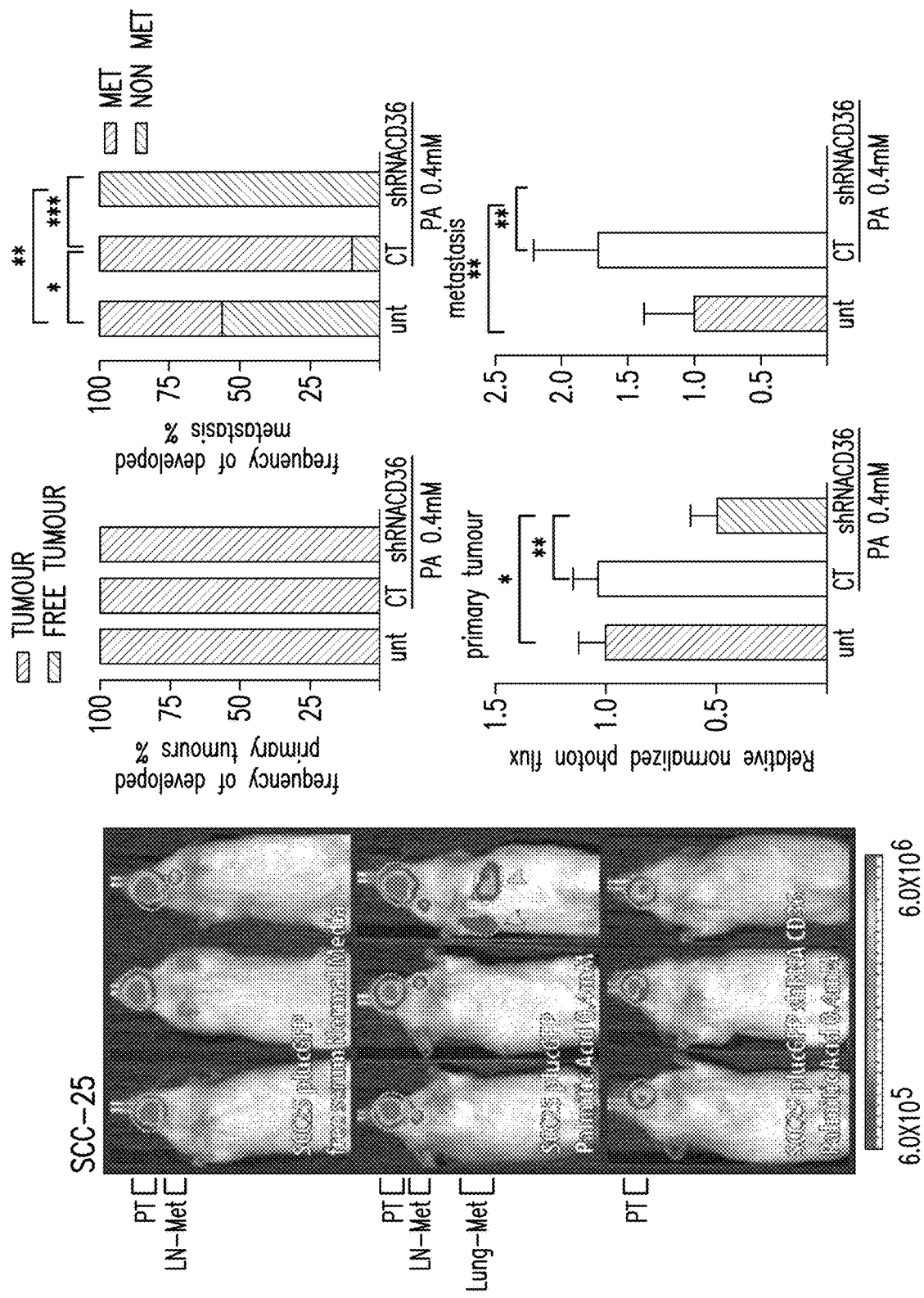
Figure 12F:
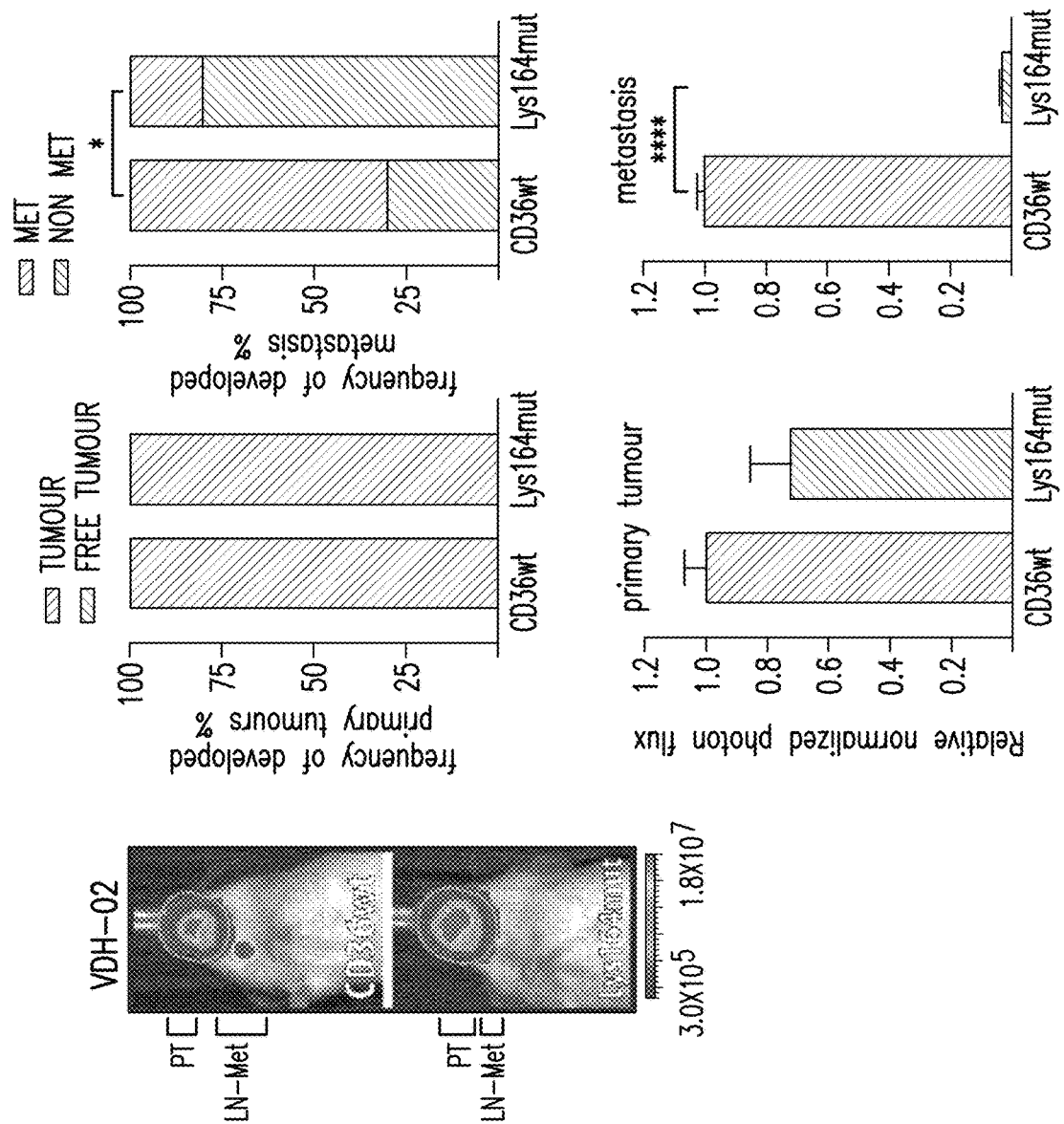
Figure 13A:
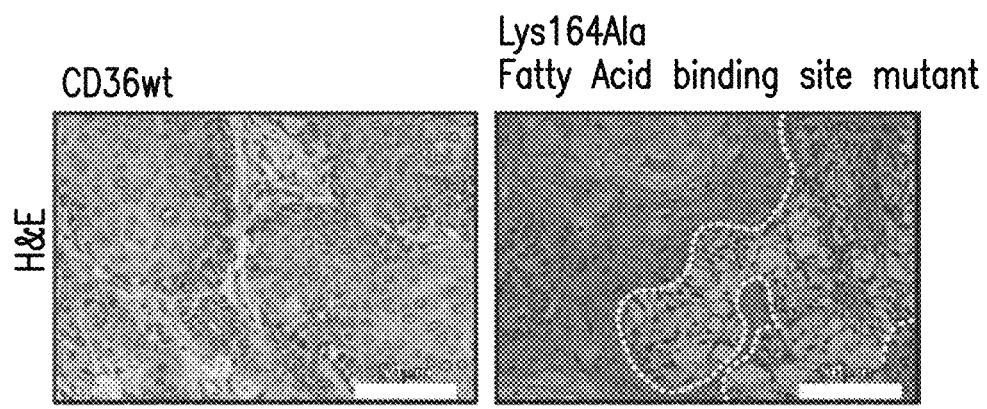
FIGS. 13A-13C.
Figure 13B:
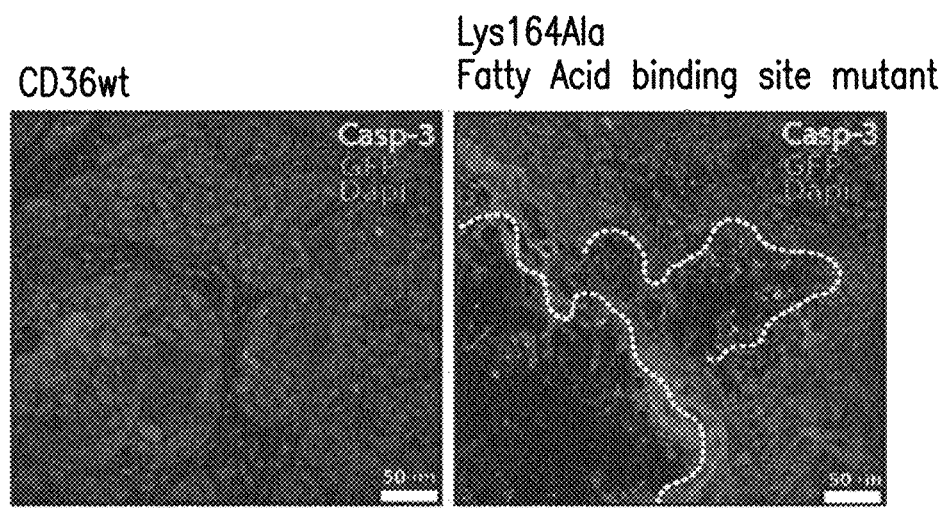
Figure 13C:
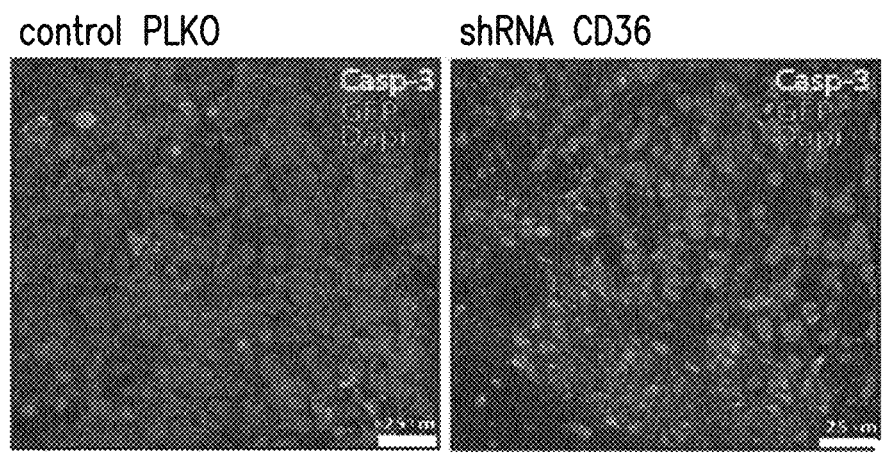
Figure 14:
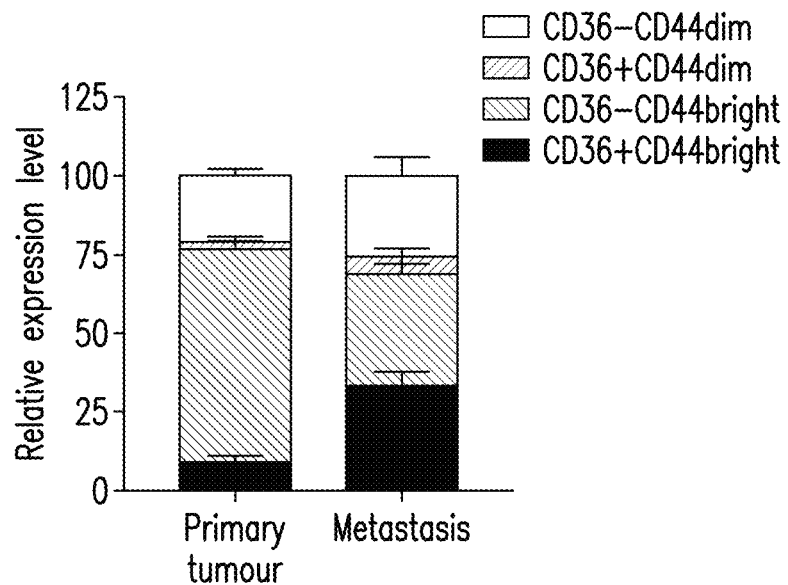

Importantly, OSCC cells expressing the mutant CD36 generated primary lesions with the same penetrance as OSCC cells harbouring wild type CD36, but displayed significantly fewer and much smaller metastases (FIG. 12C, FIG. 12F), Equal expression of WT and mutant CD36 was verified by FACS sorting (FIG. 12D). Interestingly, the LN metastases generated by OSCC tumour cells expressing the CD36-Lys164Ala mutant contained large lipid droplets similar to those formed upon depletion of endogenous CD36 (FIG. 13A). Since CD36 is also known to trigger fatty acid beta-oxidation in some instances, this observation led the inventors to hypothesize that inhibition of CD36 might lead to an accumulation of endogenously synthesized unmetabolized lipids. This continuous accumulation of lipids would ultimately result in metastatic lipotoxicity and cell death. Indeed, substantial Caspase-3 immunoreactivity was observed surrounding these lipid droplet-rich areas, both in metastases expressing the CD36-Lys164Ala mutant, or those depleted of endogenous CD36 (FIGS. 13B, 13C).

Example 3.—Metastasic Potential of CD36+ Cells

These results supported a role for CD36 positive cells in promoting OSCC metastasis by sensing, internalising and metabolising lipids from their surroundings in a CD36-dependent manner. Since such conclusions relied so far on modulating CD36 expression or activity, the present inventors next asked whether CD36+ cells constituted the population with the highest metastatic potential within the primary oral lesions.

Figure 10A:
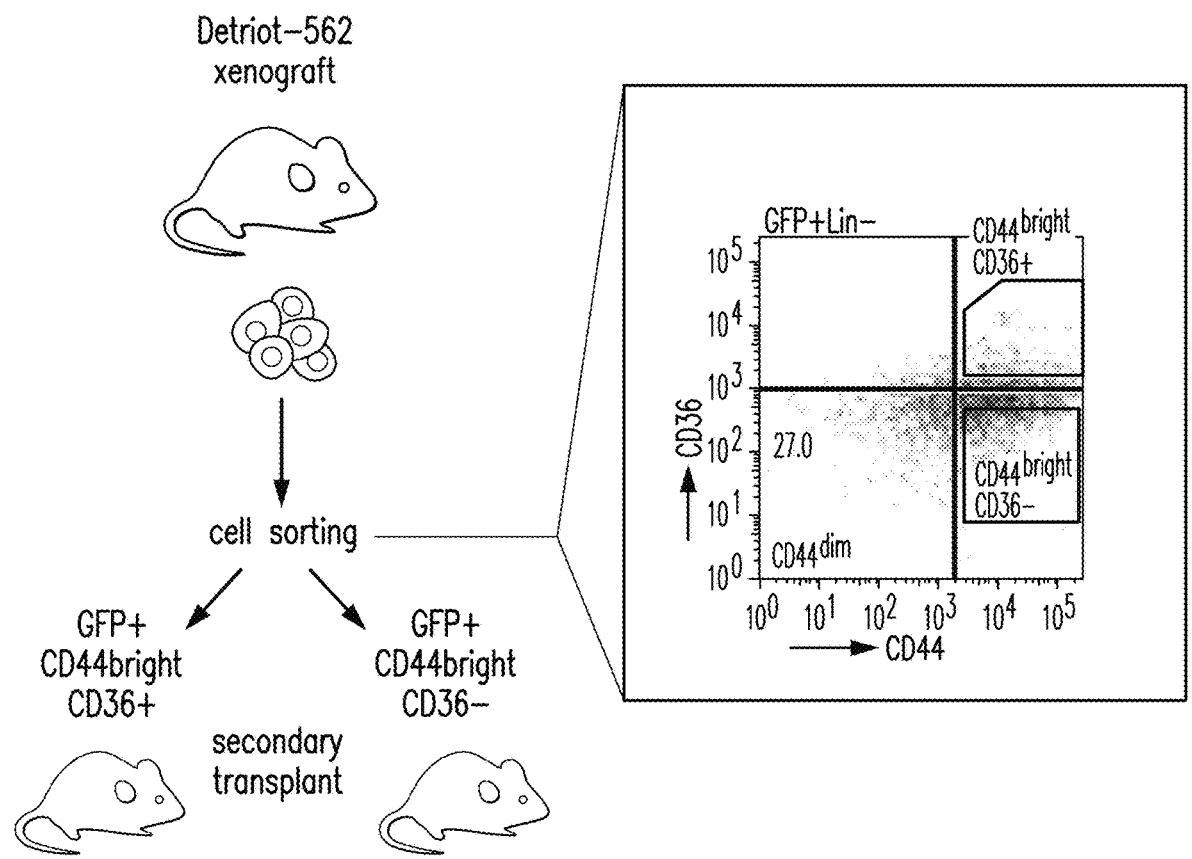
FIGS. 10A-10D. CD36 positive cells are responsible for initiating and promoting OSCC metastasis.
Figure 10B:
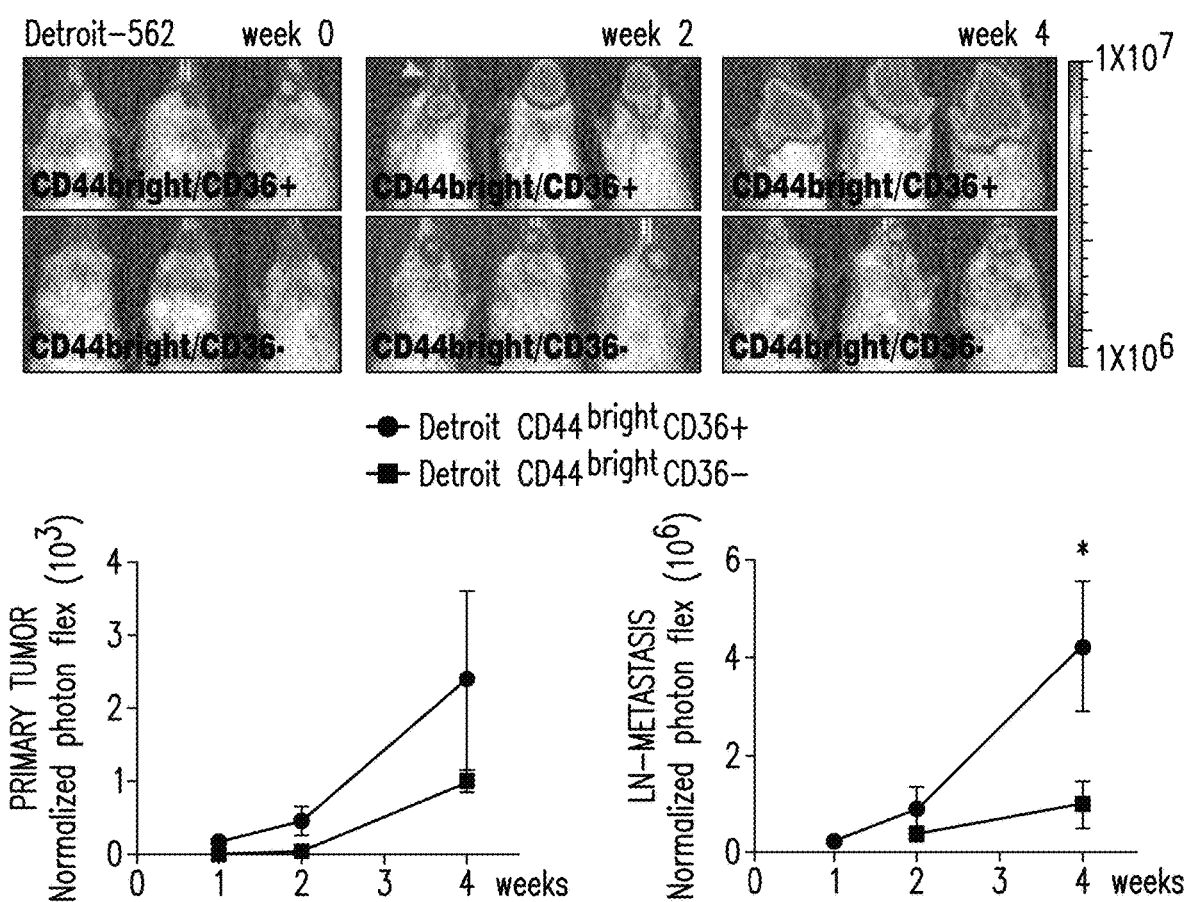
Figure 10C:
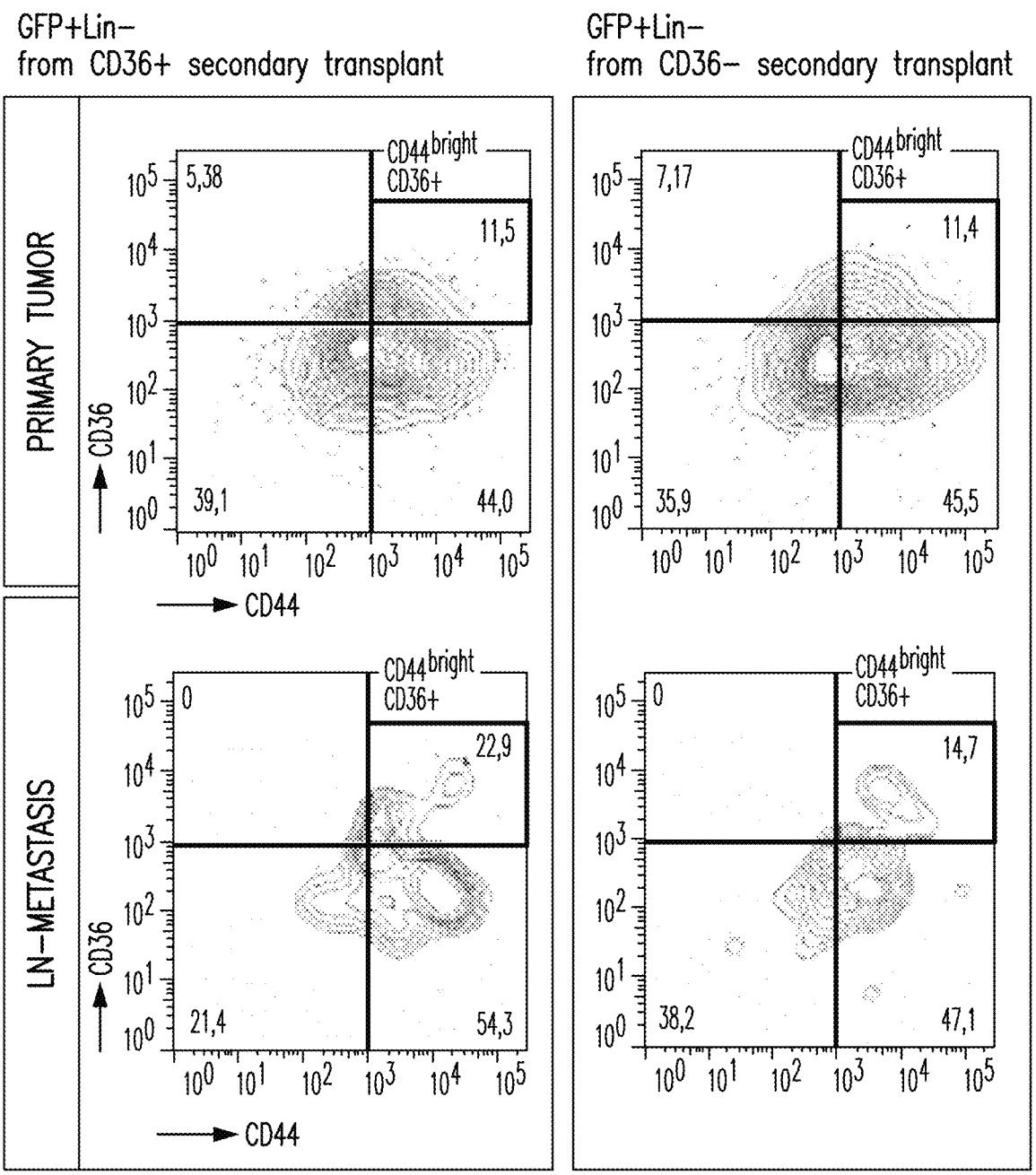
Figure 10D:
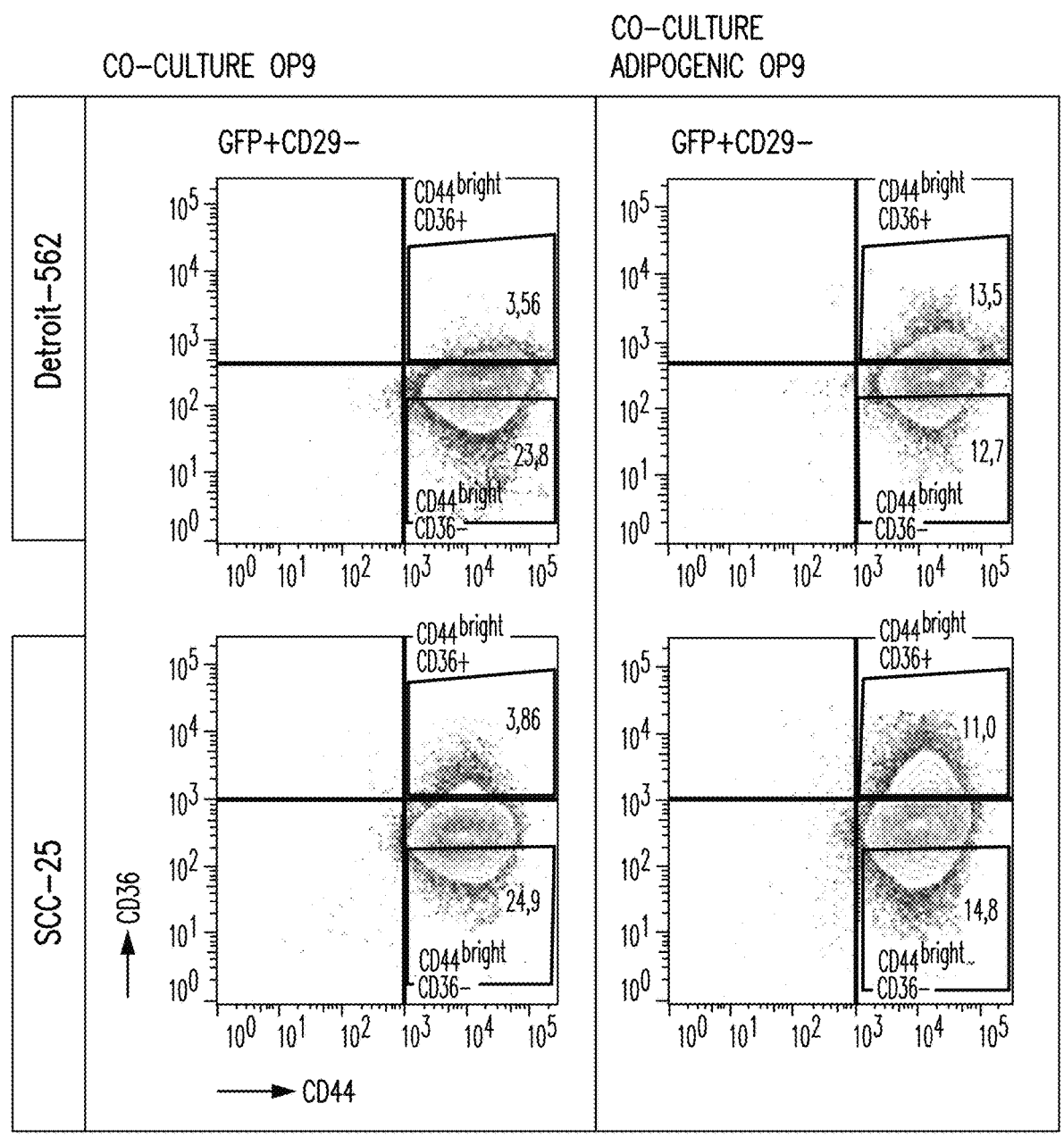
Figure 11:
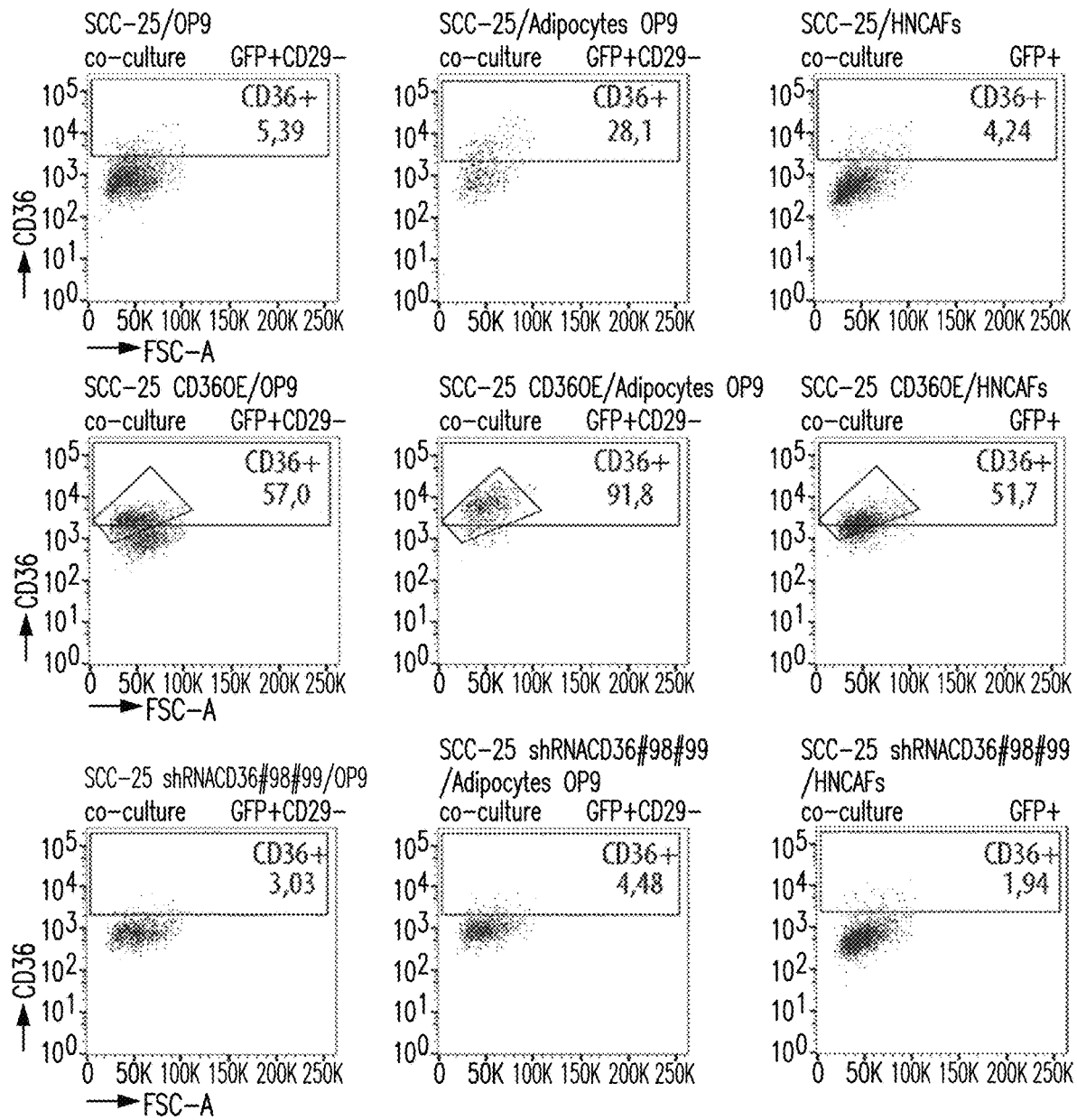
FIG. 11. Flow cytometry analysis of co-cultures SCC/OP-9, SCC-25/adipogenic OP-9 and SCC-25/HNCAFs (Head and neck cancer associated fibroblasts). SCC-25 parental, SCC-25 CD36-OE (overexpression) and shRNACD36 (#98 #99) were co-cultured under the different conditions. Cells were analysed after 2 days of co-culture. Numbers indicate CD36+ cells in the represented gate expressed as percentage.
Figure 15:
FIG. 15. CD36 mRNA relative expression levels, measured by RT-qPCR, from SCC-25 CD36− sorted cells either co-cultured for 2 days with adipogenic OP9 (Ad.OP9) or not, or from SCC-25 CD36+ sorted cells co-cultured with Ad.OP9.
Figure 16A:
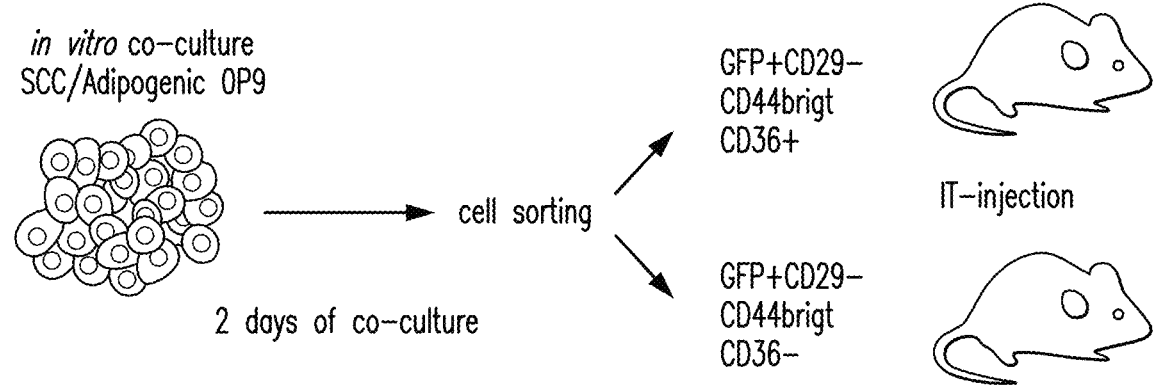
FIGS. 16A-16G.
Figure 16B:
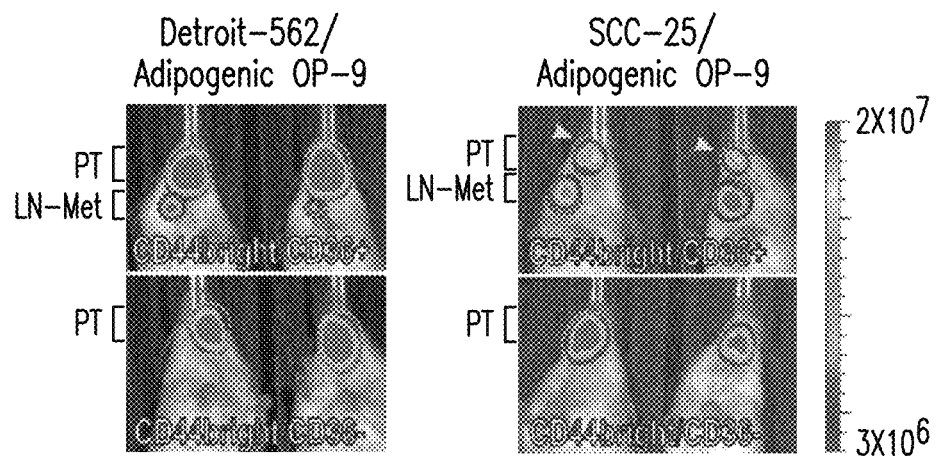
Figure 17A:
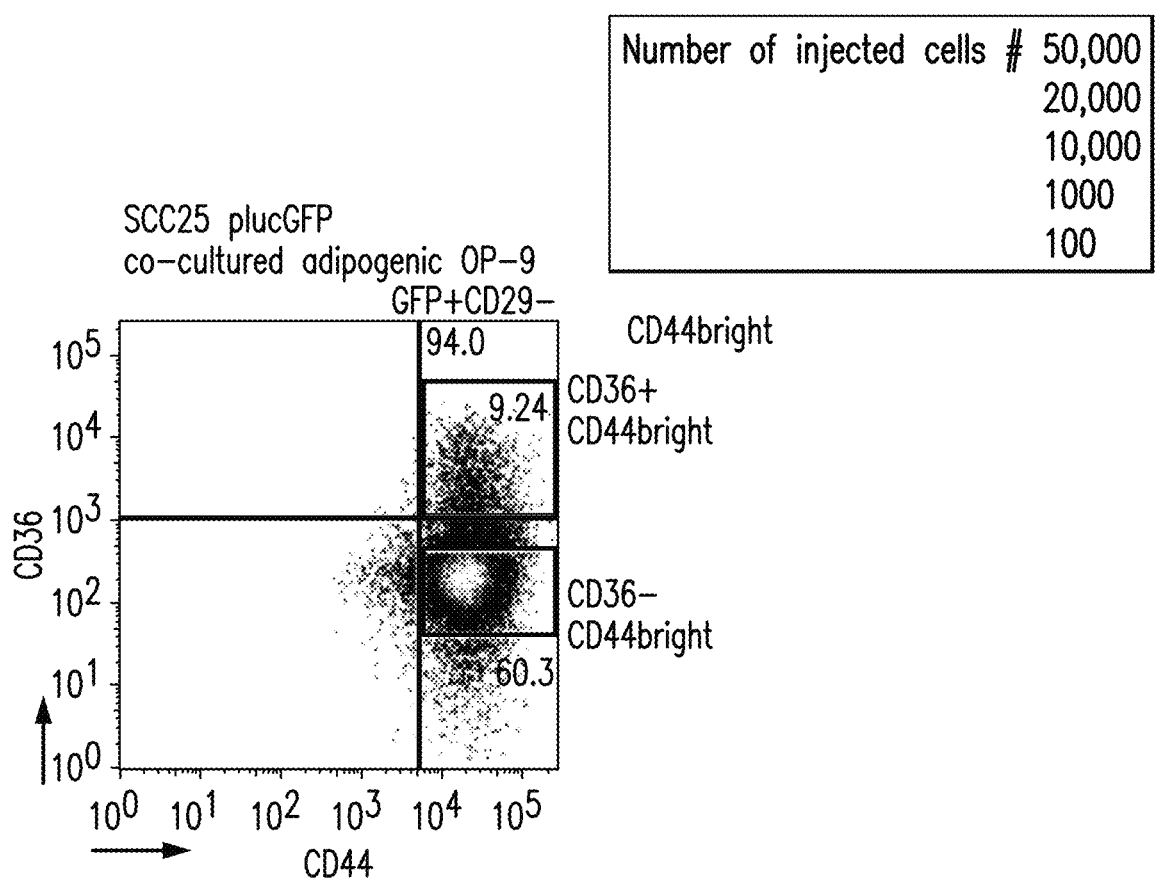
FIGS. 17A-17C.
Figure 17B:
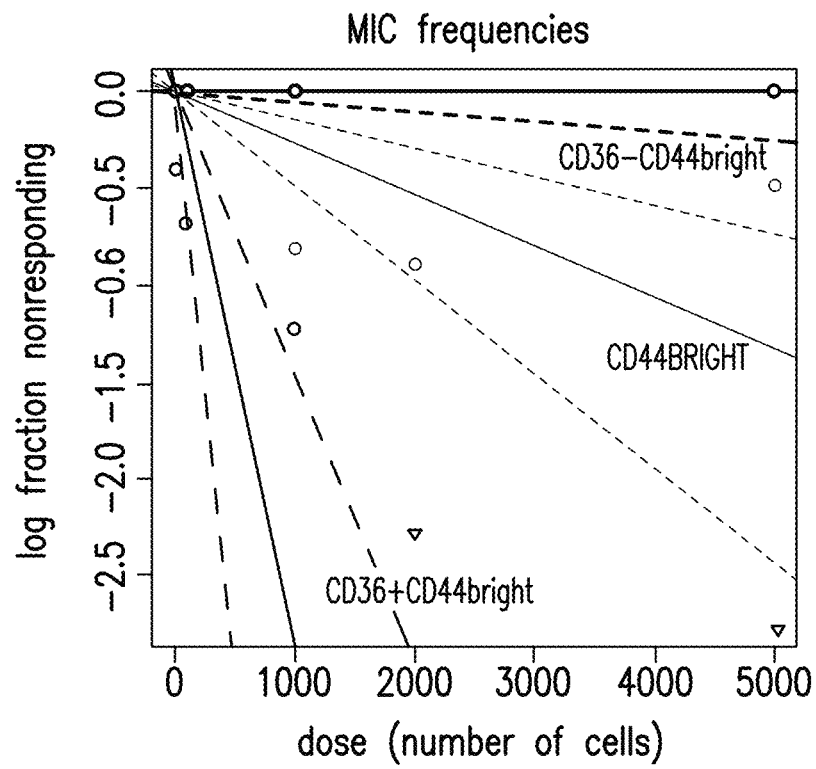
Figure 17C:
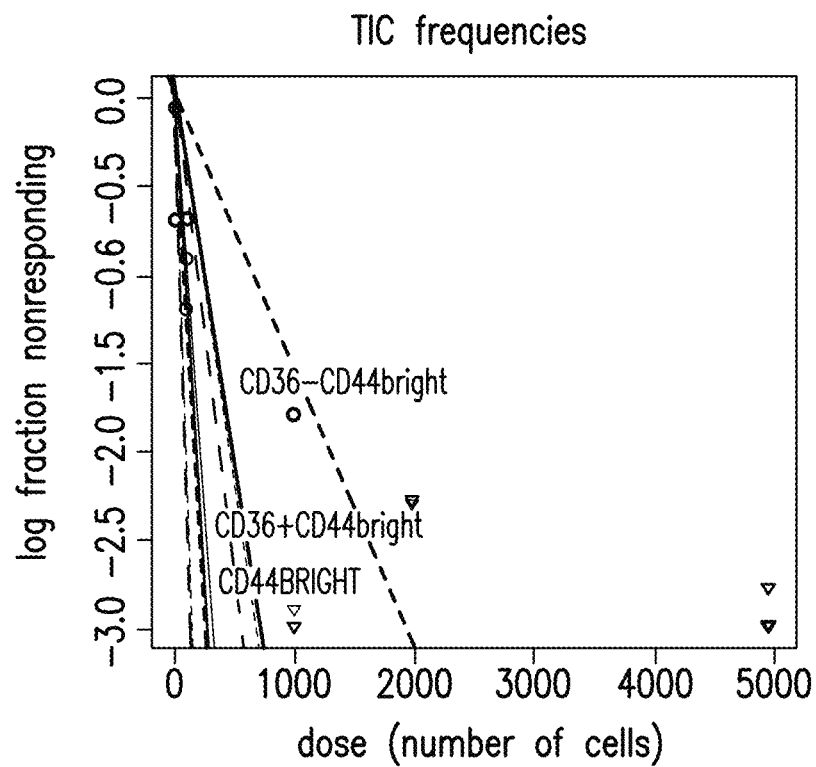

First, they observed that in all OSCC cell lines and PDC tested, $CD36+/CD44^{bright}$ cells were always enriched at the metastatic sites compared to the primary oral lesions (FIG. 15). It was also observed that, when CD36+ and CD36− cells isolated from primary orthotopic oral lesions were inoculated separately into the oral cavity of secondary recipients, CD36+ cells were quicker than their CD36− counterparts to generate LN metastases, that were also much larger (FIGS. 10A, 10B). Interestingly, although mice were inoculated with a pure population of CD36+ cells, both the oral lesions and the macroscopic metastases generated by these displayed a very similar proportion of CD36+/CD44$^{bright}$ CD36−/CD44$^{bright}$ and CD44$^{dim}$ cells as the original oral tumour, indicating that CD36+ cells can re-establish tumour cell heterogeneity in vivo (FIG. 10C). The inventors observed no significant differences in the capacity of either CD36+ or CD36− populations to generate primary oral lesions (FIG. 10B). Thus, both CD36+ and CD36− cells were capable of generating metastases albeit with very different kinetics. Intriguingly, the metastatic lesions that formed with a longer latency in mice inoculated with CD36− cells as compared to those inoculated with CD36+ cells contained a high percentage of CD36+ cells, suggesting that either CD36− cells can convert into CD36+ cells in vivo, or that a percentage of cells scored as CD36− by FACS express the CD36 mRNA but not the protein. Interestingly, while co-culturing parental OSCC cells with OP9-derived adipocytes significantly increased the number of CD36+ cells, a percentage of tumour cells remained CD36− (FIG. 10D, FIG. 11); the inventors surmised that these cells might represent the bona fide CD36 negative population. In fact, the mRNA expression of CD36 was significantly lower in CD36− cells sorted from OSCC cells co-cultured with adipocytes, than those isolated from monocultures of OSCC cells (FIG. 15). The inventors therefore FACS-sorted CD36+ and CD36− cells from OSCC cells co-cultured with adipocytes, and then orthotopically inoculated them separately into NSG mice to assess their metastatic potential (FIG. 16A). Under these conditions, CD36− cells did not generate even a single LN metastasis, whereas CD36+ cells formed LN metastases even with a higher penetrance than the parental cells (FIGS. 17B, 17C, 17G). This effect was independent of the primary tumour growth, since both CD36+ and CD36− cells generated oral lesions with 100% efficiency and a similar tumour size (FIGS. 10B, 10D).

Orthotopic inoculation of limiting dilutions determined that approximately 1/3000 CD36+/CD44$^{bright}$ cells harbour metastatic potential, a ten-fold increase compared to the entire CD44$^{bright}$ population, as can be seen in Table 4 below and in FIG. 16F:

TABLE 4

Frequency of metastasis and primary tumours observed after orthotopic inoculation of limiting dilutions

| | Cells injected | Metastasis+/ total mice | MIC frequency 0.95 confidence interval |
|---|---|---|---|
| CD44bright | 50,000 | 4/10 | Lower: 1/67325 |
| | 20,000 | 3/5 | Estimate: 1/37099 |
| | 10,000 | 5/9 | Upper: 1/20444 |
| | 1000 | 2/10 | |
| | 100 | 0/10 | |
| CD36 + CD44bright | 50,000 | 8/8 | Lower: 1/6772 |
| | 20,000 | 5/5 | Estimate: 1/3432 |
| | 10,000 | 7/10 | Upper: 1/1740 |
| | 1000 | 5/10 | |
| | 100 | 5/15 | |
| CD36 − CD44bright | 50,000 | 0/10 | Lower: 1/inf |
| | 10,000 | 0/6 | Estimate: 1/inf |
| | 1000 | 0/6 | Upper: 1/189136 |
| | 100 | 0/6 | |

TABLE 4-continued

Frequency of metastasis and primary tumours observed after orthotopic inoculation of limiting dilutions

| | Cells injected | Primary tumour/ total mice | TIC frequency 0.95 confidence interval |
|---|---|---|---|
| CD44bright | 50,000 | 10/10 | Lower: 1/2290 |
| | 20,000 | 5/5 | Estimate: 1/1069 |
| | 10,000 | 9/9 | Upper: 1/499 |
| | 1000 | 6/10 | |
| | 100 | 1/10 | |
| CD36 + CD44bright | 50,000 | 8/8 | Lower: 1/1864 |
| | 20,000 | 5/5 | Estimate: 1/916 |
| | 10,000 | 10/10 | Upper: 1/450 |
| | 1000 | 7/10 | |
| | 100 | 1/15 | |
| CD36 − CD44bright | 50,000 | 10/10 | Lower: 1/6378 |
| | 10,000 | 5/6 | Estimate: 1/2354 |
| | 1000 | 3/6 | Upper: 1/869 |
| | 100 | 3/6 | |

Figure 16C:
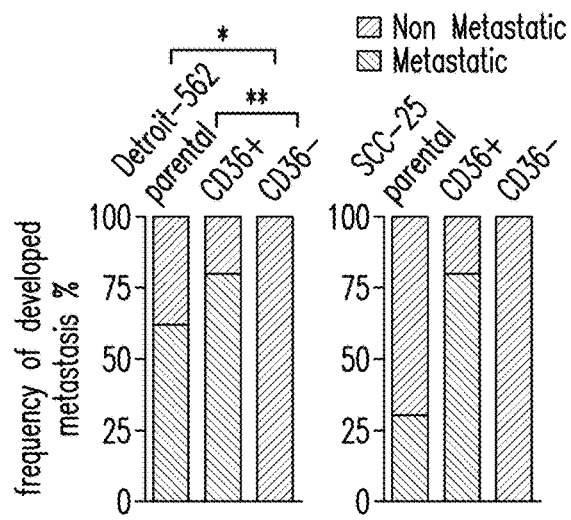
Figure 16D:
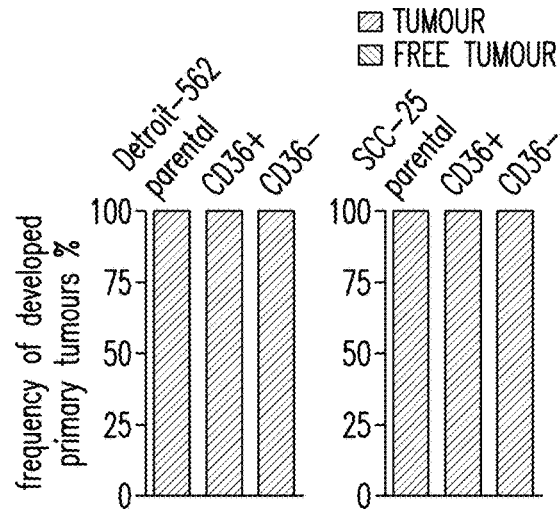
Figure 16E:
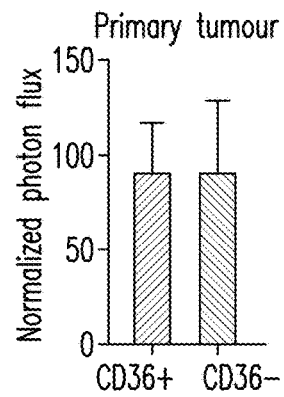
Figure 16F:
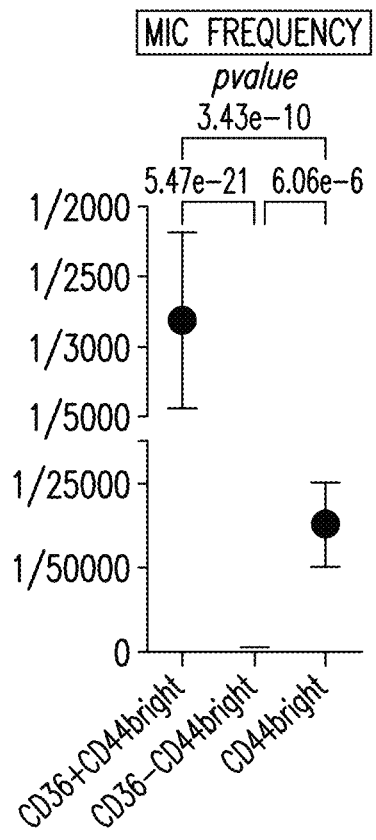
Figure 16G:
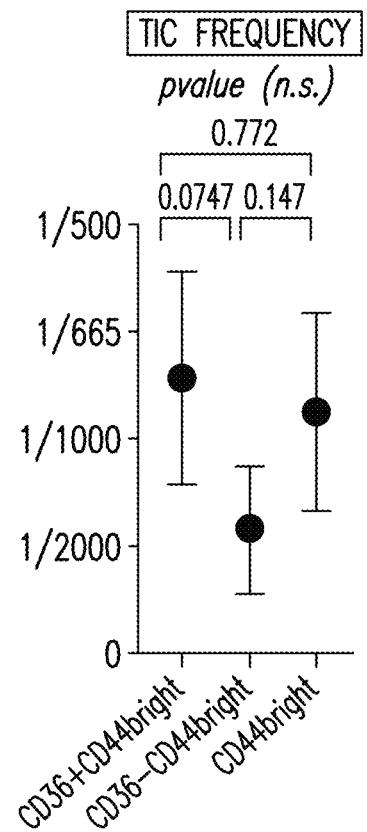

On the other hand, and importantly, both populations displayed the same primary oral tumour-initiating potential (FIGS. 16G, 17A, 17C), and CD36+/CD44$^{bright}$ cells were only slightly more tumourigenic in the oral cavity than their CD36−/CD44$^{bright}$ counterparts, although these differences were not statistically significant (FIGS. 16E, 16F). Considering that CD36/CD44$^{bright}$ were incapable of generating a single metastasis (FIGS. 16C, 16E), these results therefore indicate that CD36+/CD44$^{bright}$ cells constitute the metastasis-initiating population in oral SCC.

Furthermore, gene expression analysis of CD36+ and CD36− cells sorted either from primary oral lesions generated upon inoculation of parental OSCCs (Detroit-562), or sorted from LN metastases generated upon inoculation of CD36+/CD44$^{bright}$ cells, indicated that their gene expression signatures were very similar. In this sense, CD36+ cells located at the LN metastases were also strongly defined by GO categories indicative of lipid metabolism such as response to lipid, regulation of lipid storage, and fatty acid metabolic process, or pathways such as CD36 or PPAR-gamma, just as their CD36+ counterparts located in the oral lesion. Thus, these results indicate that when transplanted, CD36+ cells are not only capable of initiating metastasis, but also of recapitulating their molecular and cellular heterogeneity from the primary origin, hence constituting bona fide metastatic stem cells.

These results therefore indicate that CD36+ cells constitute the metastasis-initiating population in oral SCC.

Example 4.—Anti-Metastatic Potentiality of Blocking CD36

To determine whether targeting CD36 would be a feasible anti-metastatic strategy against human OSCCs, the inventors used alternative strategies with two different anti-CD36 neutralizing antibodies: one that inhibits all known functions of CD36, including its interaction with thrombospondin, collagens and fatty acids (FA6.152), and the other that only blocks fatty acid and oxLDL uptake (JC63.1) (Kermovant-Duchemin, et al., 2005; Mwaikambo et al., 2006).

Figure 18A:
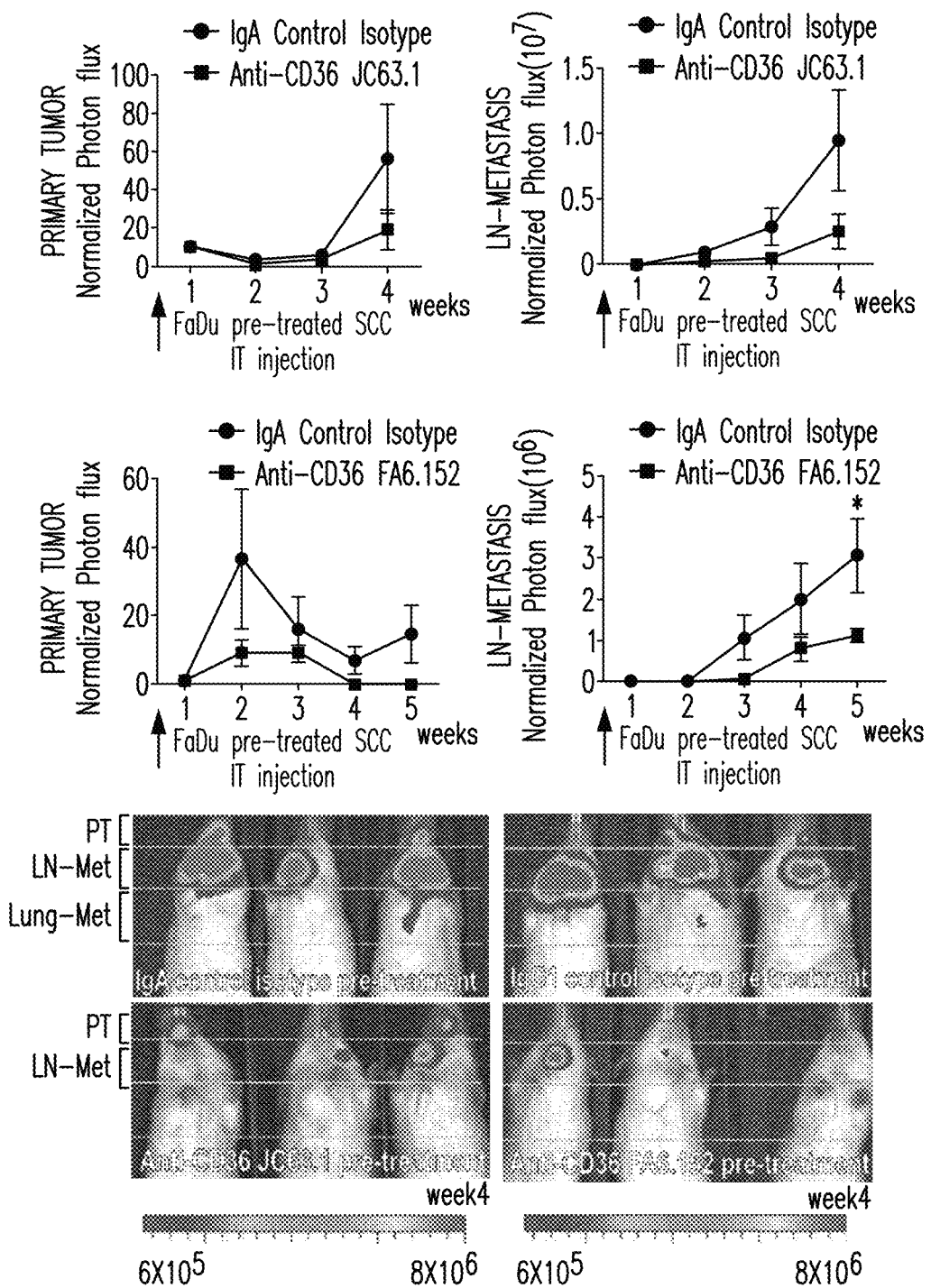
FIGS. 18A-18L. CD36-blocking antibodies prevent and inhibit metastasis of OSCC tumours.
Figure 18B:
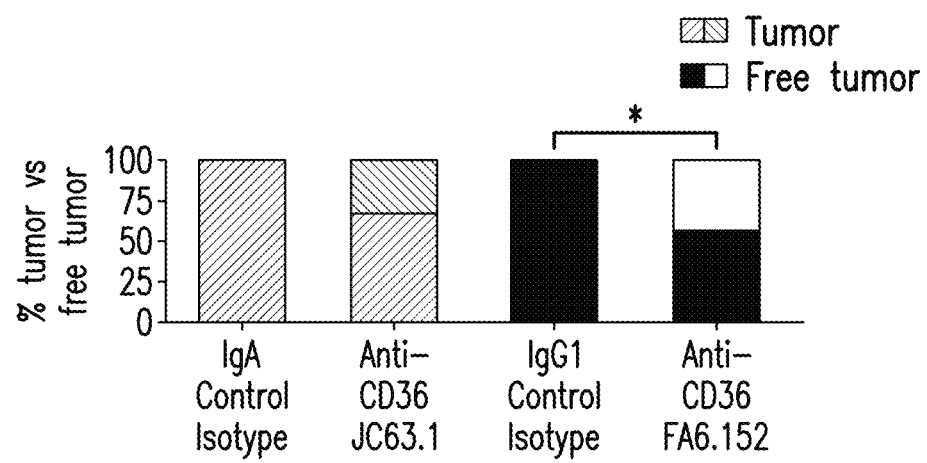
Figure 18C:
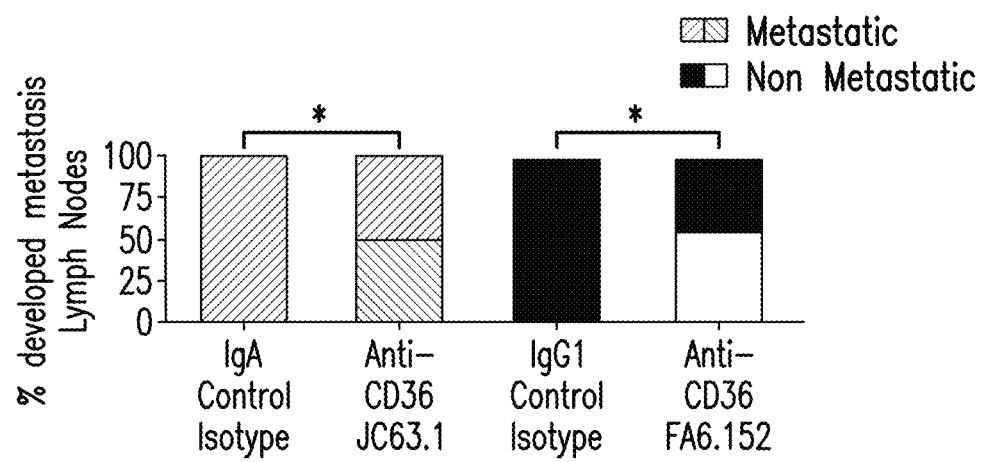
Figure 19A:
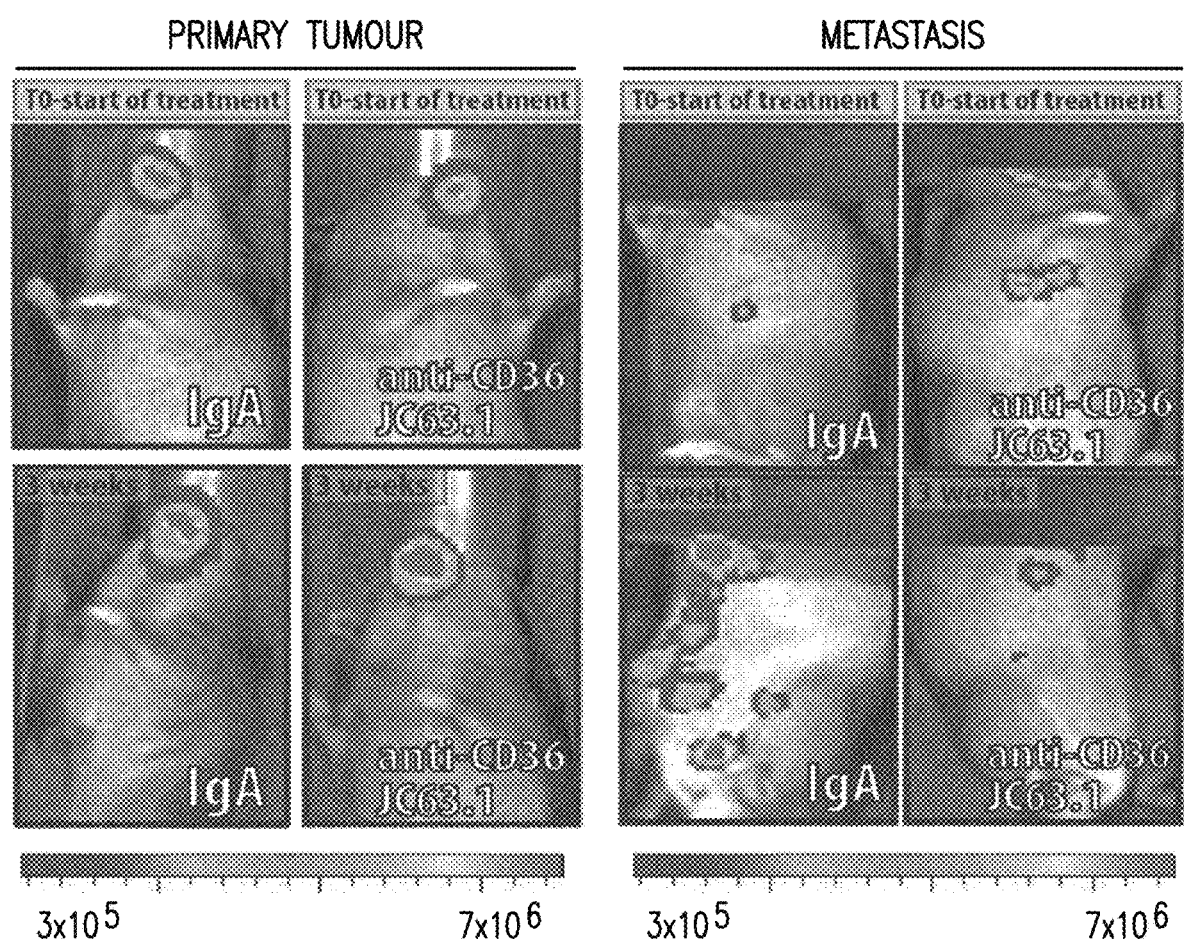
FIGS. 19A-19C.
Figure 19B:
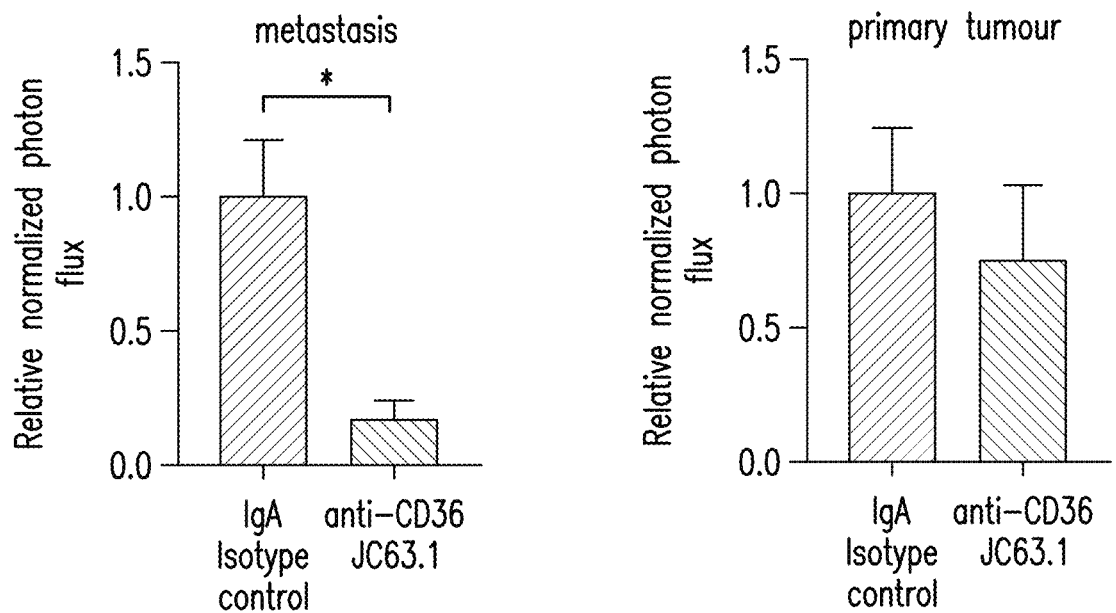
Figure 19C:
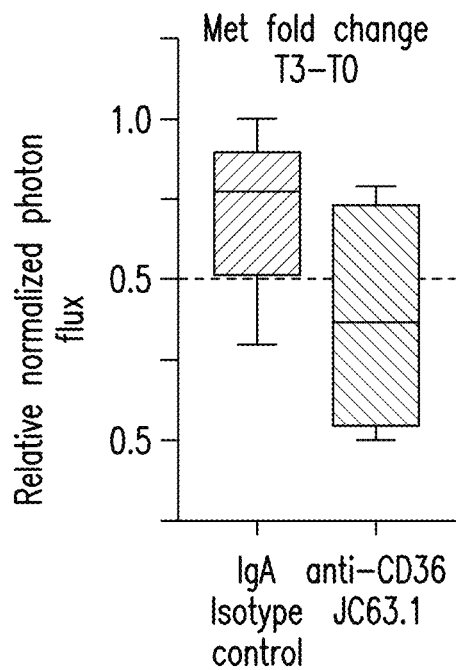

First, pre-treatment of OSCC cells in culture with either blocking antibody only slightly reduced the size of the oral lesions, yet significantly inhibited LN metastasis when inoculated in vivo (FIG. 18A). In addition, pre-treatment with either antibody reduced the penetrance of oral lesions by 25-30% (FIG. 19B). Only 50% of the mice inoculated with OSCC cell pre-treated with the blocking CD36 antibodies harbouring primary tumours, presented LN metastases (FIG. 11C), further underscoring the selective effect of CD36 in promoting LN metastasis.

Figure 18D:
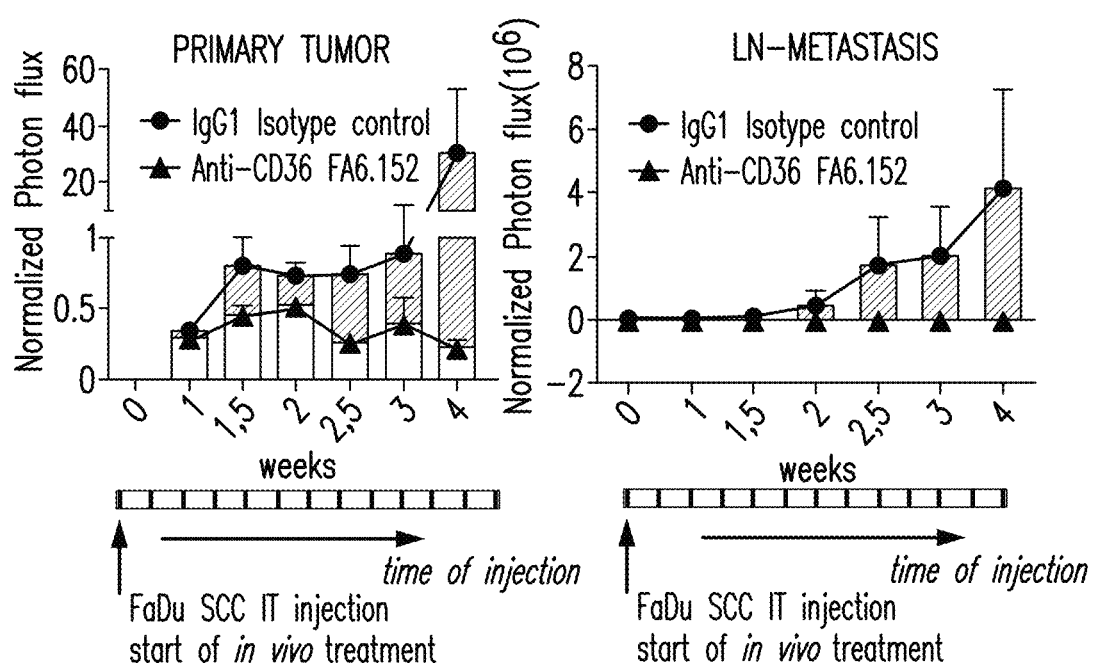
Figure 18E:
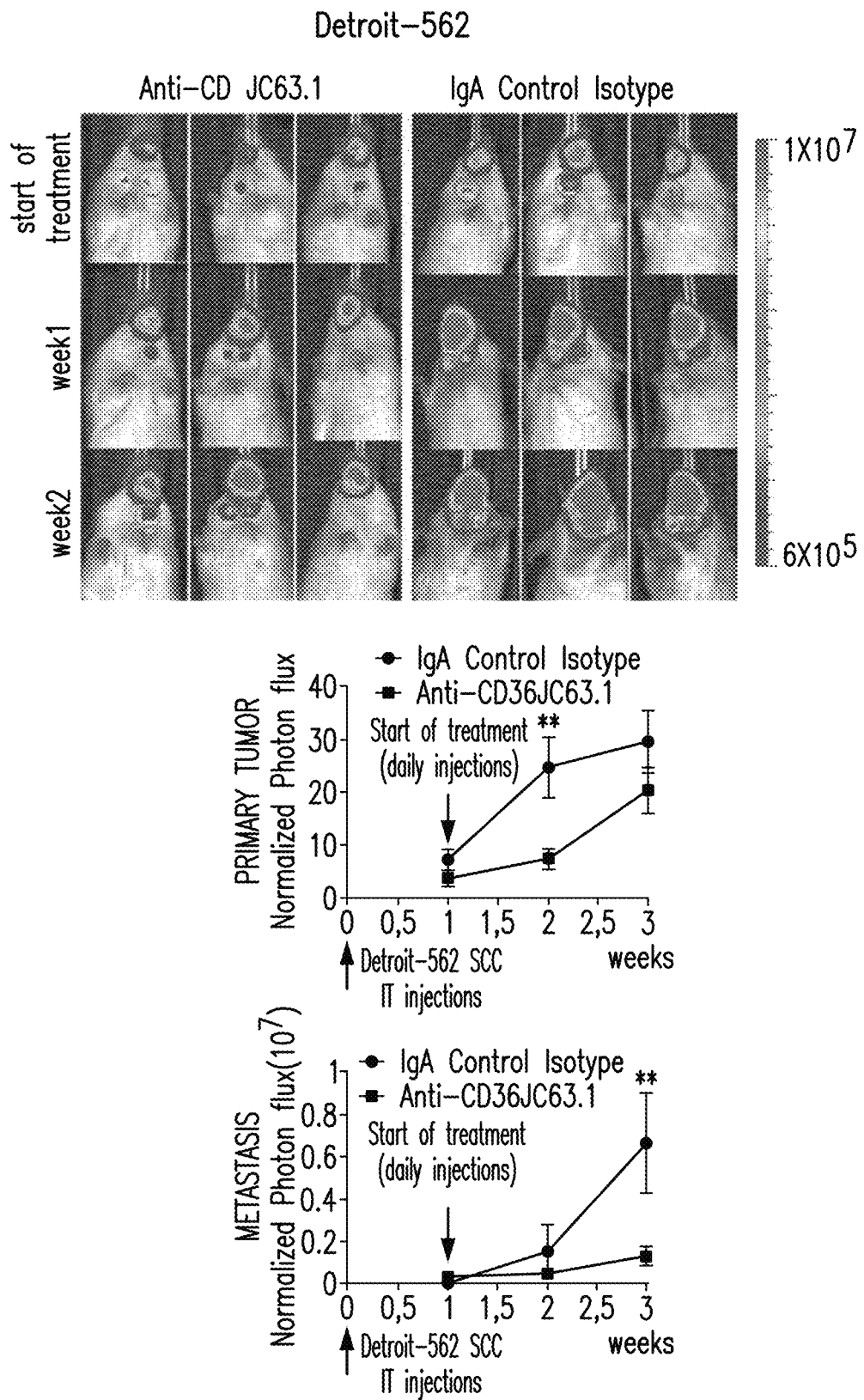
Figure 18F:
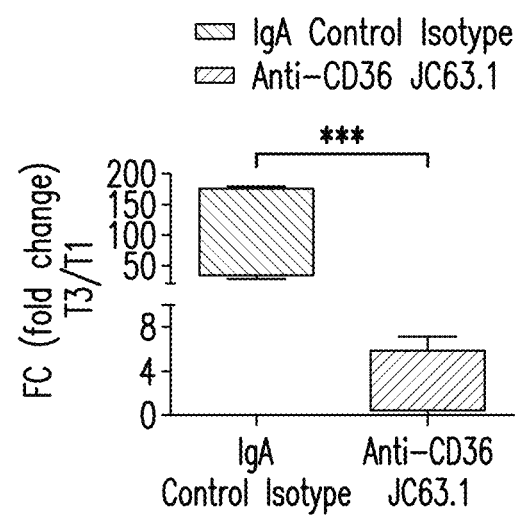
Figure 18G:
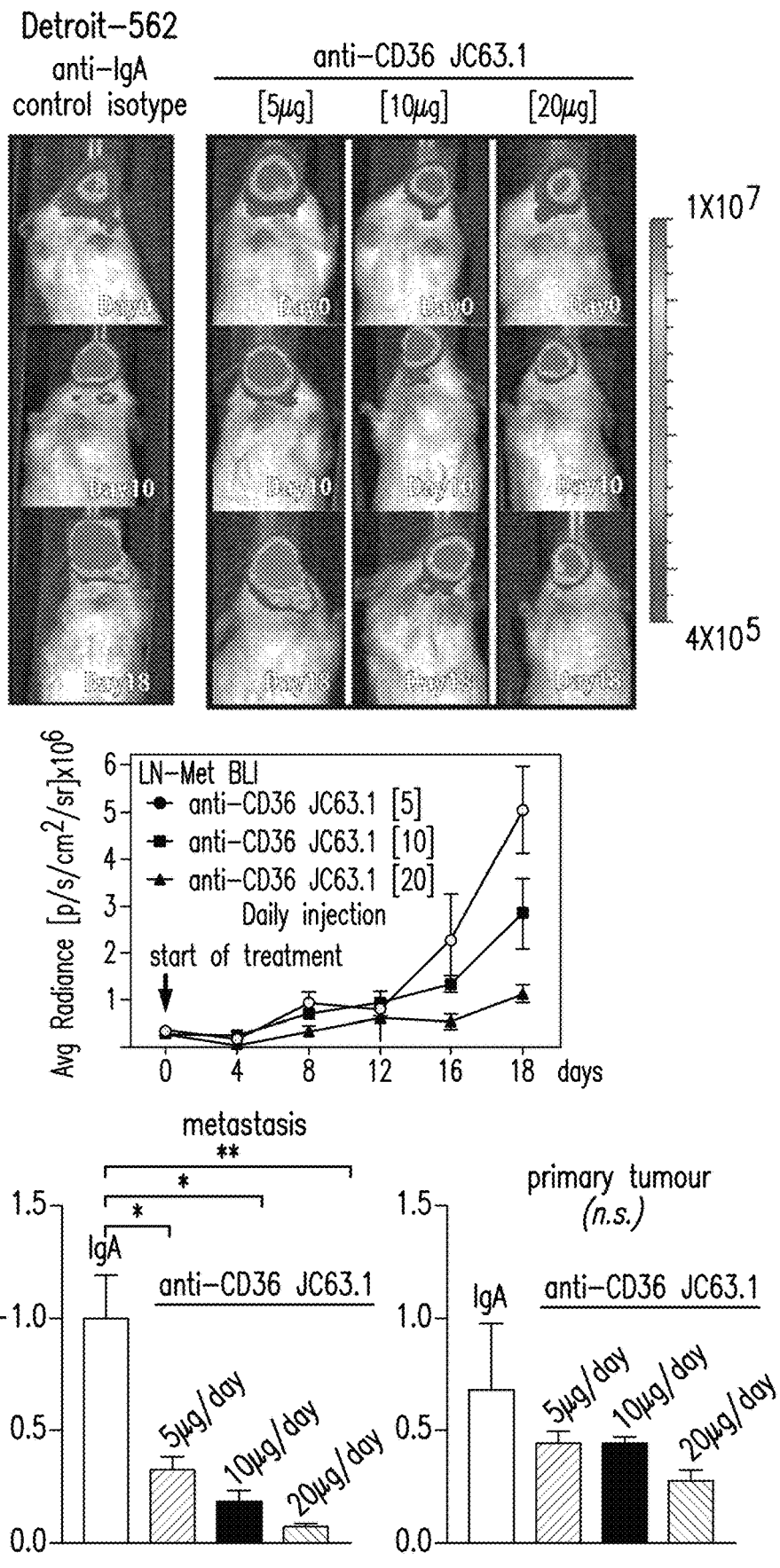
Figure 18H:
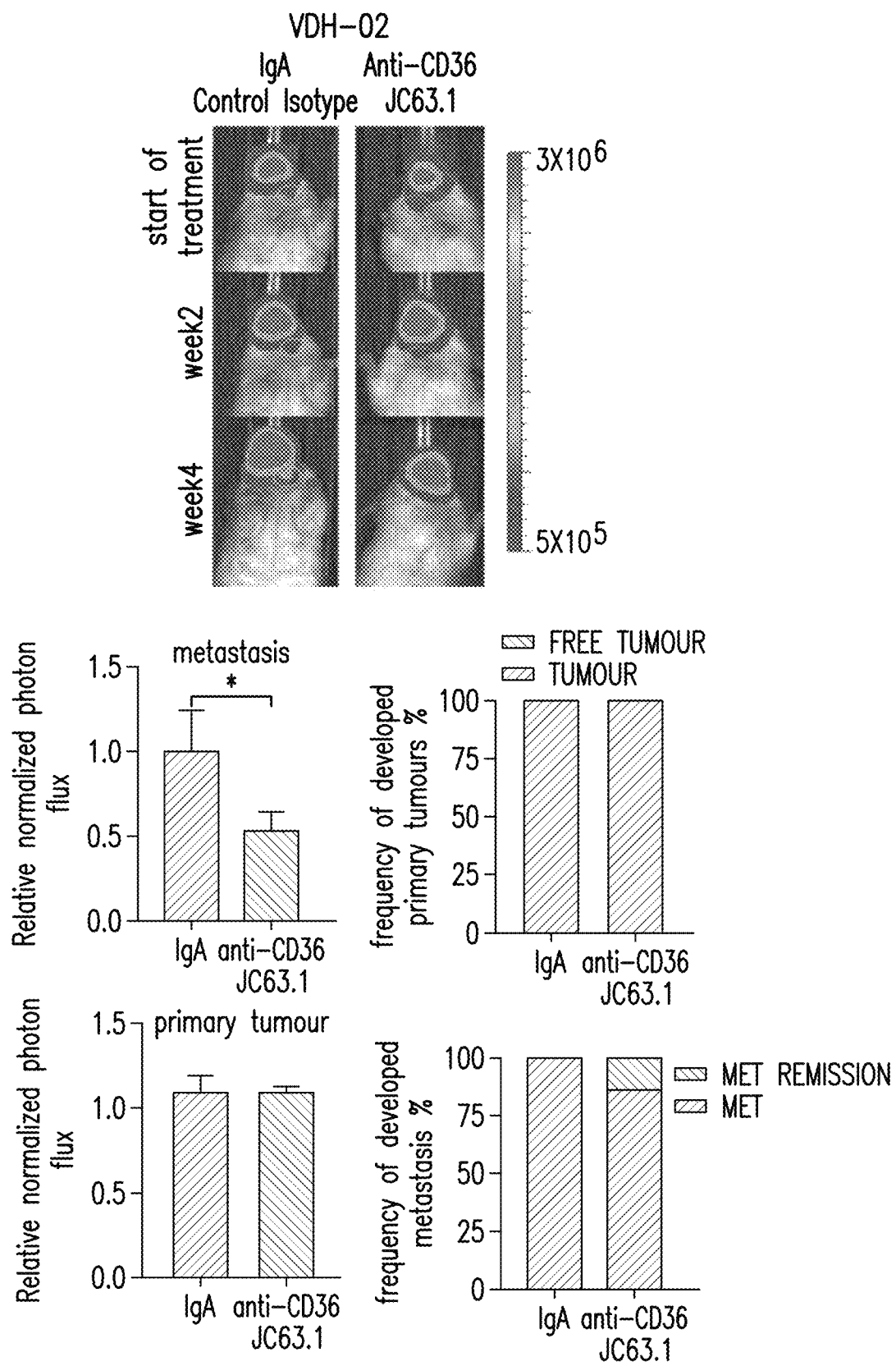
Figure 18I:
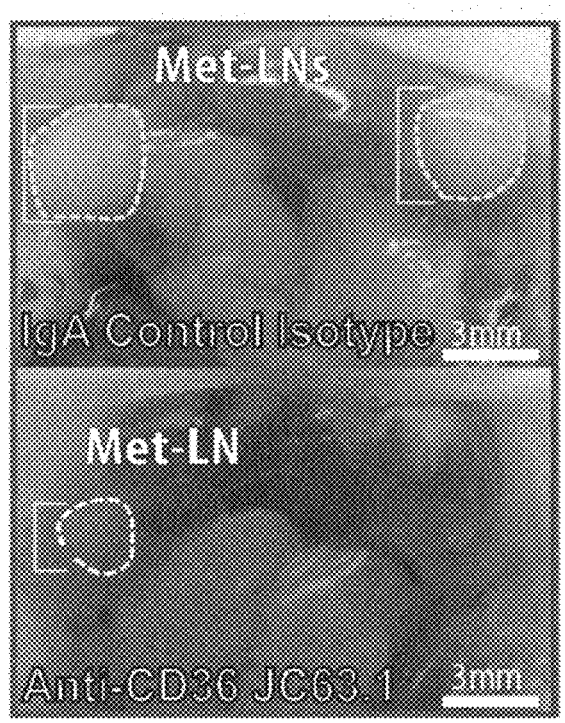
Figure 18J:
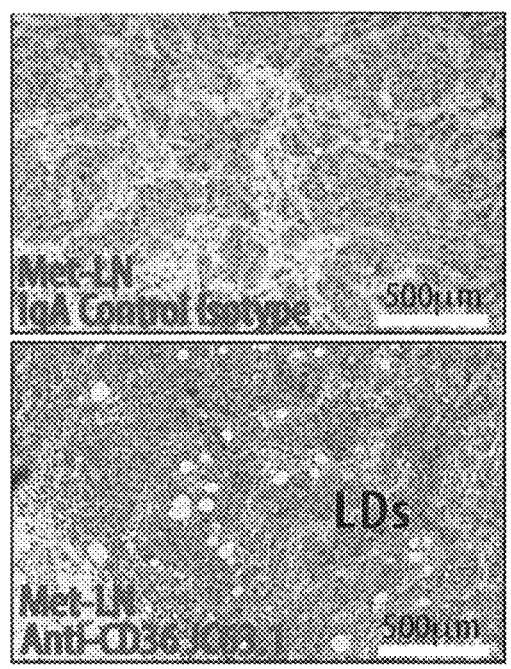

Additionally, the group of the inventors treated mice with either antibody intraperitoneally every 3 days after orally inoculating the tumour cells. This resulted in a significant reduction of the size of the primary tumours, without affecting the number of mice that developed primary tumours and completely inhibited metastasis initiation, preventing any metastatic growth in the LNs (FIG. 18D).

Also additionally, and most importantly, when the inventors treated mice that had already developed LN metastasis from OSCC and PDCs with daily intraperitoneal injections of the neutralizing CD36 antibody (JC63.1), the size of the LN metastases was reduced more than 80%-90%, with some lesions (15% of the injected animals) showing complete remission in a manner dependent on the dose of the administered antibody (FIGS. 18A, 18E-18G). On the other hand, the oral lesions did not show a statistically significant difference in size at the endpoint (FIGS. 18B, 18C, 18E-18H). Large cells swollen with lipids accumulated in the LN metastases of mice treated with CD36 neutralizing antibodies, similar to the shRNA-mediated knockdown of CD36 (FIG. 18J, FIGS. 5F-5I) or to the results obtained upon expression of the CD36 mutant defective in lipid internalization (FIGS. 13A-13C).

Figure 18K:
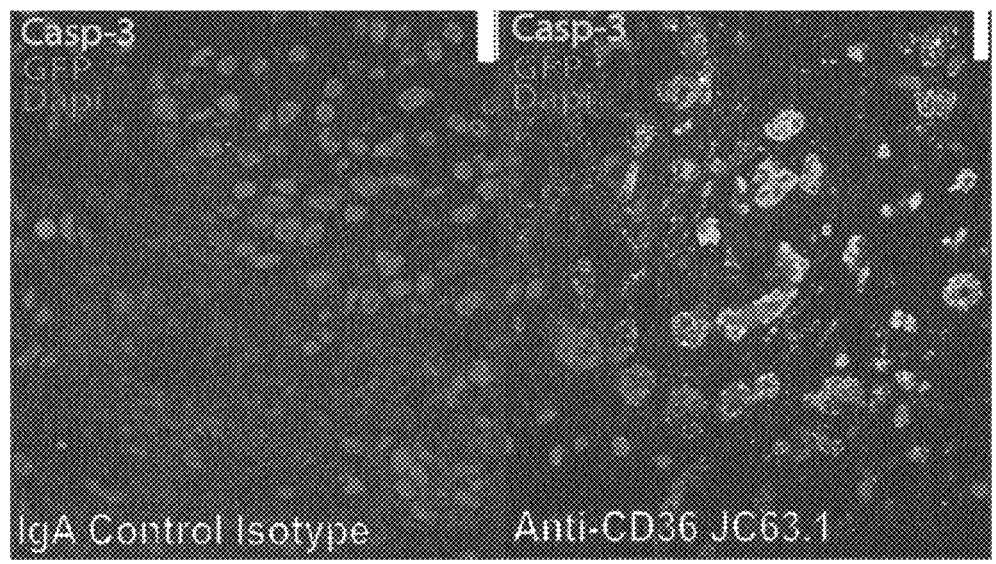
Figure 18L:
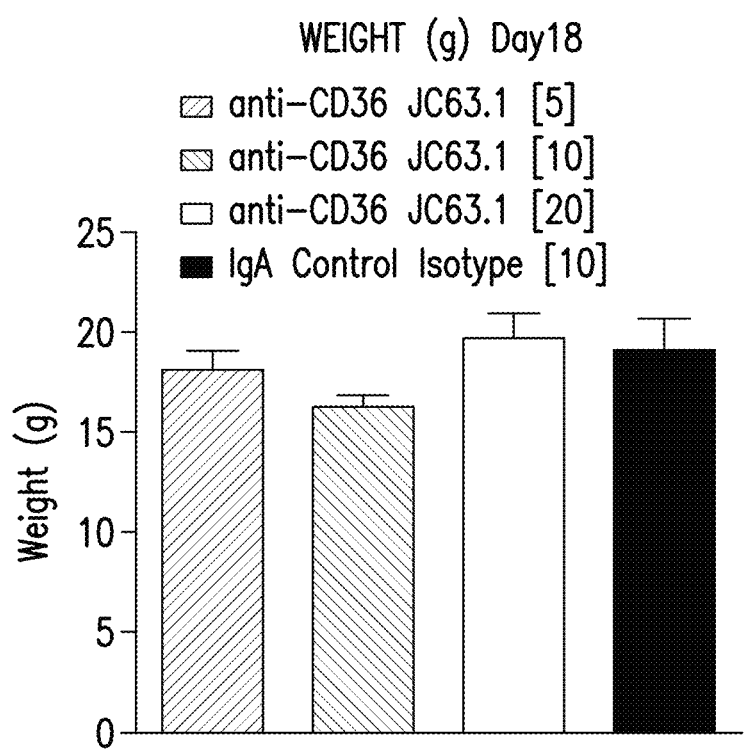

Treatment with JC63.1 antibody induced lipotoxicity as determined to high Caspase 3 immunoreactivity (FIG. 18K). Since the JC63.1 antibody specifically inhibits the interaction of CD36 with fatty acids, and exerted the same anti-metastatic effect than the broad FA6.152 CD36 neutralizing antibody, these results indicated that the pro-metastatic effect of CD36 in OSCC mainly relied on its ability to modulate lipid metabolism, rather than its other known functions, however, it cannot be ruled out that inhibition of other functions of CD36, such as its ability of interacting with thrombospondin 1-2, with oxidized LDL, or with collagens, might also contribute to the anti-metastatic effect. In fact, some additional assays indicate that knockdown of CD36 significantly reduces the initial homing of GFP-tagged OSCC cells to the lung, without affecting their attachment to the oral cavity, as determined by RT-cPCR of GFP (FIG. 20). No mice developed any visible side effects from the continuous treatment with CD36-neutralizing antibodies, in particular, they did not lose any weight (FIG. 18L).

Figure 20A:
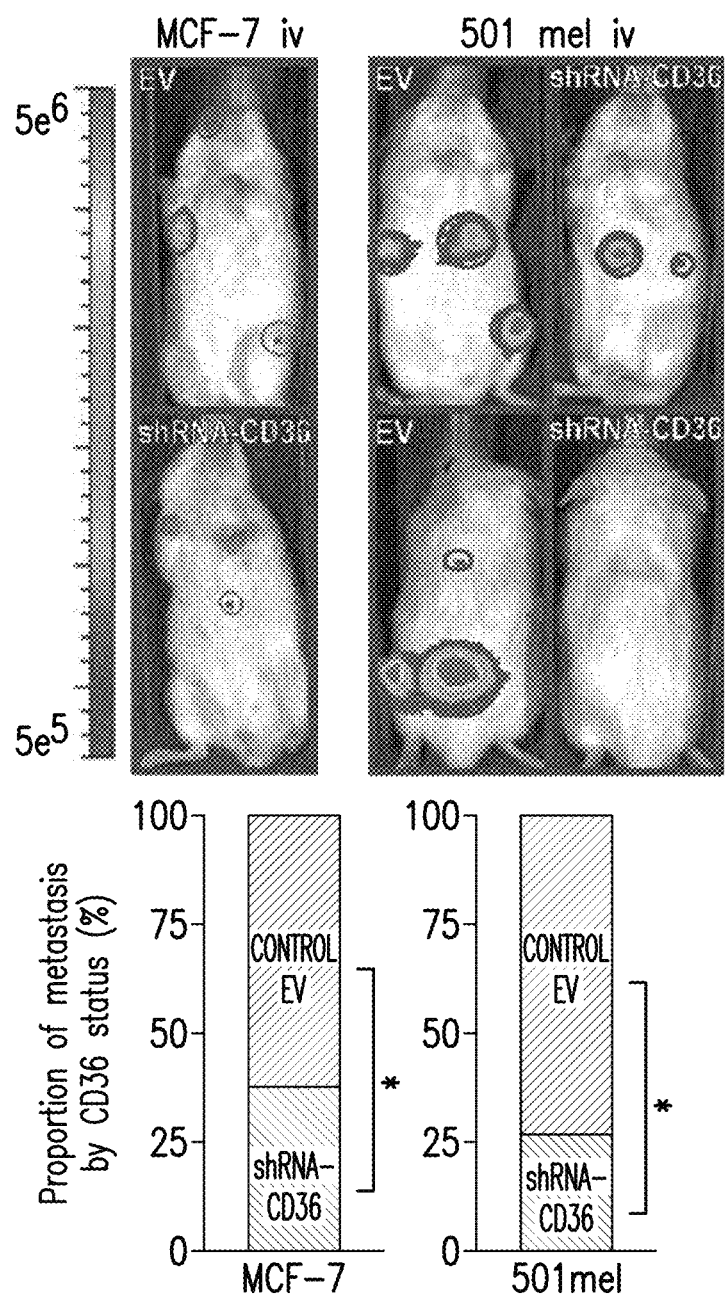
FIGS. 20A-20B. CD36 depletion inhibits metastatic spread of melanoma and breast cancer cells.
Figure 20B:
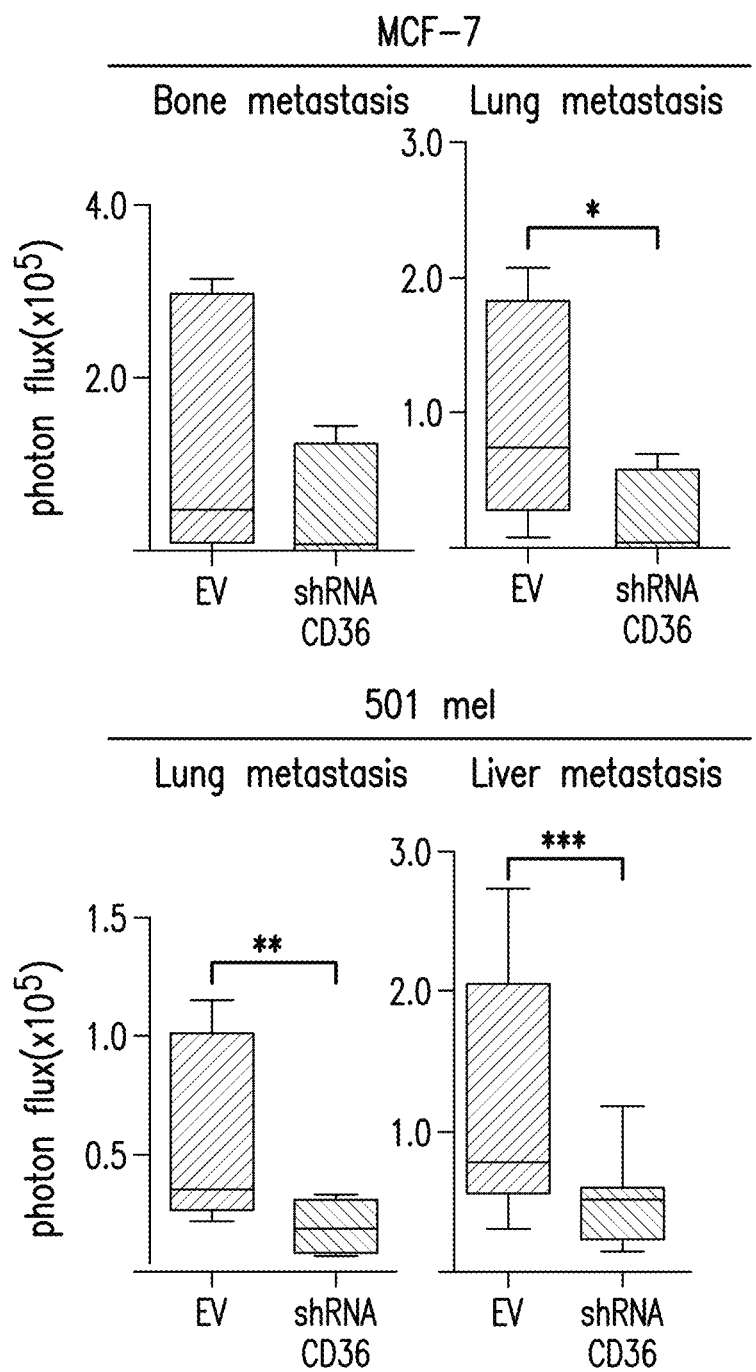
Figure 21A:
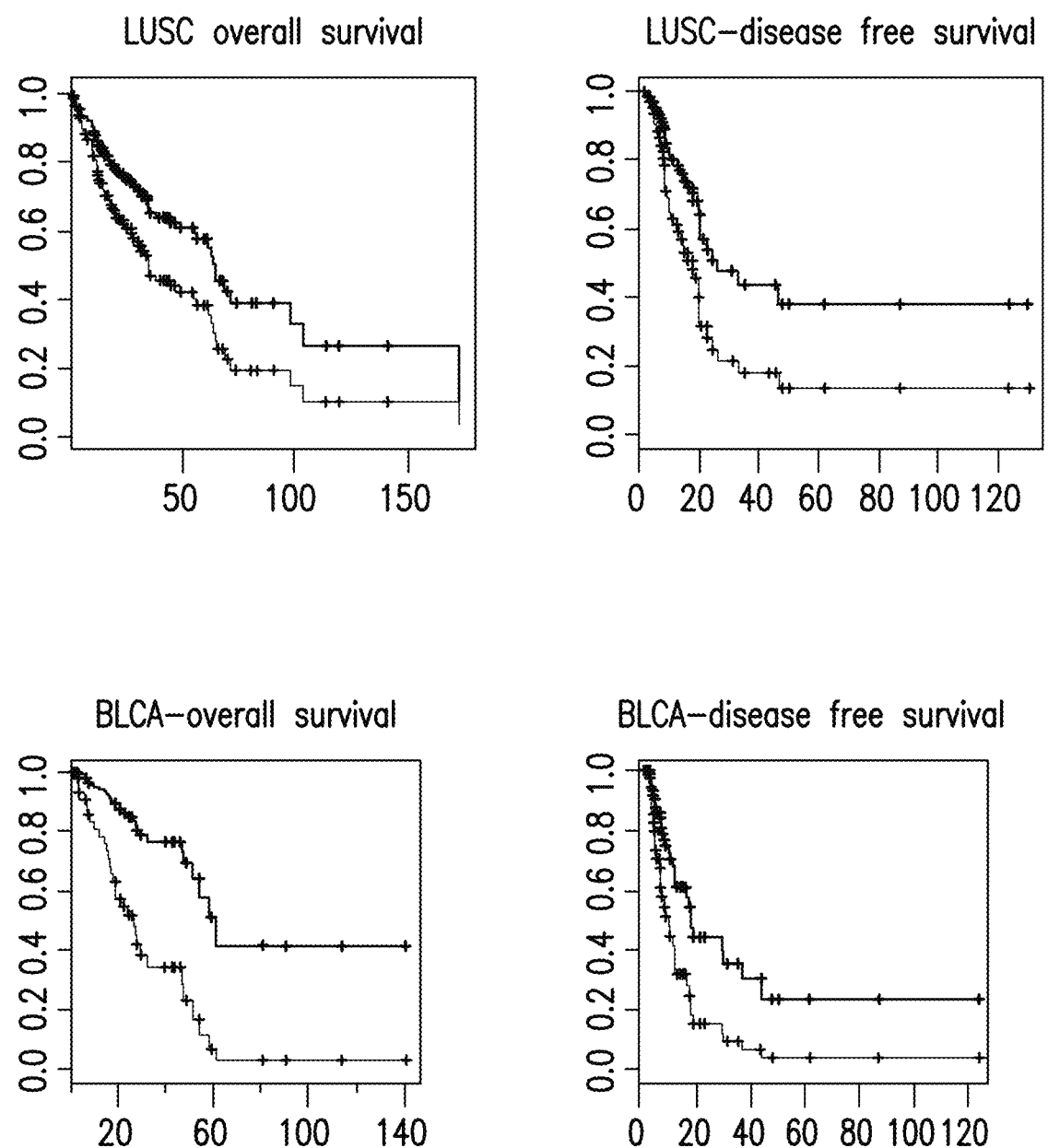
FIGS. 21A-21B.
Figure 21B:
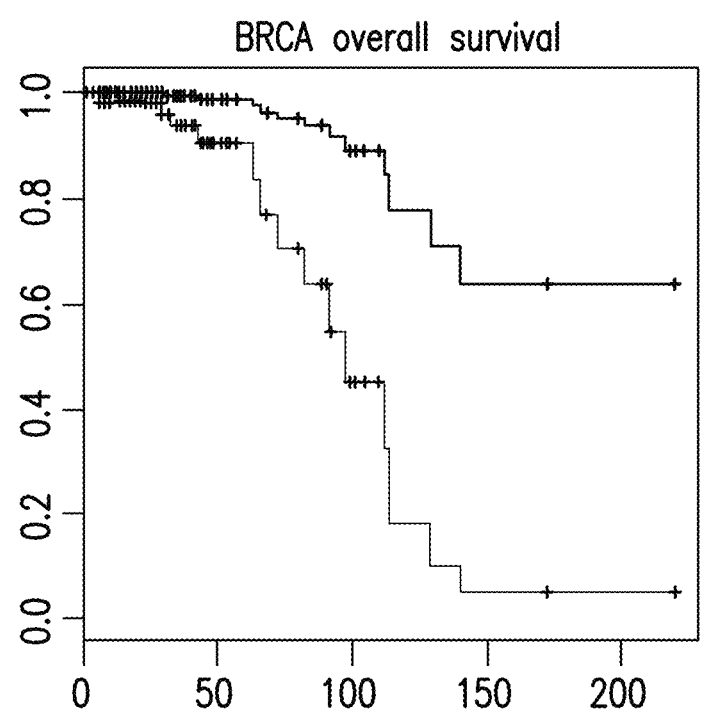

Example 5.—CD36 is Associated with Metastasis and Poor Prognosis in Human Tumours The present inventors analysed publicly, available, but raw, data in databases, searching for more data about CD36 and correlation with cancer. Further underscoring the important role of CD36 in tumour progression, they found that CD36 expression, or its associated signature, strongly correlated with a poor rate of disease-free survival and overall survival in patients with lung SCC, bladder cancer or luminal A breast cancer (FIG. 21). In addition, CD36 amplification specifically correlates with metastasis in a large number of human tumours including highly aggressive ones such as melanoma (Nath & Chan, 2016). In fact, when NSG mice were inoculated intravenously with a luminal A breast cancer (MCF-7) or a human melanoma (501mel) cell line lacking CD36, a significant reduction in both the number and size of lung, bone and liver metastases was observed as compared to controls (FIGS. 20A, 20B).

REFERENCES

Alghazeer R., et al. Cytotoxicity of oxidised lipids in cultured colonal human intestinal cancer cells (caco-2 cells). Toxicology Letters, 180, 202-211. (2008).

Almagro J. C. and Fransson J. Humanization of antibodies. Frontiers in Bioscience 13, 1619-1633 (2008).

Antibodies: A Laboratory Manual, Second edition", edited by E. A. Greenfield. Cold Spring Harbour Laboratory Press, 2014.

Balaban S., et al., Obesity and Cancer Progression: Is there a Role of fatty acid metabolism?. BioMed Research International, volume 2015 (2015), Article iD 274585, dx.doi.org/10.1155/2015/274585

Barrett, T. & Edgar, R. Gene expression omnibus: microarray data storage, submission, retrieval, and analysis. *Methods Enzymol* 411, 352-369, doi:10.1016/S0076-6879 (06)11019-8 (2006).

Benjamini, Y. H. Y. Controlling the False Discovery Rate: A Practical and Powerful Approach to Multiple Testing. *Journal of the Royal Statistical Society. Series B (Methodological)* 57, 289-300 (1995).

Berriz, G. F., King, O. D., Bryant, B., Sander, C. & Roth, F. P. Characterizing gene sets with FuncAssociate. *Bioinformatics* 19, 2502-2504 (2003).

Bragado, P. et al. Analysis of marker-defined HNSCC subpopulations reveals a dynamic regulation of tumor initiating properties. PloS one 7, e29974, doi:10.1371/journal.pone.0029974 (2012).

Calon, A. et al. Dependency of colorectal cancer on a TGF-beta-driven program in stromal cells for metastasis initiation. Cancer cell 22, 571-584, doi:10.1016/j.ccr.2012.08.013 (2012)

Calon, A. et al. Stromal gene expression defines poor-prognosis subtypes in colorectal cancer. Nature genetics 47, 320-329, doi:10.1038/ng.3225 (2015).

Cao, Z. et al. Angiocrine factors deployed by tumor vascular niche induce B cell lymphoma invasiveness and chemoresistance. Cancer cell 25, 350-365, doi:10.1016/j.ccr.2014.02.005 (2014).

Cerami, E. et al. The cBio cancer genomics portal: an open platform for exploring multidimensional cancer genomics data. *Cancer Discov* 2, 401-404, doi:10.1158/2159-8290.CD-12-0095 (2012).

Chaffer, C. L. & Weinberg, R. A. A perspective on cancer cell metastasis. Science 331, 1559-1564, doi:10.1126/science.1203543 (2011).

Chen, Q., Zhang, X. H. & Massague, J. Macrophage binding to receptor VCAM-1 transmits survival signals in breast cancer cells that invade the lungs. Cancer cell 20, 538-549, doi:10.1016/j.ccr.2011.08.025 (2011).

Chen, J. et al. A restricted cell population propagates glioblastoma growth after chemotherapy. Nature 488, 522-526, doi:10.1038/nature11287 (2012).

Coburn, C. T. et al. Defective uptake and utilization of long chain fatty acids in muscle and adipose tissues of CD36 knockout mice. The Journal of biological chemistry 275, 32523-32529, doi:10.1074/jbc.M003826200 (2000).

Cole, S. P. C. et al., in: Monoclonal Antibodies and Cancer Therapy, Alan R. Liss, Inc., pp. 77-96 (1985)

Cote, R. J. et al. Generation of human monoclonal antibodies reactive with cellular antigens. Proc Natl Acad Sci USA 80(7), 2026-2030 (1983).

Dean, C. B. and Nielsen, J. D. R: A language and environment for statistical computing. *R Foundation for Statistical Computing* (2008).

DeFilippis, R. A., et al. CD36 repression activates a multicellular stromal program shared by high mammographic density and tumor tissues. Cancer Discov. 2(9):826-39 (2012).

Ellis, J. M. et al. Adipose acyl-CoA synthetase-1 directs fatty acids toward beta-oxidation and is required for cold thermogenesis. Cell metabolism 12, 53-64, doi:10.1016/j.cmet.2010.05.012 (2010).

Gleber-Netto, F. O. et al. Molecular events in relapsed oral squamous cell carcinoma: Recurrence vs secondary primary tumor. Oral oncology 51, 738-744, doi:10.1016/j.oraloncology.2015.04.016 (2015).

Gao, J. et al. Integrative analysis of complex cancer genomics and clinical profiles using the cBioPortal. *Sci Signal* 6, p11, doi:10.1126/scisignal.2004088 (2013).

Gentleman, R. C. et al. Bioconductor: open software development for computational biology and bioinformatics. *Genome Biol* 5, R80, doi:10.1186/gb-2004-5-10-r80 (2004).

Goel, H. L. & Mercurio, A. M. VEGF targets the tumour cell. Nature reviews. Cancer 13, 871-882, doi:10.1038/nrc3627 (2013).

Gonzalez-Roca, E. et al. Accurate expression profiling of very small cell populations. *PLoS One* 5, e14418, doi:10.1371/journal.pone.0014418 (2010).

Hale, J. S. et al. Cancer stem cell-specific scavenger receptor 36 drives glioblastoma progression. Stem Cells 32(7):1756-58 (2014).

Ibrahimi, A. et al. Muscle-specific overexpression of FAT/CD36 enhances fatty acid oxidation by contracting muscle, reduces plasma triglycerides and fatty acids, and increases plasma glucose and insulin. The Journal of biological chemistry 274, 26761-26766 (1999).

Irizarry, R. A. et al. Exploration, normalization, and summaries of high density oligonucleotide array probe level data. *Biostatistics* 4, 249-264, doi:10.1093/biostatistics/4.2.249 (2003).

Kalluri, R. & Zeisberg, M. Fibroblasts in cancer. Nature reviews. Cancer 6, 392-401, doi:10.1038/nrc1877 (2006).

Kermorvant-Duchemin, E. et al. Trans-arachidonic acids generated during nitrative stress induce a thrombospondin-1-dependent microvascular degeneration. Nature medicine 11, 1339-1345, doi:10.1038/nm1336 (2005).

Kohler, G. & Milstein, C. Continuous cultures of fused cells secreting antibody of predefined specificity. Nature 256, 495-497 (1975).

Kreso, A. et al. Variable clonal repopulation dynamics influence chemotherapy response in colorectal cancer. Science 339, 543-548, doi:10.1126/science.1227670 (2013).

Lu, X. et al. VCAM-1 promotes osteolytic expansion of indolent bone micrometastasis of breast cancer by engaging alpha4beta1-positive osteoclast progenitors. Cancer cell 20, 701-714, doi:10.1016/j.ccr.2011.11.002 (2011).

Nowak, J. A. & Fuchs, E. Isolation and culture of epithelial stem cells. *Methods Mol Biol* 482, 215-232, doi:10.1007/978-1-59745-060-7_14 (2009).

Malanchi, I. et al. Interactions between cancer stem cells and their niche govern metastatic colonization. Nature 481, 85-89, doi:10.1038/nature10694 (2012).

Myers, J. N., Holsinger, F. C., Jasser, S. A., Bekele, B. N. & Fidler, I. J. An orthotopic nude mouse model of oral tongue squamous cell carcinoma. Clinical cancer research: an official journal of the American Association for Cancer Research 8, 293-298 (2002).

Mwaikambo, B. R., Sennlaub, F., Ong, H., Chemtob, S. & Hardy, P. Activation of CD36 inhibits and induces regression of inflammatory corneal neovascularization. Investigative ophthalmology & visual science 47, 4356-4364, doi:10.1167/iovs.05-1656 (2006)

Nath, A. & Chan, C. Genetic alterations in fatty acid transport and metabolism genes are associated with metastatic progression and poor prognosis of human cancers. *SciRep* 6, 18669, doi:10.1038/srep18669 (2016)

Nieman, K. M. et al. Adipocytes promote ovarian cancer metastasis and provide energy for rapid tumor growth. Nature medicine 17, 1498-1503, doi:10.1038/nm.2492 (2011).

Oskarsson, T., Batlle, E. & Massague, J. Metastatic stem cells: sources, niches, and vital pathways. *Cell stem cell* 14, 306-321, doi:10.1016/j.stem.2014.02.002 (2014).

Obenauf, A. C. et al. Therapy-induced tumour secretomes promote resistance and tumour progression. Nature 520, 368-372, doi:10.1038/nature14336 (2015).

Oskarsson, T. et al. Breast cancer cells produce tenascin C as a metastatic niche component to colonize the lungs. Nature medicine 17, 867-874, doi:10.1038/nm.2379 (2011).

Pece, S. et al. Biological and molecular heterogeneity of breast cancers correlates with their cancer stem cell content. Cell 140, 62-73, doi:10.1016/j.cell.2009.12.007 (2010).

Peinado, H. et al. Melanoma exosomes educate bone marrow progenitor cells toward a pro-metastatic phenotype through MET. Nature medicine 18, 883-891, doi:10.1038/nm.2753 (2012).

Pepino, M. Y., Kuda, O., Samovski, D. & Abumrad, N. A. Structure-function of CD36 and importance of fatty acid signal transduction in fat metabolism. Annual review of nutrition 34, 281-303, doi:10.1146/annurev-nutr-071812-161220 (2014).

Qin, J. et al. The PSA(-/lo) prostate cancer cell population harbors self-renewing long-term tumor-propagating cells that resist castration. Cell stem cell 10, 556-569, doi:10.1016/j.stem.2012.03.009 (2012).

Spangenburg, E. E., Pratt, S. J., Wohlers, L. M. & Lovering, R. M. Use of BODIPY (493/503) to visualize intramuscular lipid droplets in skeletal muscle. *J Biomed Biotechnol* 2011, 598358, doi:10.1155/2011/598358 (2011).

Smyth, G. Limma: linear models for microarray data. In: 'Bioinformatics and Computational Biology Solutions using R and Bioconductor. Springer, New York, 397-420 (2005).

Subramanian, A. et al. Gene set enrichment analysis: a knowledge-based approach for interpreting genome-wide expression profiles. *Proc Natl Acad Sci USA* 102, 15545-15550, doi:10.1073/pnas.0506580102 (2005).

Zhang, X. H. et al. Selection of bone metastasis seeds by mesenchymal signals in the primary tumor stroma. *Cell* 154, 1060-1073, doi:10.1016/j.cell.2013.07.036 (2013).

Roesch, A. et al. A temporarily distinct subpopulation of slow-cycling melanoma cells is required for continuous tumor growth. Cell 141, 583-594, doi:10.1016/j.cell.2010.04.020 (2010).

Sevenich, L. et al. Analysis of tumour- and stroma-supplied proteolytic networks reveals a brain-metastasis-promoting role for cathepsin S. Nature cell biology 16, 876-888, doi:10.1038/ncb3011 (2014).

Ugel, S., De Sanctis, F., Mandruzzato, S. & Bronte, V. Tumor-induced myeloid deviation: when myeloid-derived suppressor cells meet tumor-associated macrophages. *The Journal of clinical investigation* 125, 3365-3376, doi:10.1172/JCI80006 (2015).

Valiente, M. et al. Serpins promote cancer cell survival and vascular co-option in brain metastasis. *Cell* 156, 1002-1016, doi:10.1016/j.cell.2014.01.040 (2

Wolins, N. E. et al. OP9 mouse stromal cells rapidly differentiate into adipocytes: characterization of a useful new model of adipogenesis. *J Lipid Res* 47, 450-460, doi:10.1194/jlr.D500037-JLR200 (2006).

Young, D. et al. Increase in head and neck cancer in younger patients due to human papillomavirus (HPV). Oral oncology 51, 727-730, doi:10.1016/j.oraloncology.2015.03.015 (2015).014).

Yumoto, K., Berry, J. E., Taichman, R. S. & Shiozawa, Y. A novel method for monitoring tumor proliferation in vivo using fluorescent dye DiD. *Cytometry. Part A the journal of the International Society for Analytical Cytology* 85, 548-555, doi:10.1002/cyto.a.22434 (2014)

Zhang, X. H. et al. Selection of bone metastasis seeds by mesenchymal signals in the primary tumor stroma. *Cell* 154, 1060-1073, doi:10.1016/j.cell.2013.07.036 (2013)

The invention claimed is:

1. A method of treating or inhibiting metastatic cancer in a mammal, comprising administering an effective amount of a CD36 antagonist to the mammal, wherein the mammal has a cancer, and wherein the administering reduces metastasis progression or metastasis initiation.

2. The method of claim 1, wherein the mammal has at least one metastatic tumor prior to administering the CD36 antagonist.

3. The method of claim 2, wherein the mammal has at least one tumor metastasis in a lung.

4. The method of claim 2, wherein the mammal has one or more metastases in a lymph node.

5. The method of claim 1, wherein the mammal has a tumor with high expression level of CD36 relative to normal tissue.

6. The method of claim 1, wherein the CD36 antagonist is an anti-CD36 antibody.

7. The method of claim 6, wherein the antibody is a full length antibody, a single chain antibody, a scFv, a Fab fragment, or a F(ab')$_2$ fragment.

8. The method of claim 6, wherein the antibody is a humanized antibody or antigen-binding fragment thereof.

9. The method of claim 1, wherein the CD36 antagonist inhibits the binding of CD36 to oxidized LDL and blocks incorporation of oxidized LDL into cells.

10. The method of claim 1, wherein the CD36 antagonist inhibits the binding of CD36 to fatty acids and blocks incorporation of fatty acids into cells.

11. The method of claim 1, wherein the CD36 antagonist inhibits the binding of CD36 to oxidized LDL, inhibits the binding of CD36 to fatty acids, blocks the incorporation of oxidized LDL into cells, and blocks the incorporation of fatty acids into cells.

12. The method of claim 11, wherein the CD36 antagonist does not substantially inhibit the interaction of CD36 with thrombospondin.

13. The method of claim 1, wherein the administration reduces the number of metastases.

14. The method of claim 1, wherein the administration reduces the size of metastases.

15. The method of claim 14, wherein the administration reduces the size of lymph node metastases by more than 80%-90%.

16. The method of claim 1, wherein the administration decreases metastatic penetrance or growth.

17. The method of claim 1, wherein the mammal is a human being.

18. The method of claim 1, wherein the CD36 antagonist is administered every three days.

19. The method of claim 1, wherein the mammal receives an initial dose of the CD36 antagonist at a first time point that is higher than one or more subsequent or maintenance doses.

20. The method of claim 1, wherein the cancer is a melanoma.

21. The method of claim 1, wherein the cancer is OSCC oral squamous cell carcinoma.

22. The method of claim 1, wherein the cancer is breast cancer.

* * * * *